(12) United States Patent
Junker et al.

(10) Patent No.: US 7,432,079 B2
(45) Date of Patent: Oct. 7, 2008

(54) PLANT VIRUS COAT FUSION PROTEINS WITH GDF8 EPITOPES AND VACCINES THEREOF

(75) Inventors: David E. Junker, San Diego, CA (US); Mark D. Cochran, Carlsbad, CA (US); Mark L. Smith, Davis, CA (US); Kenneth E. Palmer, Vacaville, CA (US); Gregory P. Pogue, Vacaville, CA (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 86 days.

(21) Appl. No.: 11/314,397

(22) Filed: Dec. 21, 2005

(65) Prior Publication Data

US 2006/0159696 A1    Jul. 20, 2006

Related U.S. Application Data

(60) Provisional application No. 60/640,408, filed on Dec. 30, 2004, provisional application No. 60/665,690, filed on Mar. 28, 2005.

(51) Int. Cl.
| | |
|---|---|
| C12N 15/62 | (2006.01) |
| C12N 15/63 | (2006.01) |
| C12N 5/10 | (2006.01) |
| C12N 1/19 | (2006.01) |
| C12N 1/21 | (2006.01) |
| C07K 14/00 | (2006.01) |

(52) U.S. Cl. ............... 435/69.7; 435/419; 435/414; 435/252.3; 435/254.11; 435/320.1; 536/23.1; 536/23.4; 530/350

(58) Field of Classification Search .................. None
See application file for complete search history.

(56) References Cited

U.S. PATENT DOCUMENTS

| | | | |
|---|---|---|---|
| 5,316,931 | A | 5/1994 | Donson et al. |
| 5,422,110 | A | 6/1995 | Potter et al. |
| 5,476,657 | A | 12/1995 | Potter |
| 5,708,155 | A | 1/1998 | Potter et al. |
| 5,827,733 | A | 10/1998 | Lee et al. |
| 5,871,750 | A | 2/1999 | Potter |
| 5,977,438 | A | 11/1999 | Turpen et al. |
| 6,004,937 | A | 12/1999 | Wood et al. |
| 6,033,895 | A | 3/2000 | Garger et al. |
| 6,037,456 | A | 3/2000 | Garger et al. |
| 6,042,832 | A | 3/2000 | Koprowski et al. |
| 6,096,506 | A | 8/2000 | Lee et al. |
| 6,303,779 | B1 | 10/2001 | Garger et al. |
| 6,344,597 | B1 | 2/2002 | Fitzmaurice |
| 6,368,597 | B1 | 4/2002 | Strassmann et al. |
| 6,369,201 | B1 | 4/2002 | Barker et al. |
| 6,399,312 | B2 | 6/2002 | Wu-Wong et al. |
| 6,468,535 | B1 | 10/2002 | Lee et al. |
| 6,607,884 | B1 | 8/2003 | Lee et al. |
| 6,617,440 | B1 | 9/2003 | Findly |
| 6,656,475 | B1 | 12/2003 | Lee et al. |
| 6,656,726 | B1 | 12/2003 | Fitzmaurice et al. |
| 6,730,306 | B1 | 5/2004 | Pogue et al. |
| 6,740,740 | B2 | 5/2004 | Garger et al. |
| 2001/0014330 | A1 | 8/2001 | Harland et al. |
| 2002/0127234 | A1 | 9/2002 | El Halawani et al. |
| 2002/0157125 | A1 | 10/2002 | Lee et al. |
| 2003/0065137 | A1 | 4/2003 | Barker et al. |
| 2003/0074680 | A1 | 4/2003 | Lee et al. |
| 2005/0143306 | A1 | 6/2005 | Junker et al. |

FOREIGN PATENT DOCUMENTS

| | | |
|---|---|---|
| EP | 0 067 553 A2 | 12/1982 |
| EP | 0 690 873 B1 | 6/2003 |
| GB | 2 333 706 A | 8/1999 |
| WO | WO 98/33887 | 8/1998 |
| WO | WO 99/42573 | 8/1999 |
| WO | WO 01/26672 A1 | 4/2001 |
| WO | WO 03/027248 A2 | 4/2003 |
| WO | WO 2004/032622 A2 | 4/2004 |
| WO | WO 2004/052930 A2 | 6/2004 |
| WO | WO 2004/058988 A2 | 7/2004 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Bird, Robert E. et al.; "Single-chain antigen-binding proteins"; Science 242: 423-426 (Oct. 1988).
Dawson, William O. et al.; "cDNA cloning of the complete genome of tobacco mosaic virus and production of infectious transcripts"; Proc. Natl. Acad. Sci. USA 83: 1832-1836 (Mar. 1986).
Gonzalez-Cadavid, Nestor F. et al.; "Organization of the human myostatin gene and expression in healthy men and HIV-infected men with muscle wasting"; Proc. Natl. Acad. Sci. USA 95:14938-14943 (Dec. 1998).

(Continued)

Primary Examiner—Elizabeth C. Kemmerer

(57) ABSTRACT

The invention provides a fusion protein comprising a plant virus coat protein and a GDF8 peptide domain, or antigenic fragment of the GDF8 peptide domain. Plant virus vectors expressing the fusion protein and methods of using these vectors are also provided.

28 Claims, 12 Drawing Sheets

OTHER PUBLICATIONS

Huston, James S. et al.; "Protein engineering of antibody binding sites: Recovery of specific activity in an anti-digoxin single-chain Fv analogue produced in *Escherichia coli*"; Proc. Natl. Acad. Sci. USA 85: 5879-5883 (Aug. 1988).

McPherron, Alexandra C. et al.; "Regulation of skeletal muscle mass in mice by a new TGF-β superfamily member"; Nature 387:83-90 (May 1997).

Modelska, Anna et al.;"Immunization against rabies with plant-derived antigen"; Proc. Natl. Acad. Sci. USA 95: 2481-2485 (Mar. 1998).

Namba, Keiichi et al.; "Visualization of protein-nucleic acid interactions in a virus: Refined structure of intact tobacco mosaic virus at 2.9 Å resolution by X-ray fiber diffraction"; Journal of Molecular Biology 208: 307-325 (1989).

Pattanayek, Rekha et al.; "Structure of the U2 strain of tobacco mosaic virus refined at 3.5Å resolution using X-ray fiber diffraction"; Journal of Molecular Biology 228: 516-528 (1992).

PCT International Search Report dated May 25, 2005 for corresponding PCT Application No. PCT/US2004/043125.

Pelham, Hugh R.; "Leaky UAG termination condon in tobacco mosaic virus RNA"; Nature 272: 469-471 (Mar. 1978).

Pogue, Gregory et al.; "Making an Ally From An Enemy: Plant Virology and the New Agriculture"; Annual Review of Phytopathology 40: 45-74 (2002).

R&D Systems, Inc., Antibody Reference Guide and Catalog, May 1, 2003.

Rebbapragada, A. et al.; "Myostatin signals through a Transforming Growth Factor β-Like Signaling Pathway To Block Adipogenesis"; Molecular and Cellular Biology 23(20):7230-7242 (Oct. 2003).

Skuzeski, James M. et al.; "The signal for a leaky UAG stop codon in several plant viruses includes the two downstream codons"; Journal of Molecular Biology 218: 365-373 (1991).

Thies, Scott R. et al.; "GDF-8 Propeptide Binds to GDF-8 and Antagonizes Biological Activity by Inhibiting GDF-8 Receptor Binding"; Growth Factors 18: 251-259 (2001).

Wang, Hong et al.; "Structure Determination of Cucumber Green Mottle Mosaic Virus by X-ray Fiber Diffraction: Significance for the Evolution of Tobamoviruses"; Journal of Molecular Biology 239: 371-384 (1994).

Yusibov, Vidadi et al.; "Antigens produced in plants by infection with chimeric plant viruses immunize against rabies virus and HIV-1"; Proc. Natl. Acad. Sci. USA; 94: 5784-5788 (May 1997).

Geysen H M et al.; "Use of peptide synthesis to probe viral antigens for epitopes to a resolution of a single aminoacid". Proceedings of the National Academy of Sciences of USA, National Academy of Science, Washington DC; vol. 81 (1) Jul. 1984: 3998-4002.

PCT International Search Report mail date Sep. 20, 2006 for corresponding PCT application No. PCT/US2005/046363, international filing date Dec. 21, 2005.

* cited by examiner

FIG. 1

| 1 | Entire GDF8 Protein | 375 |

| | GDF8 Acitve Region | |
| 266 | | 375 |

GDF8 Peptides Corresponding to DJ5
Residue Nos. Based on Precursor GDF8

Animal Species and Genebank Nos.
For the complete precursor GDF8 of
Each Cited Species

| 327 | | | | | | | | | | | | | | | | | | | 346 | Species |
|---|---|---|---|---|---|---|---|---|---|---|---|---|---|---|---|---|---|---|---|---|
| V | H | Q | A | N | P | R | G | S | A | G | P | C | C | T | P | T | K | M | S | Anas platyrhynchos (duck) AAL35275 |
| V | H | Q | A | N | P | R | G | S | A | G | P | C | C | T | P | T | K | M | S | Anser anser (goose) AAL35276 |
| V | L | Q | A | N | P | R | G | S | A | G | P | C | C | T | P | T | K | M | S | Anser anser (goose) AAR18246 |
| V | H | Q | A | N | P | R | G | S | A | G | P | C | C | T | P | T | K | M | S | Bos taurus (cow) AAB86687 |
| V | H | Q | A | N | P | R | G | S | A | G | P | C | C | T | P | T | K | M | S | Canis familiaris (dog) AAR14343 |
| V | H | Q | A | N | P | R | G | S | A | G | P | C | C | T | P | T | K | M | S | Capra hircus (goat) AAR12161 |
| V | H | Q | A | N | P | K | G | S | A | G | P | C | C | T | P | T | K | M | S | Columba livia (pigeon) AAL35277 |
| V | N | Q | A | S | P | R | G | S | A | G | P | C | C | T | P | T | K | M | S | Coturnix chinensis (quail) AAL35278 |
| V | H | Q | A | N | P | R | G | S | A | G | P | C | C | T | P | T | K | M | S | Danio rerio (zebrafish) AAB86693 |
| V | H | Q | A | N | P | R | G | T | A | G | P | C | C | T | P | T | K | M | S | Equus caballus (horse) BAB16046 |
| V | H | Q | A | N | P | R | G | P | A | G | P | C | C | T | P | T | K | M | S | Gallus gallus (chicken) AAK18000 |
| V | H | Q | A | N | P | R | G | T | A | G | P | C | C | T | P | T | K | M | S | Gallus gallus (chicken) AAR18244 |
| V | H | Q | A | N | P | R | G | S | A | G | P | C | C | T | P | T | K | M | S | Homo sapiens (human) NP_005250 |
| V | H | Q | A | N | P | R | G | T | A | G | P | C | C | T | P | T | K | M | S | I. punctatus (catfish) AAK84666 |
| V | N | K | A | N | P | R | G | S | A | G | P | C | C | T | P | T | K | M | S | Lepus capensis (hare) AAN87890 |
| V | H | Q | A | N | P | R | G | T | A | G | P | C | C | T | P | T | K | M | S | Macaca fascicularis (monkey) AAL17640 |
| V | H | Q | A | N | P | R | G | S | A | G | P | C | C | T | P | T | K | M | S | Meleagris gallopavo (turkey) AAB86692 |
| V | N | K | A | N | P | R | G | T | A | G | P | C | C | T | P | T | K | M | S | Morone chrysops (white bass) AAK28707 |
| V | H | Q | A | N | P | R | G | S | A | G | P | C | C | T | P | T | K | M | S | Mus musculus (house mouse) AAC53167 |
| V | N | K | A | N | P | K | G | S | A | G | P | C | C | T | P | T | K | M | S | O. mykiss (trout) AAK71707 |
| V | H | Q | A | N | P | R | G | S | A | G | P | C | C | T | P | T | K | M | S | Ovis aries (sheep) AAB86689 |
| V | H | Q | A | N | P | R | G | S | A | G | P | C | C | T | P | T | K | M | S | Papio hamadryas (baboon) AAB86686 |
| V | H | Q | A | N | P | R | G | S | A | G | P | C | C | T | P | T | K | M | S | Rattus norvegicus (rat) AAB86691 |
| V | N | K | A | N | P | R | G | T | A | G | P | C | C | T | P | T | K | M | S | Salmo salar (salmon) CAC19541 |
| V | N | K | A | N | P | R | G | T | A | G | P | C | C | T | P | T | K | M | S | Sparus aurata (seabream) AAL05943 |
| V | H | Q | A | N | P | R | G | S | A | G | P | C | C | T | P | T | K | M | S | Sus scrofa (pig) AAC08035 |
| V | L | Q | A | N | P | R | G | S | A | G | P | C | C | T | P | T | K | M | S | Sus scrofa (pig) AAR18245 |

FIG 6A

Forward (top) strand:   5' C ATG $n_1n_2n_3$ ———— $n_7n_8n_9$ G 3'
Reverse (bottom) strand: 5' CCGG C $n_9n_8n_7$ ———— $n_3n_2n_1$ 3'

FIG 6B

```
TMV_U5_full_MPYTINSPSQFVYLSSAYADPVCLINLCTNALGNQFQTQQ        40
TMV_U1_full_MSYSITTPSQFVFLSSAWADPIELINLCTNALGNQFQTQQ        40
DJ5(12)_epitope_.............................................  0
Consensus TMV_U5_full_ARTTVQQQFADAWKPVPSMTVRFPASDFVVYRYNSTLDPL        80
TMV_U1_full_ARTVVQRQFSEVWKPSPQVTVRFPDSDFKVYRYNAVLDPL        80
DJ5(12)_epitope_.............................................  0
Consensus TMV_U5_full_ITALLNSFDTRNRIIEVENQPANTTEIVNATQRVDDATV       120
TMV_U1_full_VTALLGAFDTRNRIIEVENQANPTTAETLCATRRVDDATV       120
DJ5(12)_epitope_................VHQANPRGSAGP...........       12
Consensus                            q  p TMV_U5_full_AIRASINNLANELVRGTGMFNQASFETASGLVWTTTPAT       159
TMV_U1_full_AIRSAINNLIVELIRGTGSYNRSSFESSGLVWTSGPAT        159
DJ5(12)_epitope_.............................................  12
Consensus
```

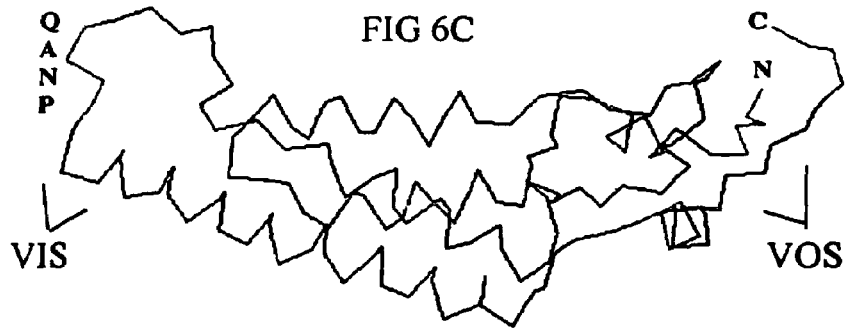

*Nicotiana tabacum* [gbpln]: 1211 CDS's (430056 codons)

| Amino Acid | Codon | Number | /1000 | Fraction |
|---|---|---|---|---|
| Gly | GGG | 4554.00 | 10.59 | 0.15 |
| Gly | GGA | 10299.00 | 23.95 | 0.35 |
| Gly | GGT | 10001.00 | 23.26 | 0.34 |
| Gly | GGC | 4823.00 | 11.21 | 0.16 |
| Glu | GAG | 11931.00 | 27.74 | 0.44 |
| Glu | GAA | 15268.00 | 35.50 | 0.56 |
| Asp | GAT | 15520.00 | 36.09 | 0.69 |
| Asp | GAC | 6997.00 | 16.27 | 0.31 |
| Val | GTG | 6830.00 | 15.88 | 0.24 |
| Val | GTA | 5239.00 | 12.18 | 0.19 |
| Val | GTT | 11395.00 | 26.50 | 0.40 |
| Val | GTC | 4758.00 | 11.06 | 0.17 |
| Ala | GCG | 2522.00 | 5.86 | 0.08 |
| Ala | GCA | 9680.00 | 22.51 | 0.31 |
| Ala | GCT | 13597.00 | 31.62 | 0.44 |
| Ala | GCC | 5363.00 | 12.47 | 0.17 |
| Arg | AGG | 5116.00 | 11.90 | 0.24 |
| Arg | AGA | 6713.00 | 15.61 | 0.32 |
| Ser | AGT | 5786.00 | 13.45 | 0.17 |
| Ser | AGC | 4162.00 | 9.68 | 0.13 |
| Lys | AAG | 13789.00 | 32.06 | 0.50 |
| Lys | AAA | 14014.00 | 32.59 | 0.50 |
| Asn | AAT | 12038.00 | 27.99 | 0.61 |
| Asn | AAC | 7714.00 | 17.94 | 0.39 |
| Met | ATG | 10619.00 | 24.69 | 1.00 |
| Ile | ATA | 6431.00 | 14.95 | 0.26 |
| Ile | ATT | 12172.00 | 28.30 | 0.50 |
| Ile | ATC | 5980.00 | 13.91 | 0.24 |
| Thr | ACG | 1978.00 | 4.60 | 0.09 |
| Thr | ACA | 7394.00 | 17.19 | 0.33 |
| Thr | ACT | 8929.00 | 20.76 | 0.40 |
| Thr | ACC | 4277.00 | 9.95 | 0.19 |

FIG. 8B

| Amino Acid | Codon | Number | /1000 | Fraction |
|---|---|---|---|---|
| Trp | TGG | 5125.00 | 11.92 | 1.00 |
| End | TGA | 458.00 | 1.06 | 0.37 |
| Cys | TGT | 4156.00 | 9.66 | 0.57 |
| Cys | TGC | 3089.00 | 7.18 | 0.43 |
| End | TAG | 241.00 | 0.56 | 0.20 |
| End | TAA | 531.00 | 1.23 | 0.43 |
| Tyr | TAT | 8029.00 | 18.67 | 0.59 |
| Tyr | TAC | 5618.00 | 13.06 | 0.41 |
| Leu | TTG | 9324.00 | 21.68 | 0.24 |
| Leu | TTA | 6052.00 | 14.07 | 0.15 |
| Phe | TTT | 10821.00 | 25.16 | 0.58 |
| Phe | TTC | 7723.00 | 17.96 | 0.42 |
| Ser | TCG | 2344.00 | 5.45 | 0.07 |
| Ser | TCA | 7513.00 | 17.47 | 0.23 |
| Ser | TCT | 8706.00 | 20.24 | 0.26 |
| Ser | TCC | 4656.00 | 10.83 | 0.14 |
| Arg | CGG | 1634.00 | 3.80 | 0.08 |
| Arg | CGA | 2534.00 | 5.89 | 0.12 |
| Arg | CGT | 3404.00 | 7.92 | 0.16 |
| Arg | CGC | 1721.00 | 4.00 | 0.08 |
| Gln | CAG | 6425.00 | 14.94 | 0.41 |
| Gln | CAA | 9324.00 | 21.68 | 0.59 |
| His | CAT | 5852.00 | 13.61 | 0.62 |
| His | CAC | 3612.00 | 8.40 | 0.38 |
| Leu | CTG | 4370.00 | 10.16 | 0.11 |
| Leu | CTA | 4160.00 | 9.67 | 0.11 |
| Leu | CTT | 10181.00 | 23.67 | 0.26 |
| Leu | CTC | 5112.00 | 11.89 | 0.13 |
| Pro | CCG | 2105.00 | 4.89 | 0.10 |
| Pro | CCA | 8389.00 | 19.51 | 0.39 |
| Pro | CCT | 8045.00 | 18.71 | 0.38 |
| Pro | CCC | 2913.00 | 6.77 | 0.14 |

FIG. 9A

```
agattcactg gtgtggcaag ttgtctctca gactgtacat gcattaaaat tttgcttggc    60
attactcaaa agcaaagaa aagtaaaagg aagaaacaag aacaagaaaa aagattatat   120
tgattttaaa atcatgcaaa aactgcaact ctgtgtttat atttacctgt ttatgctgat   180
tgttgctggt ccagtggatc taaatgagaa cagtgagcaa aagaaaaatg tggaaaaaga   240
ggggctgtgt aatgcatgta cttggagaca aaacactaaa tcttcaagaa tagaagccat   300
taagatacaa atcctcagta aacttcgtct ggaaacagct cctaacatca gcaaagatgt   360
tataagacaa cttttaccca aagctcctcc actccgggaa ctgattgatc agtatgatgt   420
ccagagggat gacagcagcg atggctcttt ggaagatgac gattatcacg ctacaacgga   480
aacaatcatt accatgccta cagagtctga tttctaatg caagtggatg gaaaacccaa   540
atgttgcttc tttaaattta gctctaaaat acaatacaat aaagtagtaa agcccaact   600
atggatatat ttgagacccg tcgagactcc tacaacagtg tttgtgcaaa tcctgagact   660
catcaaacct atgaaagacg gtacaaggta tactggaatc cgatctctga aacttgacat   720
gaaccaggc actggtattt ggcagagcat tgatgtgaag acagtgttgc aaaattggct   780
caaacaacct gaatccaact taggcattga aataaaagct ttagatgaga atggtcatga   840
tcttgctgta accttcccag gaccaggaga agatgggctg aatccgtttt tagaggtcaa   900
ggtaacagac acaccaaaaa gatccagaag ggattttggt cttgactgtg atgagcactc   960
aacagaatca cgatgctgtc gttaccctct aactgtggat tttgaagctt ttggatggga  1020
ttgattatc gctcctaaaa gatataaggc caattactgc tctggagagt gtgaatttgt  1080
attttacaa aaatatcctc atactcatct ggtacaccaa gcaaacccca gaggttcagc  1140
aggcccttgc tgtactccca caaagatgtc tccaattaat atgctatatt ttaatggcaa  1200
agaacaaata atatatggga aaattccagc gatggtagta aacatggaa gaccgctgtg gtgtctcatg  1260
agatttatat taagcgttca taacttccta ccacaggcta taggcctaga gttttcccc tcaacaattt  1320
tgaagctgtg aaattaagta ccacaggcta taggcctaga gtatgctaca ggtttcccc tcaacaattt  1380
cataagctac agtatgtaaa ctaaaagggg gaatatatgc aatggttggc atttaaccat  1440
ccaaacaaat catacaagaa agtttatga tttccagagt ttttgagcta gaaggagatc  1500
aaattacatt tatgttccta tatattacaa catcggcgag gaaatgaaag cgattctcct  1560
tgagttctga gagtatgctt taaagtctat ttctttaaag ttcttgttaa  1620
```

FIG. 9B

```
tatttacaga aaaatccaca tacagtattg gtaaaatgca ggattgttat ataccatcat 1680
tcgaatcatc cttaaacact tgaatttata ttgtatggta gtatacttgg taagataaaa 1740
ttccacaaaa ataggagtgg tgcagcatat gcaattcca ttcctattat aattgacaca 1800
gtacattaac aatccatgcc aacggtgcta atacgatagg ctgaatgtct gaggctacca 1860
ggttatcac ataaaaaaca ttcagtaaaa tagtaagttt ctcttttctt cagggcatt 1920
ttcctacacc tccaaatgag gaatggattt tcttaatgt aagaagaatc attttctag 1980
aggttggctt tcaattctgt agcatacttg gagaaactgc attatcttaa aaggcagtca 2040
aatggtgttt gtttttatca aaatgtcaaa ataacatact tggagaagta tgtaattttg 2100
tctttggaaa attacaacac tgcctttgca acactgcagt ttttatggta aaataataga 2160
aatgatcgac tctatcaata ttgtataaaa agactgaaac aatgcattta tataatatgt 2220
atacaatatt gttttgtaaa taagtgtctc cttttttatt tactttggta tattttaca 2280
ctaaggacat ttcaaattaa gtactaaggc acaaagacat gtcatgcatc acagaaaagc 2340
aactacttat atttcagagc aaattagcag attaaatagt ggtcttaaaa ctccatatgt 2400
taatgattag atggttatat tacaatcatt ttatattttt ttacatgatt aacattcact 2460
tatgattca tgatggctgt ataaagtgt tttgaaattt caatggttta ctgtcattgt 2520
gtttaaatct caacgttcca ttatttttaat acttgcaaaa acattactaa gtataccaaa 2580
ataattgact ctattatctg aaatgaagaa taaactgatg ctatctcaac aataactgtt 2640
acttttattt tataatttga taatgaatat atttctgcat ttattactt ctgttttgta 2700
aattgggatt ttgttaatca aatttattgt actatgacta aatgaaatta tttcttacat 2760
ctaatttgta gaaacagtat aagtatatt aagtgtttt cacatttttt tgaaagacaa 2820
aaa 2823
```

FIG. 10

```
atggatctac agaagttgca gttgtgtgtc tacatctatt tgttcatgtt gatcgtcgcc   60
ggacctgttg acttgaacga aaattctgaa cagaaggaga acgttgagaa ggaaggtttg  120
tgcaacgctt gtacatggcg tcaaaataca aagtccctc gtattgaagc tatcaagatt  180
caaatttttgt ctaagttgag attggaaact gccccaaata tttctaagga cgtcattcgt  240
caattgttgc caaaggcccc accttttgaga gaattgatcg accaatacga tgttcaaaga  300
gacgattctt ctgacggttc cctgaagac gatgactacc atgccactac tgaaactatt  360
atcactatgc caactgaatc cgacttttgg atgcaggttg atggtaagcc aaagtgctgt  420
tttttcaagt tctcttccaa gattcaatac aacaaggttg ttaaagctca attgtggatt  480
tacctttcgtc cagttgaaac accaactact gtgttttgttc agattttgcg tttgattaag  540
ccaatgaagg atgaactag atacacaggt attagatcct tgaagttgga tatgaatcct  600
ggtacaggaa tctgycaatc tatcgacgtt aaaactgttc tcaaaactg gttgaagcaa  660
ccagagtcta atttgggtat cgagattaag gccttgacg aaaacggaca tgacttggcc  720
gttacttttc ctggtcctgg tgaagacggt tgaacccat ttctgaagt taaggttact  780
gatactccta agcgttccag gagagactc ggattggatt gtgatgaaca ttctactgag  840
tctagatgtt gtagatatcc attgaccgtt gatttcgagg ccttcggttg ggattggatc  900
attgccccaa agagatacaa agctaactat tgttccggtg aatgtgagtt cgttttcttg  960
cagaagtacc cacataccca tttggttcat caggctaatc caagaggatc tgctggtcca 1020
tgttgtaccc caactaaat gtccctatc aacatgttgt acttcaacgg taaggagcag 1080
attatttacg gtaagatccc tgctatggtt gttgatagat gtggttgttc tctcgaggat 1140
tacaaggatg acgacgataa gtag                                        1164
```

PLANT VIRUS COAT FUSION PROTEINS WITH GDF8 EPITOPES AND VACCINES THEREOF

CROSS-REFERENCE TO RELATED APPLICATIONS

This application is a non-provisional application that claims priority under 35 U.S.C. § 119(e) of provisional applications U.S. Ser. No. 60/640,408 filed Dec. 30, 2004, and U.S. Ser. No. 60/665,690 filed Mar. 28, 2005, the contents of both of which are hereby incorporated by reference in their entireties.

FIELD OF THE INVENTION

The invention relates to fusion proteins formed by expressing growth and differentiation factor 8, and antigenic peptide fragments of growth and differentiation factor 8, and related antigens and vaccines, in plants using a plant virus vector, and to methods of treating animals with such fusion proteins in order to modulate the activity of growth and differentiation factor 8.

BACKGROUND OF THE INVENTION

Growth and differentiation factor 8 is a protein that is classified with the transforming growth factor-β ("TGF-β") superfamily. Generally, the proteins of the TGF-β superfamily are initially expressed as precursor (a/k/a prohormone) that undergoes proteolytic cleavage at a cluster of basic residues about 110-140 amino acids from the precursor protein C-terminus. In each case, the active, or mature, TGF-β species is believed to be a disulfide-linked dimer of the cleaved precursor protein C-terminal regions.

Growth and differentiation factor 8, hereinafter GDF8, is also art-known as myostatin. The genes encoding the precursor of GDF8 (hereinafter "precursor GDF8") have been cloned from a wide range of organisms. These include the human and murine precursor GDF8 (Nestor et al., 1998, *Proc. Natl. Acad. Sci.* 95:14938-43; U.S. Pat. No. 5,827,733, incorporated by reference herein). It has also been reported that GDF8 immunoreactivity is detectable in human skeletal muscle in both type 1 and type 2 fibers. Antibodies and assays for detecting GDF8 are described, e.g., by U.S. Pat. No. 6,096,506.

It has further been reported that GDF8 plays a role in down-regulating or inhibiting the growth and development of skeletal muscle, as confirmed by GDF8 knock-out mice (McPherron et al., 1997, *Nature* 387:83-90). For this reason, there have been previous attempts, particularly in the field of animal husbandry, to modulate GDF8 activity in animals by several means, with the goal of down-regulating GDF8 activity in order to enhance the growth, and/or relative muscle mass, of various food animals.

For example, U.S. Pat. No. 6,399,312 describes a precursor GDF8 gene promoter and an assay, with the proposal that the assay be used to identify a theoretical inhibitor of that promotor. U.S. Pat. No. 6,656,475 describes a method of inhibiting the effect of GDF8 on a cell by contacting the cell with a GDF8 prodomain that competes for a GDF8 receptor, and reports that the C-terminus of mature GDF8 may vary. U.S. Pat. No. 6,004,937 describes the use of follistatin as a possible antagonist of GDF8. None of these methods has resulted in any practical applications in the fields of animal husbandry or clinical applications (either human or veterinary).

The art has also attempted to employ antibody and vaccine technology for downregulating GDF8 function. For instance, U.S. Pat. No. 6,369,201, incorporated by reference herein, describes peptides, i.e., fragments of GDF8 protein, and a vaccine for eliciting anti-GDF8 antibodies. That patent also reported an unspecified degree of growth or weight gain, relative to controls, in rodents immunized with several of the reported GDF8 peptide fragments.

Other physiological roles for GDF8 have also been described. For example, U.S. Pat. No. 6,368,597, incorporated by reference herein, has suggested that inhibiting GDF8 function is useful for treating Type II diabetes, e.g., by administering an anti-GDF8 antibody or anti-GDF8 vaccine to a patient having this condition.

Recently, U.S. Pat. No. 6,730,306, the contents of which are incorporated by reference herein, has described recombinant plant viruses that express chimeric proteins. These chimeric proteins are formed by the fusion of a plant viral (or virus) coat protein (VCP), and a peptide or polypeptide of interest. According to U.S. Pat. No. 6,730,306, by infecting plant cells with such recombinant plant viruses, relatively large quantities of the desired fusion proteins are produced. When a VCP protein is fused with a polypeptide antigen of interest, the location of the fused polypeptide antigen must be carefully selected to be exposed to an immune system, binding antibody, and the like. With appropriate protein engineering, the fusion VCP may be used as an immunogen or antigen to induce an antibody response and/or protective immunity against the polypeptide of interest, or as a reagent for developing and conducting immunoassays useful in detecting such a polypeptide of interest.

There remains a longstanding need in the art for improved antigens and immunogens for eliciting an anti-GDF8 immune response, as well as for improved GDF8 antibodies capable of highly specific binding to GDF8.

The citation of any reference herein should not be construed as an admission that such reference is available as "Prior Art" to the instant application.

SUMMARY OF THE INVENTION

The present invention solves these and other shortcomings in the art by providing plant virus coat protein (VCP) fusion proteins comprising useful epitopes of the GDF8 protein ("GDF8-VCP fusion proteins"),e.g., fusion proteins comprising peptide fragments of GDF8 of 50 residues or less, comprising at least one specific neutralizing epitope for GDF8. The present invention further provides antibodies, antibody fragments and related binding proteins elicited by the GDF8-VCP fusion proteins and/or fragments thereof, and methods of making and using the same.

In one embodiment of the invention, the inventive fusion proteins include a GDF8 peptide domain that comprises from about residue 327 to about residue 346 of natural, human precursor GDF8 (SEQ ID NO: 1), illustrated below.

$^1$MQKLQLCVYIYLFMLIVAGPVDLNENSEQKENVEKEGLCNACTWRQNTK

SSRIEAIKIQILSKLRLETAPNISKDVIRQLLPKAPPLRELIDQYDVQRD

DSSDGSLEDDDYHATTETIITMPTESDFLMQVDGKPKCCFFKFSSKIQYN

KVVKAQLWIYLRPVETPTTVFVQILRLIKPMKDGTRYTGIRSLKLDMNPG

TGIWQSIDVKTVLQNWLKQPESNLGIEIKALDENGHDLAVTFPGPGEDGL

NPFLEVKVTDTPKRSRRDFGLDCDEHSTESRCCRYPLTVDFEAFGWDWII

-continued

APKRYKANYCSGECEFVFLQKYPHTHLVHQANPRGSAGPCCTPTKMSPIN

MLYFNGKEQIIYGKIPAMVVDRCGCS³⁷⁵

In another embodiment, the GDF8 peptide domain comprises from about residue 327 to about residue 338 and preferably comprises from about residue 329 to about residue 332 of natural, human precursor GDF8. The DJ5 (20 mer) GDF8 peptide domain is illustrated below, in both single and triple letter code, along with residue numbering based on the precursor GDF8 of SEQ ID NO:1, for the convenience of the reader (see, U.S. patent application Ser. No. 11/019,001, filed on Dec. 21, 2004, the contents of which are hereby incorporated by reference in their entireties).

```
                       DJ5 (SEQ ID NO:8)

327 328 329 330 331 332 333 334 335 336 337 338 339 340 341
 V   H   Q   A   N   P   R   G   S   A   G   P   C   C   T
Val His Gln Ala Asn Pro Arg Gly Ser Ala Gly Pro Cys Cys Thr 342 343 344 345 346
 P   T   K   M   S
Pro Thr Lys Met Ser
```

Optionally, the GDF8 peptide domain employed in the inventive fusion protein includes conservative single amino acid substitutions. Simply by way of example, these can be from one through at least five amino acid positions within the peptide. In particular, there is optionally at least one conservative amino acid substitution, e.g., between residues 327 to 346 of GDF8. In another option, the GDF8 peptide domain includes conservative amino acid substitutions at no more than five amino acid positions within the GDF8 peptide domain. In another embodiment there are, e.g., two conservative amino acid substitutions between residues 327 to 346 of GDF8. In yet another embodiment, there are, e.g., three conservative amino acid substitutions between residues 327 to 346 of GDF8. In still another embodiment, there are, e.g., four conservative amino acid substitutions between residues 327 to 346 of GDF8.

Preferably, the amino acid residue substitutions are at one or more positions, relative to natural, human precursor GDF8 (SEQ ID NO: 1) that are marked by the amino acid variations of the interspecies alignment of FIG. 2. These are at residues 328, 329, 331, 333 and 335, and combinations thereof, wherein, (a) amino acid residue 328 is His, Leu or Asn;

(b) amino acid residue 329 is Gln or Lys;

(c) amino acid residue 331 is Asn or Ser;

(d) amino acid residue 333 is Arg or Lys; and/or (e) amino acid residue 335 is Ser, Pro or Thr.

Preferably, the substituted GDF8 peptide domain binds to rat monoclonal antibody MAB788 (R& D Systems, Inc, Minneapolis, Minn.).

Thus, the invention provides a fusion protein comprising a GDF8 peptide domain, wherein the GDF8 peptide domain comprises amino acid residues 327 to 346 of SEQ ID NO:1, or an antigenic fragment of the GDF8 peptide. The antigenic fragment can include, e.g., residues 327 to 338 of SEQ ID NO: 1 and/or residues 329 to 332 of SEQ ID NO: 1. The GDF8 peptide domain is preferably fused to a polypeptide that comprises a virus coat protein, or a fragment thereof.

In one embodiment, a "virus coat protein" or VCP, as described herein, when a part of an inventive fusion protein, includes all of the amino acid residues found in the native (non-fusion) VCP. In an optional alternative embodiment, the term "virus coat protein" also encompasses a fragment or fragments of a native VCP that results from the linkage to a GDF8 peptide domain and/or that results from the insertion of a GDF8 peptide domain within the sequence of the native VCP (e.g. an insertion at the N- and/or C-terminals and or anywhere therebetween) and/or the fragment that results from the deletion from one or more amino acid residue from the VCP protein as a consequence of engineering the insertion or fusion of the GDF8 peptide domain. Thus, a VCP "fragment" as part of a fusion protein is a VCP optionally missing from 1 to about 10 residues relative to the native VCP, and/or that has been divided into two or more domains by the insertion of the GDF8 peptide domain.

Any suitable virus can be employed as a fusion partner, such as a plant virus. A preferred plant virus is, for example a tobamovirus. Tobamovirus strains can include, e.g., the tobacco mosaic virus ("TMV") type strain (U1), tobacco mild green mosaic virus (U5), tomato mosaic virus, Odontoglossum ringspot virus, ribgrass mosaic virus, Sunn-hemp mosaic viorus, and/or cucumber green mottle mosaic virus.

The fusion protein is preferably selected from the group of polypeptides exemplified hereinbelow, that are according to SEQ ID NO: 47, SEQ ID NO: 48, SEQ ID NO: 49, SEQ ID NO: 50, SEQ ID NO: 51, that have a 20 mer GDF8 peptide domain, and/or according to SEQ ID NO: 54 or SEQ ID NO: 55, that have the 12 mer GDF8 peptide domain.

The fusion protein is generally in the following form:

(a) a plant viral coat protein from a single-stranded plus-sense RNA virus; and (b) the GDF8 peptide domain fused to the viral coat protein at a position selected from one of the following:

(i) the N-terminus of the viral coat protein, (ii) the C-terminus of the coat protein, (iii) 4 amino acids from the C-terminus of the coat protein, (iv) within an externally exposed loop region of the coat protein;

wherein the fusion protein elicits an immune response to GDF8, with or without an adjuvant.

Preferably, the fusion protein comprises a specific neutralization epitope for an anti-GDF8 antibody, e.g., rat anti-GDF8 monoclonal antibody 788 and/or an IgG fraction of goat anti-GDF8 polyclonal antiserum.

More preferably, the inventive fusion protein elicits an immune response to GDF8, when presented to the immune system of a vertebrate, with or without an adjuvant.

The invention also provides nucleic acid molecules, e.g., in the form of replicable vectors, that encode the inventive fusion protein, e.g., a nucleic acid molecule that comprises nucleotide 1112 to nucleotide 1171 of SEQ ID NO: 2.

A replicable vector according to the invention is optionally a plasmid, a phage, a cosmid, and/or a virus. A plant virus, such as a tobamovirus, is preferred. More preferably, the replicable vector is a TMV from the U1 or U5 strains. The engineered chimeric TMV expressing the GDF8 peptide domain is exemplified herein as TMV-FV1, TMV-FV2, TMV-FV3, TMV-FV4, TMV-FV5, TMV-FV6 and TMV-FV7. Host cells and plants, e.g., *Nicotiana* plants, expressing the replicable vector are also provided by the present invention.

The invention further provides a vaccine composition, e.g., that includes the inventive fusion protein and/or the above-described replicable expression vector, such as the TMV virus that expresses the fusion protein. Optionally, art-known adjuvants are also included in the inventive vaccine composition.

The invention also provides a number of useful methods and processes. For example, the invention provides a method of producing the inventive fusion protein, including the steps of culturing a host plant or plant cell that includes the above noted replicable expression vector, expressing the encoded fusion protein, and recovering the fusion protein.

Preferably, the method of producing the inventive fusion protein includes the steps of, infecting a host plant with a recombinant virus expressing a fusion protein that includes the GDF8 peptide domain, e.g., with one or more of the exemplified TMV-FV1, TMV-FV2, TMV-FV3, TMV-FV4, TMV-FV5, TMV-FV6 and TMV-FV7 viruses, and then harvesting and purifying the replicated virus. Optionally, the fusion protein is further isolated from the purified recombinant TMV by separating the fusion coat protein from the TMV genomic RNA.

Additional provided methods include a method of eliciting an anti-GDF8 immune response in an animal, comprising administering to the animal an effective amount of the inventive vaccine composition.

Most preferably, the invention provides a method of down-regulating GDF8 activity in an animal comprising immunizing the animal with an effective amount of the inventive vaccine composition.

BRIEF DESCRIPTION OF THE DRAWINGS

FIG. 1 illustrates overlapping peptides DJ1 through DJ7, in the GDF8 active region (i.e., mature GDF8), that is from residues 266-375 of the precursor GDF8 sequence.

FIG. 2 illustrates the alignment of the human DJ5 peptide sequence (SEQ ID NO: 8) compared to the analogous 20-residue peptides, as located in the precursor GDF8 proteins of the recited additional animal species. The amino acid residue positions of 321 through 347 are based on the human precursor GDF8. The Genebank accession numbers (incorporated by reference herein) identify the entire published protein sequence for each respective species.

The aligned peptides have the following SEQ ID NOs.

| | |
|---|---|
| *Anas platyrhynchos* (duck) AAL35275 | (SEQ ID NO: 11) |
| *Anser anser* (goose) AAL35276 | (SEQ ID NO: 12) |
| *Anser anser* (goose) AAR18246 | (SEQ ID NO: 13) |
| *Bos taurus* (cow) AAB86687 | (SEQ ID NO: 14) |
| *Canis familiaris* (dog) AAR14343 | (SEQ ID NO: 15) |
| *Capra hircus* (goat) AAR12161 | (SEQ ID NO: 16) |
| *Columba livia* (pigeon) AAL35277 | (SEQ ID NO: 17) |
| *Coturnix chinensis* (quail) AAL35278 | (SEQ ID NO: 18) |
| *Danio rerio* (zebrafish) AAB86693 | (SEQ ID NO: 19) |
| *Equus caballus* (horse) BAB16046 | (SEQ ID NO: 20) |
| *Gallus gallus* (chicken) AAK18000 | (SEQ ID NO: 21) |
| *Gallus gallus* (chicken) AAR18244 | (SEQ ID NO: 22) |
| *Homo sapiens* (human) NP-005250 | (SEQ ID NO: 8) |
| *I. punctatus* (catfish) AAK84666 | (SEQ ID NO: 23) |
| *Lepus capensis* (hare) AAN87890 | (SEQ ID NO: 24) |
| *Macaca fascicularis* (monkey) AAL17640 | (SEQ ID NO: 25) |
| *Meleagris gallopavo* (turkey) AAB86692 | (SEQ ID NO: 26) |
| *Morone chrysops* (white bass) AAK28707 | (SEQ ID NO: 27) |
| *Mus musculus* (house mouse) AAC53167 | (SEQ ID NO: 28) |
| *O. mykiss* (trout) AAK71707 | (SEQ ID NO: 29) |
| *Ovis aries* (sheep) AAB86689 | (SEQ ID NO: 30) |
| *Papio hamadryas* (baboon) AAB86686 | (SEQ ID NO: 31) |
| *Rattus norvegicus* (rat) AAB86691 | (SEQ ID NO: 32) |
| *Salmo salar* (salmon) CAC19541 | (SEQ ID NO: 33) |
| *Sparus aurata* (seabream) AAL05943 | (SEQ ID NO: 34) |

-continued

| | |
|---|---|
| *Sus scrofa* (pig) AAC08035 | (SEQ ID NO: 35) |
| *Sus scrofa* (pig) AAR18245 | (SEQ ID NO: 36) |

Figure 3:
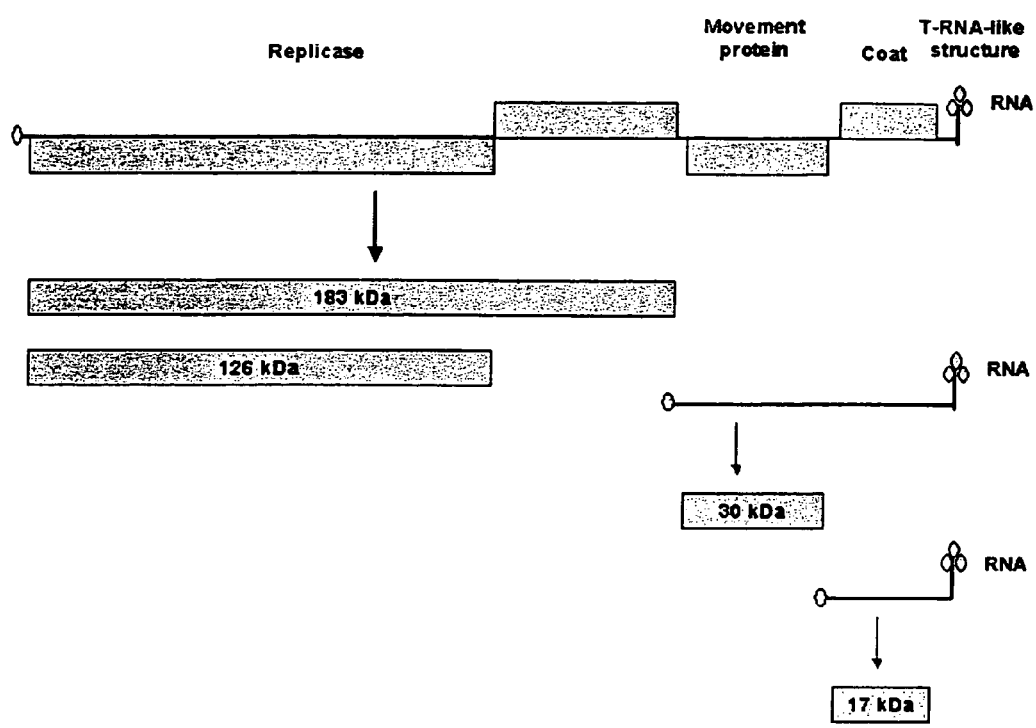

FIG. 3 outlines the genomic organization and gene expression strategy of tobamoviruses. Tobamoviruses have a genomic RNA of approximately 6.4 kb. The genomic RNA is used as an mRNA and translated to produce the replicase protein. TMV produces two replicase proteins, with the larger protein (183 kDa) being produced by translational readthrough of an amber (UAG) stop codon. All tobamoviruses produce two smaller coterminal subgenomic RNAs (sgRNA). The coat protein is encoded by the 3'-most sgRNA (17 kDa), and the movement protein by the larger (30 kDa) sgRNA. The virion RNA and sgRNAs are capped. Tobamovirus RNA is not polyadenylated, but contain a tRNA-like structure at the 3' end.

Figure 4:
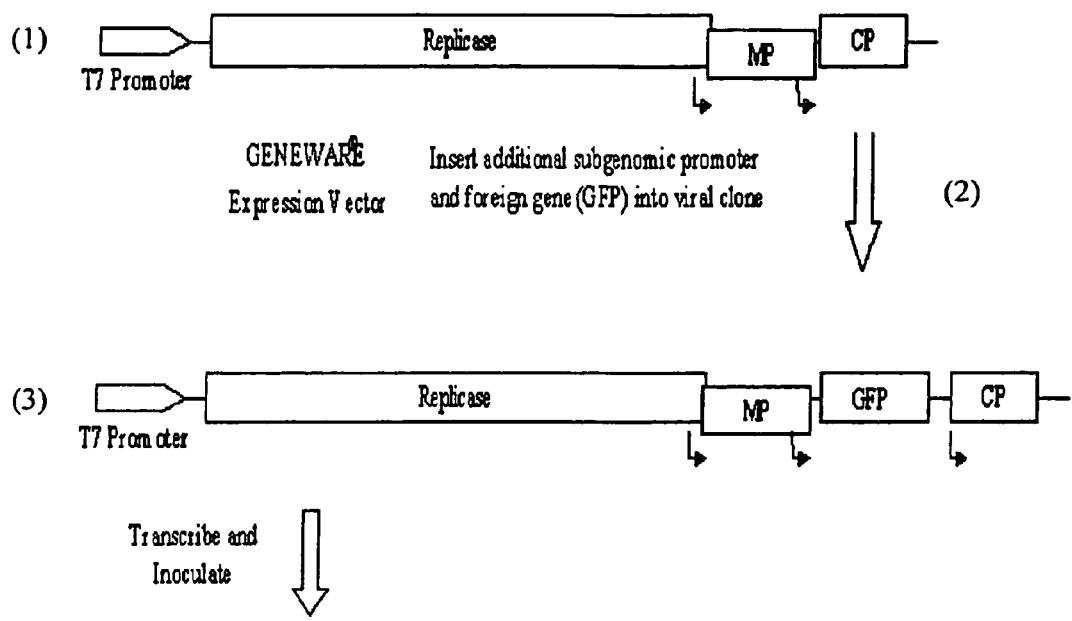

FIG. 4 illustrates the genomic structure of TMV and the construction and utility of GENEWARE® Expression Vectors. (1) shows a cDNA copy of the TMV genome, and the positions of two subgenomic promoters (bent arrows) driving expression of subgenomic messenger RNAs encoding movement protein (MP) and coat protein (CP), respectively. Replicase proteins are translated from the genomic RNA. The GENEWARE® vector (3) was constructed by insertion (2) of an additional subgenomic RNA promoter and multiple cloning site for insertion of foreign genes (illustrated by a green fluorescent protein (GFP) sequence).

Figure 5:
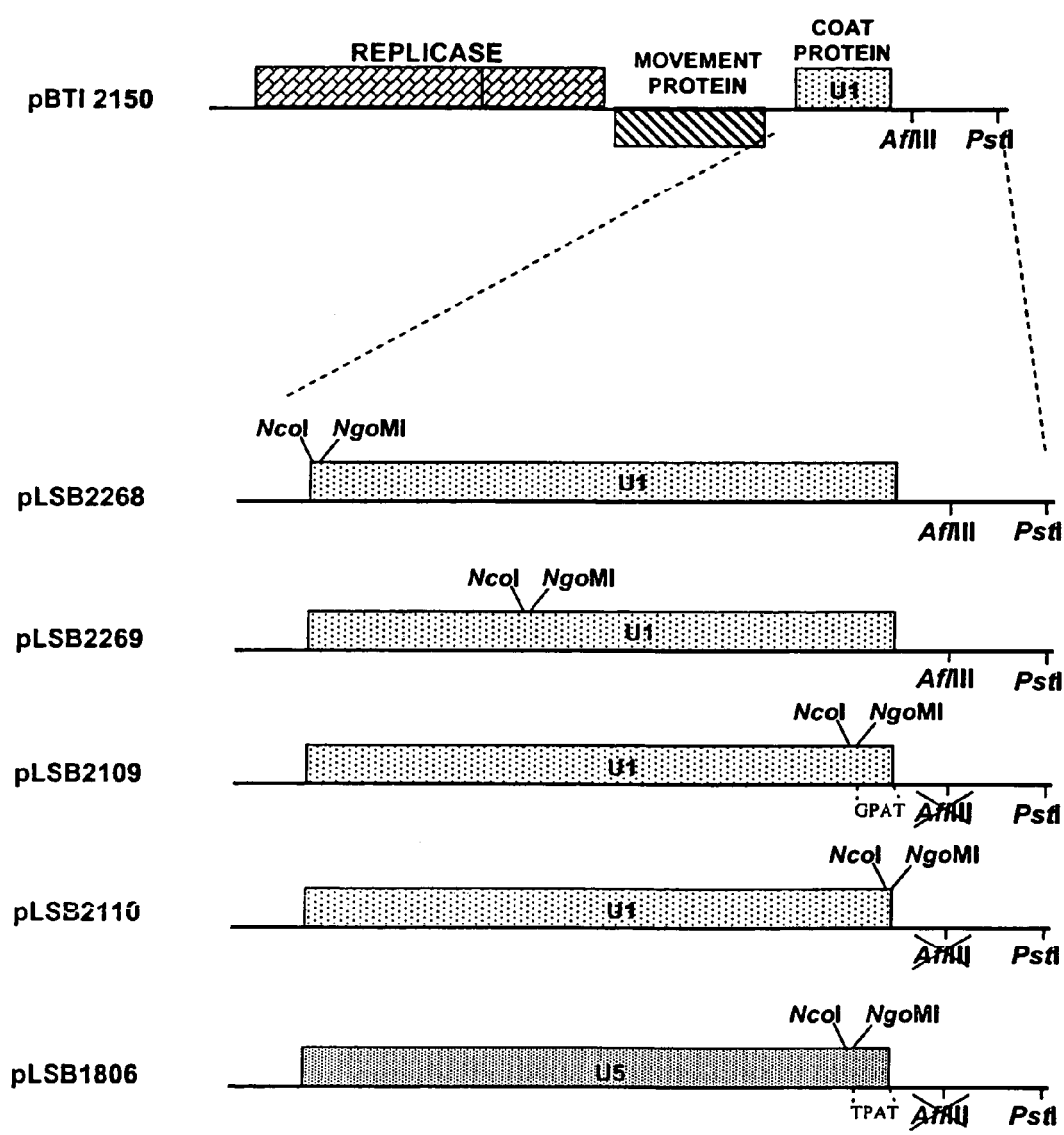

FIG. 5 illustrates five acceptor vectors (pLSB2268, pLSB2269, pLSB2109, pLSB2110, and pLSB1806) that were employed in the generation of the DJ5 epitope coat protein fusions. All five vectors were derived from the same base vector (pBTI 2150). The region surrounding the coat protein is also expanded to show more details. Abbreviations: U1 and U5 indicate that the viral coat protein was derived from the TMV U1 and U5 strains, respectively.

FIG. 6A illustrates the generalized design of the oligonucleotide pair employed to clone the DJ5 epitope into the TMV U1 and TMV U5 coat protein stains. Note: n1n2n3, etc. represent the nucleotides in the forward oligonucleotide and n-1n-2n-3 etc. in the reverse oligonucleotide, represent the reverse complement of the forward nucleotide. The Forward strand and the Reverse strand are disclosed.

FIG. 6B illustrates the amino acid sequence alignment for the TMV U1 coat protein (SEQ ID NO: 56), TMV U5 coat protein (SEQ ID NO: 57) and the N-terminal 12 amino acids of the DJ5 peptide derived from GDF8 (SEQ ID NO: 44).

FIG. 6C illustrates a wire diagram of the TMV U1 coat protein, with the surface exposed N and C terminal regions, together with the QANP (SEQ ID NO: 58) residues, highlighted. "VIS" indicates the virus inner surface and "VOS" indicates the virus outer surface.

Figure 7:
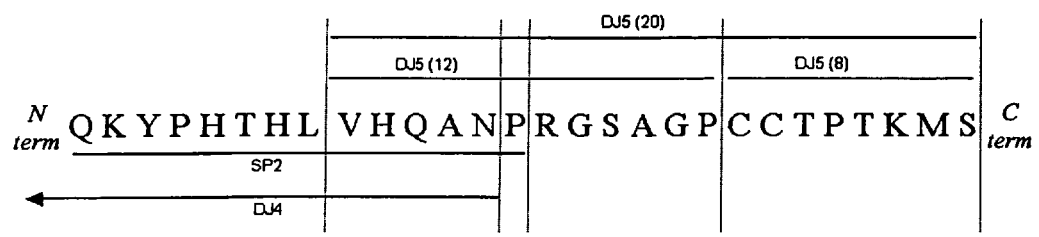

FIG. 7 illustrates the GDF8 amino acid sequence (residues 319 through 346 of SEQ ID NO: 1) in the DJ5 region, and the DJ5(20), DJ5(12), DJ5(8), SP2 and DJ4 epitopes are indicated. "N term," marks the N terminus of the sequence; "C term," marks the C terminus.

FIG. 8A and FIG. 8B together illustrate the codon usage for *Nicotiana tabacum*. This codon usage table was employed in the creation of the codon optimized oligonucleotides for the generation of the 20 amino acid DJ5 peptide (SEQ ID NO: 45 and SEQ ID NO: 46) and the 12 amino acid DJ5 peptide (SEQ ID NO: 52 and SEQ ID NO: 53) coat protein fusions. The codon employed for each amino acid is underlined.

FIGS. 9A and 9B together illustrate the natural DNA sequence (SEQ ID NO: 2) encoding the GDF8 prohormone (SEQ ID NO: 1). This DNA is well known to the art, but is provided herein simply for convenience.

FIG. 10 illustrates the codon-optimized DNA sequence exemplified by Example 1 (SEQ ID NO: 3) obtained by reverse translating SEQ ID NO: 1 using yeast preferred codons.

DETAILED DESCRIPTION OF THE INVENTION

Accordingly, the invention provides plant virus GDF8-VCP fusion proteins. These GDF8-VCP fusion proteins are able to serve directly as immunogens for eliciting anti-GDF8 immune responses in animals, e.g., in order to downregulate GDF8 and/or promote an increase in muscle mass and/or as reagents for methods of detecting GDF8 or antibodies binding to GDF8. These GDF8-VCP fusion proteins can also be engineered to allow for ready cleavage and recovery of the expressed GDF8 epitopes in a form that is substantially free of the VCP portion of the fusion protein. The GDF8 epitopes are generally referred to herein as GDF8 peptides or peptide fragments. The utility of these GDF8 peptides includes use as immunogens for eliciting an anti-GDF8 immune response in animals, and for use as highly specific antibody-binding targets in GDF8-related assays. The invention also provides virus particle, i.e., virions, comprising GDF8-VCP fusion proteins, and plant cells comprising the same. These are optionally employed as a source from which GDF8-VCP fusion protein is purified, or can be directly employed as an immunogen.

Preferably, the plant virus is a species of the tobamovirus group. Tobamovirus species include, for example, tobacco mosaic virus (type strain, U1). cucumber green mottle mosaic virus (SH strain), frangipani mosaic virus, kyuri green mottle mosaic virus, Odontoglossum ringspot virus, paprika mild mottle virus, pepper mild mottle virus (S strain), ribgrass mosaic virus, Sammons' Opuntia virus, sunn-hemp mosaic virus, tobacco mild green mosaic virus (U5), tobacco mosaic virus (Vulgare strain; ssp. NC82 strain), tomato mosaic virus and Ullucus mild mottle virus. The tobamoviruses exemplified herein were tobacco mosaic virus U1 and tobacco mild green mosaic virus U5, otherwise referred to as TMV U1 and TMV U5, respectively.

The specific binding epitopes of GDF8 were initially identified by contacting anti-GDF8 antiserum with a battery of overlapping GDF8 peptides, and determining the degree of binding activity between the peptides and the antiserum IgG antibodies. The anti-GDF8 antiserum was obtained from a goat immunized with a precursor GDF8 protein having a structure optimized for expression and antigenicity.

In order to more fully appreciate the instant invention, the following definitions are provided. The use of singular terms for convenience in description is in no way intended to be so limiting. Thus, for example, reference to a composition comprising "a polypeptide" includes reference to one or more of such polypeptides.

As used herein the term "approximately" is used interchangeably with the term "about" and signifies that a value is within twenty percent of the indicated value i.e., a peptide containing "approximately" 50 amino acid residues can contain between 40 and 60 amino acid residues.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

As used herein, the term, "polypeptide" is used interchangeably with the term "protein," and denotes a polymer comprising two or more amino acids connected by peptide bonds. Preferably, unless otherwise stated herein, the term polypeptide is distinguished from the term, "peptide" as employed herein, by size or chain length, wherein a "peptide" refers to a polymer chain of about fifty or fewer amino acids, and a polypeptide or protein refers to polymer chain comprising more than about fifty amino acids, unless otherwise specified. Optionally, a peptide or a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

A "GDF8 peptide" including a "GDF8 peptide domain" of a fusion protein, according to the invention, is a relatively short fragment derived from the GDF8 protein, e.g., the DJ5 20 mer identified herein. This term optionally includes even smaller fragments of these peptides or peptide domains, such as the 12 mer and 4 mer domains also identified herein, and also optionally including the amino acid substitutions described herein. While not intending to limit the maximum size of a GDF8 peptide or peptide domain, it is preferred that the size of the peptide domain ranges from about 4 to about 50 residues, more preferably it ranges in size from about 4 to about 20 residues, and optionally a GDF8 peptide domain according to the invention ranges in size from about 8 to about 12 residues. In one particular embodiment, the size of the peptide domain ranges from about 5 to about 16 amino acid residues.

As used herein the term "antigenic fragment" in regard to a particular protein and/or peptide is a fragment of that protein/peptide that is antigenic. For example, an antigenic fragment of a GDF8 peptide domain is a fragment of the GDF8 peptide domain that is antigenic. As used herein, an antigenic fragment of a GDF8 peptide domain can be any fragment of the GDF8 peptide domain that is missing as little as a single amino acid from the full-length peptide. In a particular embodiment an antigenic fragment of a GDF8 peptide domain contains about 3 to about 20 amino acid residues. In a particular embodiment the antigenic fragment of a GDF8 peptide domain contains about 4 to about 16 amino acids. In a particular embodiment the antigenic fragment of a GDF8 peptide domain contains about 8 to about 12 amino acids. In another particular embodiment the antigenic fragment of a GDF8 peptide domain contains about 12 to about 20 amino acids. An antigenic fragment of a given GDF8 peptide domain, as the GDF8 peptide domain itself, can be obtained from a recombinant source, from a protein isolated from natural sources, and/or through chemical/peptide synthesis. Thus, an antigenic fragment can be obtained, e.g.: (i) following the proteolytic digestion of a naturally occurring GDF8 or a peptide fragment thereof, (ii) following the proteolytic digestion of a recombinant GDF8 or a peptide fragment thereof, (iii) directly through its recombinant expression either by itself, or as a fusion protein, and/or (iv) it can be generated de novo, e.g., through peptide synthesis.

In another particular embodiment, a GDF8 peptide comprises a peptide domain that has a degree of similarity (and preferably degree of identity) ranging from about 50% similarity (preferably identity) to 100% similarity to the peptide defined by residue numbers 327-346 (SEQ ID NO: 8) of the naturally occurring human precursor of GDF8 (SEQ ID NO: 1).

The terms "purified" or "isolated," as employed herein, refer to materials separated under conditions that reduce or eliminate the presence of unrelated materials, i.e., contaminants or impurities, including native materials from which the material is obtained. For example, a purified or isolated protein is preferably free of other proteins or nucleic acids with which it can be found within a cell. A purified material may contain less than about 25%, preferably less than about 50%, more preferably less than about 75%, and most preferably less than about 90%, of the cellular components with which it was originally associated. Purity can be evaluated by chromatography, gel electrophoresis, immunoassay, composition analysis, biological assay and other methods known in the art. From a functional aspect, an isolated GDF8 peptide according to the invention can be one that is sufficiently separated from other materials, including precursor GDF8 protein and/or mature GDF8 protein, so as to be capable of eliciting an immune response that is specific for the GDF8 peptide.

Methods for purification are well-known in the art. For example, nucleic acids can be purified by precipitation, chromatography, ultracentrifugation and other means. Proteins and polypeptides, as well as peptides, can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction and countercurrent distribution. For some purposes, it is preferable to produce the polypeptide in a recombinant system in which the protein contains an additional sequence tag that facilitates purification, such as, but not limited to, a polyhistidine sequence, FLAG®, GST and/or a sequence that specifically binds to an antibody. The polypeptide can then be purified from a crude lysate of the host cell by chromatography on an appropriate solid-phase matrix. Alternatively, antibodies, or binding fragments thereof, produced against the polypeptide can be used as purification reagents.

The term "substantially pure" indicates the highest degree of purity which can be achieved using conventional purification techniques known in the art and means a nucleic acid, polypeptide, peptide, or other material that is free from other contaminating proteins, nucleic acids and other biologicals derived from an original source organism or recombinant DNA expression system. Substantial purity may be assayed by standard methods and will typically exceed at least about 75%, preferably at least about 90%, more preferably at least about 95% and most preferably at least about 99% purity. Purity evaluation may be made on a mass or molar basis.

A "polynucleotide" or a "nucleic acid molecule" is a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A "vector" or "replication vector" is a replicon, such as a plasmid, phage, or cosmid, to which another nucleic acid segment may be attached or incorporated so as to bring about the replication of the attached segment. The term also comprises a replicon that includes the incorporated or attached nucleic acid segment of interest.

Vectors that can be used in this invention include microbial plasmids, viruses, bacteriophage, integratable DNA fragments and other vehicles that may facilitate integration of the nucleic acids into the genome of the host. Plasmids are the most commonly used form of vector, but all other forms of vectors which serve an equivalent function and which are or become known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Insertion of DNA encoding the inventive GDF8 peptide(s) into a vector is easily accomplished when the termini of both the DNA and the vector comprise compatible restriction sites. If this cannot be done, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). See, e.g., Saiki et al., 1988, *Science* 239:487. The cleaved vector and the DNA fragments may also be modified, if required, by homopolymeric tailing.

Recombinant expression vectors used in this invention are typically self-replicating DNA or RNA constructs comprising nucleic acids encoding one of the inventive GDF8 peptide(s), usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors may also contain an origin of replication that allows the vector to replicate independently of the host cell.

Expression of nucleic acids encoding inventive GDF8 peptide(s) can be carried out by conventional methods in either prokaryotic or eukaryotic cells.

A nucleic acid "coding sequence" or a "sequence encoding" a particular protein or peptide, is a nucleic acid sequence (e.g., DNA or RNA) which is transcribed and/or translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, RNA virus sequences, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

As used herein the terms "fusion protein" and "fusion peptide" are used interchangeably and encompass "chimeric proteins and/or chimeric peptides" and fusion "intein proteins/peptides". A fusion protein comprises at least a portion of a GDF8 peptide of the present invention joined via a peptide bond to at least a portion of another protein. For example, fusion proteins can comprise a marker protein or peptide, or a protein or peptide that aids in the isolation and/or purification and/or antigenicity of a GDF8 peptide of the present invention. A GDF8 fusion protein can comprise at least a portion of a non-GDF8 protein joined via a peptide bond to at least a portion of a GDF8 polypeptide. In preferred embodiments a portion of the GDF8 is functional, i.e., retains its antigenicity. The non-GDF8 sequences can be amino- and/or carboxy-terminal to the GDF8 sequences. This is also contemplated to optionally include a loop fusion, wherein the DJ5 peptide domain is inserted within the carrier polypeptide A recombinant nucleic acid molecule encoding such a fusion protein comprises a sequence encoding at least a portion of a non-GDF8 protein joined in-frame to the GDF8 coding sequence, and can encode a cleavage site for a specific protease, e.g., thrombin or Factor Xa, preferably at or close to the juncture between the GDF8 sequence and the non-GDF8 sequence. In one specific embodiment, the fusion protein is expressed in a CHO cell. Such a fusion protein can be used to isolate the GDF8 peptides of the present invention, through the use of an affinity column that is specific for the protein and/or tag fused to the GDF8 peptide. The purified GDF8 peptide, for example, may then be released from the fusion protein through the use of a proteolytic enzyme and a cleavage site such as has been referred to above.

In another embodiment, a chimeric GDF8 peptide can be prepared, e.g., a glutathione-S-transferase (GST) fusion protein, a maltose-binding (MBP) protein fusion protein, or a poly-histidine-tagged fusion protein, for expression in any cell, or alternatively in a cell-free system. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the GDF8 peptide and the fusion partner (e.g., GST, MBP, FLAG®) as exemplified below, or poly-His as described above. Particular fusion proteins of the present invention include those comprising the TMV coat protein-GDF8 peptides that are exemplified below.

A "heterologous nucleotide sequence" as used herein is a nucleotide sequence that is added to a nucleotide sequence of the present invention by recombinant methods to form a nucleic acid that is not naturally formed in nature. Such nucleic acids can encode fusion (e.g., chimeric) proteins. Thus the heterologous nucleotide sequence can encode peptides and/or proteins that contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

A "host cell" is a cell that contains, or is capable of containing, and expressing, an exogenous nucleic acid molecule, either transiently or permanently. Exogenous nucleic acid (DNA or RNA) may or may not be integrated (covalently linked) into chromosomal DNA making up the genome of the cell. In prokaryotes and yeasts, for example, the exogenous nucleic acid may be maintained on an episomal element, such as a plasmid. With respect to eukaryotic cells, a stably transformed cell is one in which the exogenous nucleic acid has become integrated into the chromosome so that it is inherited by daughter cells through chromosome replication. This stability is demonstrated by the ability of the eukaryotic cell to establish cell lines or clones comprised of a population of daughter cells containing the exogenous nucleic acid. As exemplified herein, a "host cell" includes a eukaryotic plant cell that is infected with a recombinant tobamovirus. The exemplified tobamovirus vectors are TMV vectors, and are known to replicate only in the cytoplasm of infected Nicotiana plants, e.g. tocacco plants. The TMV vectors do not enter the nucleus, and do not stably transform the infected plant cell.

Prokaryotes include both gram negative and positive organisms, e.g., E. coli and B. subtilis. Higher eukaryotes include established tissue culture cell lines from animal cells, both of non-mammalian origin, e.g., insect cells, and birds, and mammalian origin, e.g., human, primates, and rodents, or plants, as exemplified below.

Prokaryotic host-vector systems include a wide variety of vectors for many different species. As used herein, Escherichia coli "E. coli," and its vectors, will be used generically to include equivalent vectors used in other prokaryotes. A representative vector for amplifying DNA is pBR322 or many of its derivatives. Vectors that can be used to express GDF8, and/or GDF8 peptides, include, but are not limited to, those containing the lac promoter (pUC-series); trp promoter (pBR322-trp); lpp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) Vectors: A Survey of Molecular Cloning Vectors and Their Uses, 1988, Buttersworth, Boston, pp. 205-236.

Yeast, as well as higher eukaryotic tissue culture cells can be used as hosts for the recombinant production of the inventive GDF8 peptides, and/or of anti-GDF8 antibodies and/or fragments of those antibodies. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include, for example, an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pCDNA1, pCD [Okayama et al., 1985, Mol. Cell Biol. 5:1136], pMC1neo Poly-A [Thomas et al., 1987, Cell 51:503], pUC19, pREP8, pSVSPORT and derivatives thereof, and baculovirus vectors, such as pAC 373 or pAC 610.

Prokaryotic expression control sequences typically used include promoters, including those derived from the β-lactamase and lactose promoter systems [Chang et al., 1977, Nature, 198:1056], the tryptophan (trp) promoter system [Goeddel et al., 1980, Nucleic Acids Res. 8:4057], the lambda $P_L$ promoter system [Shimatake et al., 1981, Nature, 292:128] and the tac promoter [De Boer et al., 1983, Proc. Natl. Acad. Sci. USA 292:128], all incorporated by reference herein. Numerous expression vectors containing such control sequences are known in the art and commercially available.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

General GDF8 Vector Design

The encoding nucleic acid sequence was preferably designed to be as divergent from the mammalian nucleic acid sequence as possible. For example, in one embodiment, the amino acid sequence of the precursor GDF8 was reverse-translated using yeast preferred codons. The resulting sequence was surveyed for codons that retained their homology to the human GDF8 nucleic acid sequence. Where possible these codons were substituted with the next most preferred yeast codons encoding the same amino acid.

The resulting optimized gene (SEQ ID NO: 3) can be expressed in any suitable host system, including, e.g., art-known insect, mammalian, bacterial, viral and yeast expression systems. For example, insect cell expression systems, such as baculovirus systems, are art-known and described, for instance, by Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well-known in the art and described, for example, by Sambrook et al. (*MOLECULAR CLONING: A LABORATORY MANUAL;* DNA Cloning, Vols. I and II; D. N. Glover ed.). Yeast expression systems are also known in the art and described, for example, by, *YEAST GENETIC ENGINEERING* (Barr et al., eds., 1989) Butterworths, London. Many other such expression systems are known to the art and are available commercially in kit form.

In one preferred embodiment, the modified precursor GDF8 gene (SEQ ID NO: 3) was expressed in a Flp-In™ CHO expression system (Invitrogen, Carlsbad, Calif.) as described in greater detail by Example 1, below.

More preferably, GDF8 peptides are expressed as part of fusion proteins in suitable plant viruses. Genetically altered plant viruses provide an efficient means of transfecting plants with genes encoding peptide-carrier fusion proteins. For example, a discussion of TMV coat protein fusions is provided by Turpen et al., 1999, U.S. Pat. No. 5,977,438. See also: Yusibov V. et al., 1997, *Proc. Natl. Acad. Sci. USA* 94:5784-5788; Modelska, A et al., 1998 *Proc. Natl. Acad. Sci. USA* 95:2481-2485, all of which are incorporated by reference herein.

Thus, the invention also provides novel recombinant plant viruses that include in their genetic material nucleotide sequences that encode plant viral coat protein ("VCP") and a GDF8 peptide, as discussed supra. The encoded fusion proteins are described herein as GDF8-VCP fusion proteins. The recombinant plant viruses permit systemic expression of the fusion protein in an infected plant. Thus, by employing these recombinant plant viruses, large quantities of GDF8-VCP fusion proteins may be produced. Optionally, the fusion proteins are engineered so that GDF8 peptides are readily cleaved from the fusion proteins and separated.

The location (or locations) in the VCP where the GDF8 peptide is joined (fused) to the VCP is referred to herein as the "fusion joint." A given fusion protein may have one or two fusion joints. The fusion joint may be located at the C-terminus of the VCP where it is fused to the N-terminus of the peptide of interest. The fusion joint may be located at the N-terminus of the VCP where it is fused to the C-terminus of the GDF8 peptide. In other embodiments of the invention, the GDF8 peptide is located internally within the VCP; in this case, the fusion protein will have two fusion joints. This is termed an internal fusion protein. Internal fusion proteins may comprise an entire plant VCP or a fragment thereof that is "interrupted" by the GDF8 peptide.

The fusion joints may be located at a variety of sites within a coat protein. The entire peptide may lie in the N-terminal portion or the C-terminal portion of the VCP. Suitable sites for the fusion joints may be determined either through routine systematic variation, testing the resultant internal fusion protein for the desired properties. Suitable sites for the fusion joints may also be determined by inspection of the three-dimensional structure of the coat protein to determine sites for "insertion" of the peptide that will not significantly interfere with the structural and biological functions of the VCP portion of the fusion protein. Detailed three-dimensional structures of plant VCPs and their orientation in the virus have been determined and are publicly available to a person of ordinary skill in the art. For example, a resolution model of the coat protein of Cucumber Green Mottle Mosaic Virus (a coat protein bearing strong structural similarities to other tobamovirus coat proteins) and the virus can be found in Wang and Stubbs, 1994, *J. Mol. Biol.* 239:371-384. Detailed structural information of TMV can be found, among other places, in Namba et al., 1989, *J. Mol. Biol.* 208:307-325 and Pattanayok and Stubbs, 1992, *J. Mol. Biol.* 228:516-528.

Knowledge of the three-dimensional structure of a plant virus particle and the assembly process of the virus particle permits the person of ordinary skill in the art to design various GDF8-VCP fusions of the invention, including insertions, and partial substitutions. For example, if the GDF8 peptide is hydrophilic, it may be appropriate to fuse the peptide to the TMV coat protein (TMVCP) region known to be oriented as a surface loop region. Likewise, a helical segments that maintain subunit contacts might be substituted for appropriate regions of the TMVCP helices or nucleic acid binding domains expressed in the region of the TMVCP oriented towards the genome.

Polynucleotide sequences encoding the GDF8-VCP fusion protein may comprise a "leaky" stop codon at a fusion joint. The stop codon may be present as the codon immediately adjacent to the fusion joint, or may be located close (e.g., within 9 bases) of the codons encoding the fusion joint. The purpose for such a leaky stop codon is to maintain a desired ratio of fusion protein to wild type coat protein. A "leaky" stop codon does not always result in translational termination and is periodically translated. The frequency of initiation or termination at a given start/stop codon is context dependent. The ribosome scans from the 5'-end of a mRNA for the first ATG codon. If it is in a non-optimal sequence context, the ribosome will pass, at a certain frequency, to the next available start codon and initiate translation downstream of the first. Similarly, the first termination codon encountered during translation will not always function if it is in a particular sequence context.

Consequently, many naturally occurring proteins exist as a population having heterogeneous N and/or C terminal extensions. By including a leaky stop codon at a fusion joint coding region in a recombinant viral vector encoding a GDF8-VCP fusion protein, the vector may be used to produce both the longer fusion protein and a second shorter protein, e.g., the VCP itself. A leaky stop codon may be used at, or proximal to, the fusion joints of fusion proteins in which the peptide of interest portion is joined to the C-terminus of the coat protein region, whereby a single recombinant viral vector could produce both GDF8-VCP fusion proteins and VCPs. Additionally, a leaky start codon may be used at or near the fusion joints to obtain a similar result. In the case of TMVCP, extensions at the N and C-terminus are localized to the surface of viral particles and can be expected to project away from the helical axis. An example of a leaky stop sequence occurs at the junction of the 126/183 kDa reading frames of TMV as was described years ago [Pelham, H. R. B., 1978, *Nature* 272:469471. Skuzeski, J. M. et al., 1991, *J. Mol. Biol.* 20:365-373, defined necessary 3' context requirements of this region to confer leakiness of termination on a heterologous protein marker gene (beta-glucuronidase) as CAR-YYA (R=purine; Y=pyrimidine)].

In another embodiment of the invention, the fusion joints on the GDF8-VCP fusion proteins are designed to be cleavable by having an amino acid sequence that is a substrate for a protease. This permits separation and isolation of the GDF8 peptide by using a suitable proteolytic enzyme. The proteolytic enzyme may contact the fusion protein either in vitro or in vivo.

The expression of the GDF8-VCP fusion protein may be driven by any of a variety of promoters functional in the context of the recombinant plant viral vector and host plant. In a preferred embodiment plant viral subgenomic promoters are used (See, e.g., U.S. Pat. No. 5,316,931, incorporated by reference herein).

Recombinant technologies have allowed the life cycle of numerous plant RNA viruses to be extended artificially through a DNA phase that facilitates manipulation of the viral genome. These techniques may be applied by the person of ordinary skill in the art in order make and use recombinant plant viruses of the invention. The entire cDNA of the TMV genome was cloned and functionally joined to a bacterial promoter in an *E. coli* plasmid (Dawson, W. O. et al., 1986, *Proc. Natl. Acad. Sci. USA* 83:1832-1836). Infectious recombinant plant viral RNA transcripts may also be produced using other well-known techniques, for example, commercially available RNA polymerases from T7, T3 or SP6. Precise replicas of the virion RNA can be produced in vitro with RNA polymerase and dinucleotide cap, m7GpppG. This not only allows manipulation of the viral genome for reverse genetics, but it also allows manipulation of the virus into a vector to express foreign genes. A method of producing plant RNA virus vectors based by manipulating RNA fragments with RNA ligase has been described (Pelcher, L. E. et al., 1982, EP 67553A2). Detailed information on how to make and use recombinant RNA plant viruses can be found, among other places in U.S. Pat. No. 5,316,931 (Donson et al.), which is herein incorporated by reference. The invention provides nucleic acids that comprise a recombinant RNA plant vector for expression of the GDF8-VCP fusion proteins. The invention also provides for nucleic acids that comprise a portion or portions of the vectors encoding the GDF8-VCP fusion proteins. The vectors described in U.S. Pat. No. 5,316,931, incorporated by reference herein, are particularly preferred for expressing the fusion proteins of the invention.

The plant VCP portion may be derived from the same virus from which the genome of the expression vector is derived. That is, the coat protein is optionally native with respect to the recombinant viral genome. Alternatively, the coat protein fusion partner may be heterologous, that is, non-native, in that it is derived from a virus different from the virus that contributes the recombinant viral genome. In a preferred embodiment, the 17.5 kDa coat protein of TMV is used in conjunction with a TMV-derived vector.

The peptide/polypeptide of interest in the protein may consist of any GDF8 peptide domain as defined herein, provided that the GDF8 peptide domain does not significantly interfere with an intended: (i) ability of the fusion protein to bind to a receptor molecule, including to antibodies and T cell receptors; (ii) ability to induce an immune response; and/or (iii) any of the biological activity which may be required of the fusion protein, including hormonal activity, immunoregulatory activity, as a substrate for an enzyme, or metal chelating activity, just to name a few.

In particular, the GENEWARE® system, available from the Large Scale Biology Corporation ("LSBC") based on the TMV was employed. See, e.g., Pogue, et al. 2002, *Ann Rev Phytopathol* 40: 45-74, incorporated by reference herein. TMV has a plus sense single stranded RNA genome of approximately 6400 nucleotides. The viral proteins involved in RNA replication are directly transcribed from the genomic RNA, whereas expression of internal genes is through the production of subgenomic RNAs. The production of subgenomic RNAs is controlled by sequences in the TMV genome which function as subgenomic promoters. The VCP is translated from a subgenomic RNA and is the most abundant protein and RNA produced in the infected cell (overview provided by FIG. 3). In a TMV-infected plant there are several milligrams of VCP produced per gram of infected tissue. GENEWARE® expression vectors take advantage of both the strength and duration of this promoter's activity to reprogram the translational priorities of the plant host cells so that virus-encoded proteins are synthesized at high levels, similar to the TMV VCP.

Full-length cDNA copies of the TMV RNA genome under the control of the T7 RNA polymerase promoter were constructed in an *Escherichia coli* compatible plasmid. Manipulations to the virus cDNA were performed using standard recombinant DNA procedures and the recombinant DNA transcribed in vitro with T7 RNA polymerase to generate infectious RNA (overview provided by FIG. 4). The infectious transcripts were used to infect various tobacco-related species (genus *Nicotiana*), including *tabacum, benthamiana* and the LSBC-created *Nicotiana excelsiana* species (Fitzmaurice, W. P., 2002. U.S. Pat. No. 6,344,597, incorporated by reference herein) via wounds induced by an abrasive. The TMV replicates in the initial cell, moves to adjacent cells to produce round infection foci and then enters the plants vascular system for transport to aerial leaves. There it systematically infects the majority of cells in each infected leaf. The foreign gene is expressed in all cells that express other virus protein products, including the replicase, movement protein and coat protein. The foreign protein is deposited in the site dictated by its protein sequence. Cytosolic proteins accumulate in the plant cytosol (such as the green fluorescent protein; GFP); secreted proteins accumulate in the plant ER, vacuolar compartments or apoplast depending on specific protein targeting sequences that are present within the foreign protein or added through genetic engineering. This system allows not only manipulation of the viral genome for reverse genetics, but also manipulation of the virus by standard recombinant DNA methods.

GENEWARE® vectors allow expression of foreign proteins or peptides by two distinct methods: 1) Independent gene expression: by adding a foreign gene for expression in place of the virus coat protein so it will be expressed from the endogenous virus coat protein promoter. A second coat protein promoter of lesser transcriptional activity and non-identity in sequence is placed downstream of the heterologous coding region and a virus coat protein gene is then added. This encodes a third subgenomic RNA allowing the virus vector to express all requisite genes for virus replication and systemic movement in addition to the heterologous gene intended for overexpression. 2) Display of immunogenic peptides on the surface of virus particles: The TMV virion is a rigid rod of ~18 nm diameter and 300 nm length. The structure of the virion and coat protein has been determined by X-ray diffraction revealing a structure of approximately 2,130 coat protein subunits arranged in a right-handed helix encapsidating the genomic RNA, with 16.3 subunits per turn.

This invention also provides virus particles, or virions, that include the GDF8-VCP fusion proteins. For example, the coat of the virus particles of the invention may consist entirely of GDF8-VCP fusion protein. In another embodiment, the virus particle consists of a mixture of GDF8-VCP fusion proteins and non-fused VCP, wherein the ratio of the two proteins may vary. As tobamovirus coat proteins may self-assemble into virus particles, the virus particles of the invention may be assembled either in vivo or in vitro. The virus particles may also be conveniently disassembled using well-known techniques so as to simplify the purification of the GDF8-VCP fusion proteins, or portions thereof.

The invention also provides recombinant plant cells comprising the GDF8-VCP fusion proteins and/or virus particles comprising the GDF8-VCP fusion proteins. These plant cells may be produced either by infecting plant cells (in culture or in whole plants) with the infectious recombinant virus particles of the invention or with polynucleotides comprising the genomes of the infectious virus particle of the invention. The recombinant plant cells of the invention have many uses, chief among which is serving as a source for the fusion coat proteins of the invention.

Optionally, the inventive vectors are codon-optimized for the codon usage of the selected host organism, e.g. plants of the genus *Nicotiana*.

Anti-GDF8 and Anti-VCP-GDF8 Antibodies

The methods of the invention included a process of screening GDF8-VCP fusion proteins and/or GDF8 peptides against a polyclonal anti-GDF8 antiserum. This process was employed to identify several epitopes of GDF8 that anti-GDF8 antibodies will specifically bind. In one embodiment, anti-GDF8 antiserum was obtained by immunizing an animal with precursor GDF8. The precursor GDF8 gene was modified to provide a form optimized for expression and immunigenicity. For example, the natural DNA sequence of the GDF8 prohormone (SEQ ID NO: 2) was optimized for expression in mammalian and viral expression systems. In addition, changes were made to avoid the negative effects of viral host shutoff mechanisms. Typically viral host shutoff mechanisms involve transcriptional control, RNA stability (splicing) and such. These changes made the nucleic acid less host like and more virus like.

The invention also includes polyclonal and monoclonal (mAb) antibodies that specifically bind to the inventive GDF8-VCP fusion proteins and/or to GDF8 and peptide fragments thereof. As used herein, the term "antibody" refers to an immunoglobulin and/or fragments thereof. A naturally occurring immunoglobulin consists of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. An antibody or antibodies according to the invention also encompass antibody fragments, i.e., antigen-binding fragments, for example, Fv, Fab, and F(ab')$_2$, engineered single-chain binding proteins, (e.g., Huston et al., 1988, *Proc. Natl. Acad. Sci. U.S.A.*, 85, 5879-5883, and Bird et al., *Science*, 1988, 242, 423-426, hereby incorporated herein by reference in its entireties), as well as bifunctional hybrid antibodies (e.g., Lanzavecchia et al., 1987, *Eur. J. Immunol.* 17, 105). [See, generally, Hood et al., 1984, Immunology, Benjamin, N.Y., 2nd ed., Harlow and Lane, *Antibodies. A Laboratory Manual*, Cold Spring Harbor Laboratory (1988) and Hunkapiller and Hood, 1986, *Nature*, 323, 15-16, all of the foregoing are incorporated by reference herein.]

For example, serum produced from animals immunized by the inventive GDF8-VCP fusion proteins and/or GDF8 peptides, using standard methods, can be used directly, or the IgG fraction can be separated from the serum using standard methods, such as plasmaphoresis or adsorption chromatography with IgG-specific adsorbents, such as immobilized Protein A or Protein G. Alternatively, monoclonal antibodies can be prepared, and optionally, antigen binding fragments or recombinant binding proteins derived from such mAbs. Such mAbs or fragments thereof can optionally be humanized by art-known methods.

Hybridomas producing mAbs that selectively bind the GDF8-VCP fusion proteins and/or GDF8 peptides of the invention, are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well-known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well-known in the art, and, in general, involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbant assay), RIA (radioimmunoassay) or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well-known phage library systems. See, e.g., Huse, et al., 1989, *Science* 246: 1275; Ward, et al., 1989, *Nature*, 341:544.

Antibodies thus produced, whether polyclonal or monoclonal, can be used, e.g., in an immobilized form bound to a solid support by well-known methods to purify the GDF8 peptides by immunoaffinity chromatography.

Antibodies that bind to the GDF8-VCP fusion proteins and/or GDF8 peptides can also be used, unlabeled or labeled by standard methods, as the basis for immunoassays to detect or quantify proteins or peptides comprising GDF8 epitopes, e.g., native GDF8 protein, GDF8-VCP fusion proteins and/or GDF8 peptides. The particular label used will depend upon the type of immunoassay. Examples of labels that can be used include, but are not limited to, radiolabels, such as $^{32}P$, $^{125}I$, $^{3}H$ and $^{14}C$; fluorescent labels, such as fluorescein and its derivatives, rhodamine and its derivatives, dansyl and umbelliferone; chemiluminescers, such as luciferia and 2,3-dihydrophthalazinediones; and enzymes, such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well-known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing GDF8-related polypeptides in expression cloning systems.

Neutralizing antibodies specific for the ligand-binding site of a receptor can also be used as antagonists (inhibitors) to block or downregulate GDF8 function. Such neutralizing antibodies can readily be identified through routine experimentation, as exemplified by the Examples provided below.

Antagonism of GDF8 activity in vivo or in vitro can be accomplished using complete antibody molecules, or well-known antigen binding fragments such as Fab, Fc, F(ab)$_2$, and Fv fragments. Definitions of such fragments can be found as described hereinabove, or e.g., in Klein, *Immunology* (John Wiley, New York, 1982); Parham, Chapter 14, in Weir, ed. *Immunochemistry,* 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., 1973, Biochemistry 12:1130; Sharon et al., 1976, Biochemistry 15:1591; Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun, 1991, *Bio/Technology* 9:545. Alternatively, they can be chemically synthesized by standard methods.

The present invention also encompasses anti-idiotypic antibodies, both polyclonal and monoclonal, which are produced using the above-described antibodies as antigens. These antibodies are useful because they may mimic the structures of the ligands.

Vaccine Compositions and Administration

In a preferred embodiment, the virions expressing GDF8-VCP fusion proteins, the GDF8-VCP fusion proteins, and/or GDF8 peptides derived therefrom, are incorporated into any suitable vaccine composition. Such vaccine compositions are well-known to the art and include, for example, physiologically compatible buffers and saline and the like, as well as adjuvants, as described in greater detail hereinbelow. The provided vaccine composition is employed, for example, for eliciting antiserum for screening and identifying a specific neutralization epitope for an anti-GDF8 antibody.

As exemplified herein, purified precursor GDF8 protein expressed by a vector comprising SEQ ID NO: 3 was injected into a goat in a vaccine composition that included one half mg of precursor GDF8 protein emulsified into Freund's complete adjuvant (CFA). The vaccine composition was preferably injected subcutaneously (SC) beneath the skin of the goat. Subsequent booster immunizations are preferred. These can be administered at suitable additional intervals with the same or a reduced dosage of the protein, e.g., at intervals ranging from 2-5 weeks after the initial injection.

Beginning from about two weeks after the initial injection, but preferably starting after a longer time period, e.g., from three to fifteen weeks, or longer, serum is collected, as needed, from the immunized animal. The collected serum is then preferably purified and/or fractionated by conventional immunoglobulin purification procedures such as, for example, protein A-Sepharose, protein G-agarose, hydroxylapatite chromatography, gel electrophoresis, dialysis, or affinity chromatography with a suitable ligand. As exemplified herein, the IgG fraction of the serum was further fractionated on a protein G-agarose column.

The anti-GDF8 antiserum IgG fraction is then available for screening against a range of peptides of the mature GDF8, as described in greater detail by Example 3, hereinbelow.

In one preferred embodiment, the vaccine comprises an intact plant virus expressing the GDF8-VCP fusion protein as an immunogen, e.g., suspended in a suitable physiological composition. In another preferred embodiment, the vaccine comprises the VCP protein substantially isolated from the virion and optionally including one or more art-known adjuvants. In a further preferred embodiment, the vaccine composition comprises one or more GDF8 peptides, together with suitable adjuvants. In still a further embodiment, the vaccine composition comprises combinations of the foregoing.

The vaccine composition includes a sufficient amount of the desired immunogen, such as the GDF8-VCP fusion protein, to elicit an immune response. The amount administered per dose can range from about 1 microgram/kg to about 1.0 g/kg, relative to the mass of the animal.

When the immunization is intended to elicit polyclonal antibodies or activated lymphocytes (for further screening and hybridization) any suitable vertebrate animal is readily employed. Preferably, the animal is a mammal, and includes, but is not limited to, rodents, such as a mice, rats, rabbits, horses, canines, felines, bovines, porcines, e.g., pigs and hogs, ovines, e.g., goats and sheep, primates, e.g., monkeys, great apes and humans, and the like.

"Adjuvants" are agents that nonspecifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate and alum; surfactants, such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions, such as pyran, dextran sulfate, poly IC, polyacrylic acid and carbopol; peptides, such as muramyl dipeptide, dimethylglycine and tuftsin; and oil emulsions. The protein or peptides could also be administered following incorporation into liposomes or other microcarriers. Information concerning adjuvants and various aspects of immunoassays are disclosed, e.g., in the series by P. Tijssen, *Practice and Theory of Enzyme Immunoassays,* 3rd Edition, 1987, Elsevier, N.Y., incorporated by reference herein.

When the GDF8-VCP fusion proteins of the invention, fragments thereof or viral particles expressing the GDF8-VCP proteins or fragments are to be administered in vivo, they are typically given as a pharmaceutical composition that includes a pharmaceutically acceptable carrier or excipient. Such as carrier can be any compatible, non-toxic substance suitable for delivery of the desired compounds to the body. Sterile water, alcohol, fats, waxes and inert solids may be included in the carrier. Pharmaceutically accepted buffering agents, dispersing agents, etc. may also be incorporated into the pharmaceutical composition. Additionally, when fusion proteins or fragments are used to induce immune responses (protective or otherwise), the formulation may comprise one or more immunological adjuvants in order to stimulate a more potent desired immune response.

Any of a number of routes of administration may be used when giving the compositions to an animal, including a human. Standard routes of administration include, e.g., intravenously, intramuscularly, subcutaneously, intradermally, intraperitoneally, and/or orally. For fish species, methods of administering a vaccine composition or immunogenic composition include the foregoing, as well as dipping the fish into water comprising an antigenic concentration of the peptide, spraying the fish with an antigenic concentration of the peptide while the fish is briefly separated from the water, etc. The artisan will appreciate that the vaccine composition is preferably formulated appropriately for each type of recipient animal and route of administration. Compositions for parenteral administration comprise a solution of the fusion protein (or derivative) or a cocktail thereof dissolved in an acceptable carrier, preferably an aqueous carrier, e.g., water, buffered water, 0.4% saline, buffered saline, 0.3% glycerine and the like. These solutions are sterile and generally free of particulate matter. These compositions may be sterilized by conventional sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc.

The concentration of GDF8 peptide and/or GDF8-VCP fusion protein (or portions thereof) in these formulations can vary widely depending on the specific amino acid sequence and the desired biological activity, e.g., from less than about 0.5%, usually at least about 1% to as much as 15 or 20% by weight and will be selected primarily based on fluid volumes, viscosities, etc., in accordance with the particular mode of administration selected and the condition of the recipient.

Actual methods for preparing parenterally administrable compositions and adjustments necessary for administration to subjects are known or apparent to those skilled in the art and are described in more detail in, for example, Remington's Pharmaceutical Science, current edition, Mack Publishing Company, Easton, Pa., which is incorporated by reference herein.

Identification of GDF8 Binding Epitopes

Suitable anti-GDF8 monoclonal or polyclonal antibodies were contacted with GDF8 protein for a time period sufficient for the antibody to bind selectively to the protein. Thereafter, GDF8 bioassays confirmed that the antibody neutralized substantially all of the GDF8 protein activity. Any GDF8 bioassay can be employed for this purpose, although, as exemplified hereinbelow by Example 3, an in vitro transcriptional activation assay according to Thies et. al., 2001, (*Growth Factors* 18, 251) is preferred.

Generally, a GDF8 peptide useful as an antigen or binding epitope according to the invention includes from about residue 312 to about residue 361 of GDF8 (SEQ ID NO: 1). In particular, a peptide according to the invention includes from about residue 320 to about residue 350 of GDF8 (SEQ ID NO: 1). The peptide preferably includes from about residue 321 to about residue 346 of GDF8 (SEQ ID NO: 1).

The artisan will appreciate that the inventive GDF8 peptide can be readily modified to include at least one conservative amino acid substitution at any position, provided that the polypeptide specifically binds to rat monoclonal antibody MAB788, as exemplified hereinbelow. Such conservative substitutions can include, for example, variations at residues 328, 329 and 335, and combinations thereof, wherein, amino acid residue 328 is His, Leu, Asn or Val; amino acid residue 329 is Lys or Leu; and amino acid residue 335 is Ser or Pro or Thr. Precursor GDF8 residues 328, 329 and 335 vary within the GDF8 protein sequence across species, as illustrated by FIG. 2, but nevertheless, the mature GDF8 remains functional.

FIG. 1 illustrates a map of the GDF8 active region (that forms the mature protein) in the context of its precursor protein. Superimposed on the map of the GDF8 active region are the locations of seven overlapping peptides. These overlapping peptides were designed in order to provide targets for identifying the antibody-binding epitope or epitopes of GDF8. The peptide labeled as DJ5 was identified by screening with the IgG fraction of the exemplified goat anti-GDF8 antiserum as the only significant binding epitope of GDF8 for the exemplified antiserum. This peptide has a sequence (SEQ ID NO: 8) corresponding to residue 321 to residue 346 of precursor GDF8 (SEQ ID NO: 1).

Animals to be Treated and/or Immunized

The result of successful immunization that elicits GDF8 neutralizing antibody will be downregulation of GDF8 function in the immunized animal. In one preferred embodiment, the animal is a "food-producing" animal, and the result of active or passive immunization is a gain in animal weight, particularly muscle mass, relative to animals not immunized. Passive immunization can be performed, e.g., by treating an animal with a neutralizing anti-GDF8 antibody and/or antibody fragment thereof.

In another preferred embodiment, the animal is a human or other animal, e.g., a pet or companion animal, wherein GDF8 function is downregulated by active or passive immunization. In this optional alternative embodiment, the purpose of the GDF8 downregulation is to provide medical or veterinary treatment, e.g. to counteract a muscle wasting condition, and/or for research purposes in an animal not raised for food purposes. In an optional alternative preferred embodiment, the animals to be treated for veterinary purposes include all animals that will benefit from such treatment, e.g., as enumerated above, but specifically excluding humans.

The animal is preferably a vertebrate, and more preferably a mammal, avian or piscine. It should be recognized the definition of a food animal will vary among people of different cultures. In addition, food animals not normally employed for human consumption, e.g., in the United States, may be employed as food animals to feed other animals, such as pets, exotic pets, companion animals and/or research animals.

Thus, the following list is not intended to be limiting, but is provided simply by way of example In one particular embodiment, the animal subject is a mammal. Other mammalian subjects include nonhuman primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, antelopes, rabbits, and rodents (e.g., guinea pigs, squirrels, rats, mice, gerbils, and hamsters). Avians include *Anatidae* (swans, ducks and geese), *Columbidae* (e.g., doves and pigeons), *Phasianidae* (e.g., partridges, grouse and turkeys) *Thesienidae* (e.g., domestic chickens), *Psittacines* (e.g., parakeets, macaws, and parrots), game birds, and ratites, (e.g., ostriches).

Birds can be associated with either commercial or noncommercial aviculture. These include e.g., *Anatidae*, such as geese and ducks, *Columbidae*, e.g., doves and pigeons, including domestic pigeons, *Phasianidae*, e.g., partridge, grouse and turkeys, *Thesienidae*, e.g., domestic chickens.

Other food animals include, for example, marsupials (such as kangaroos), reptiles (such as farmed turtles) and other economically important domestic animals for which the inventive methods are safe and effective in enhancing weight and/or promoting muscle growth.

For purposes of the present invention, the term "piscine" or "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp).

| Salmonidae Family | |
| --- | --- |
| TAXON NAME | COMMON NAME |
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus leucomaenis* | Japanese charr (white spotted charr) |
| *Salvelinus malma* | Dolly varden (Miyabe charr) |
| *Salvelinus namaycush* | Lake trout |
| *Thymallus thymallus* | Grayling |

| Some Members of the Serranidae Family | |
| --- | --- |
| TAXON NAME | COMMON NAME |
| *Centropristis ocyurus* | Bank sea bass |
| *Centropristis philadelphicus* | Rock sea bass |
| *Centropristis striata* | Black sea bass |
| *Diplectrum bivittatum* | Dwarf sandperch |
| *Diplectrum formosum* | Sand perch |
| *Epinephelus flavolimbatus* | Yellowedge grouper |
| *Epinephelus morio* | Red grouper |
| *Serranus phoebe* | Tattler |
| *Serranus tortugarum* | Chalk bass |

| Some Members of the Sparidae family | |
| --- | --- |
| TAXON NAME | COMMON NAME |
| *Archosargus probatocephalus* | Sheepshead |
| *Archosargus rhomboidalis* | Sea bream |
| *Calamus penna* | Sheepshead porgy |
| *Lagodon rhomboides* | Pinfish |
| *Pagrus Major* | Red Sea bream |
| *Sparus aurata* | Gilthead Sea bream |
| *Stenotomus chrysops* | Scup |

| Some Members of the Cichlidae family | |
| --- | --- |
| TAXON NAME | COMMON NAME |
| *Aequidens latifrons* | Blue acara |
| *Cichlisoma nigrofasciatum* | Congo cichlid |
| *Crenichichla* sp. | Pike cichlid |
| *Pterophyllum scalare* | Angel fish |
| *Tilapia mossambica* | Mozambique mouth breeder |
| *Oreochromis* spp | Tilapia |
| *Sarotherodon aurea* | Golden Tilapia |

| Some Members of the Centrarchidae family | |
| --- | --- |
| TAXON NAME | COMMON NAME |
| *Ambloplites rupestris* | Rock bass |
| *Centrarchus macropterus* | Flier |
| *Elassoma evergladei* | Everglades pigmy sunfish |
| *Elassoma okefenokee* | Okefenokee pigmy sunfish |
| *Elassoma zonatum* | Banded pigmy sunfish |
| *Enneacanthus gloriosus* | Bluespotted sunfish |
| *Enneacanthus obesus* | Banded sunfish |
| *Lepomis auritus* | Redbreast sunfish |
| *Lepomis cyanellus* | Green sunfish |
| *Lepomis cyanellus* X *L. gibbosus* | Green x pumpkinseed |
| *Lepomis gibbosus* | Pumpkinseed |
| *Lepomis gulosus* | Warmouth |
| *Lepomis humilis* | Orange-spotted sunfish |
| *Lepomis macrochirus* | Bluegill |
| *Lepomis megalotis* | Longear sunfish |
| *Micropterus coosae* | Shoal bass |
| *Micropterus dolomieui* | Smallmouth bass |
| *Micropterus punctulatus* | Spotted bass |
| *Micropterus salmoides* | Largemouth bass |
| *Pomoxis annularis* | White crappie |
| *Pomoxis nigromaculatus* | Black crappie |

In a further embodiment, the animal is a companion animal or a human, and the vaccine is administered to provide long-term downregulation of GDF8 for any veterinary or medical purpose responsive to such GDF8 downregulation. For purposes of the present invention, the term "companion" animal shall be understood to include: horses (equine), cats (feline), dogs (canine), rodents, (including mice, rats, guinea pigs) rabbit species, and avians, such as pigeons, parrots and the like.

Birds receiving such vaccination or antibodies can be associated with either commercial or noncommercial aviculture. These include e.g., *Anatidae*, such as swans, geese, and ducks, *Columbidae*, e.g., doves and pigeons, such as domestic pigeons, *Phasianidae*, e.g., partridge, grouse and turkeys, Thesienidae, e.g., domestic chickens, *Psittacines*, e.g., parakeets, macaws, and parrots, e.g., raised for the pet or collector market.

In another preferred embodiment, any of the above recited animals (preferably nonhuman) are immunized in order to obtain anti-GDF8 antibodies that specifically bind to the inventive peptides, and the elicited antibodies are harvested for use in assays, and/or in veterinary or human medicine, e.g., to provide downregulation of GDF8 for any veterinary or medical purpose responsive to such GDF8 downregulation.

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Materials & Methods

A. Expression and Purification of Precursor GDF8 (GDF8 Prohormone)

The natural DNA sequence of the precursor GDF8 or prohormone (SEQ ID NO: 2) was optimized for expression in mammalian and viral expression systems. To avoid the negative effects of viral host shutoff mechanisms the DNA sequence was designed to be as divergent from the mammalian nucleic acid sequence as possible. To accomplish this the amino acid sequence of the GDF8 prohormone was reversed translated using yeast preferred codons. The resulting sequence was surveyed for codons, which retained their homology to the human GDF8 nucleic acid sequence. Where possible these codons were substituted with the next most preferred yeast codons encoding the same amino acid. The resulting nucleic acid molecule (SEQ ID NO: 3) was commercially synthesized for incorporation into the appropriate expression vectors.

The Flp-In™ CHO expression system (Invitrogen, Carlsbad, Calif.) was used to express the optimized GDF8 prohormone. Briefly, a GDF8 prohormone construct containing a C-terminal FLAG® (Sigma-Aldrich Corp., St. Louis, Mo.) epitope fusion was constructed by inserting the gene encoding the modified GDF8 prohormone into plasmid pCMVtag4B (Stratagene, San Diego, Calif.). The FLAG® fusion tag facilitates separation of FLAG® fusion proteins on an anti-FLAG® gel column. A PCR DNA fragment containing the modified GDF8 prohormone-FLAG® gene was then cloned into plasmid expression vector pcDNA5/FRT (Invitrogen, Carlsbad, Calif.). Generation of the Flp-In™ CHO cell line expressing the GDF8 prohormone-FLAG® fusion protein was achieved by cotransfection of the Flp-In™ CHO cell line with the Flp-In™ expression vector containing the GDF8-FLAG® gene and the Flp recombinase expression plasmid, POG44. Flp recombinase mediates insertion of the Flp-In expression cassette into the genome at an integrated FRT site by site-specific DNA recombination. A stable cell line expressing and secreting the GDF8 prohormone containing the FLAG® epitope was obtained using hygromycin B selection.

The stable CHO cell line expressing the GDF8 prohormone containing the FLAG® tag was adapted to suspension culture in serum-free media using standard techniques. Conditioned media containing the secreted GDF8 prohormone was generated using the WAVE bioreactor system (WAVE Biotech LLC, Bridgewater, N.J.). Purification of the FLAG® tagged GDF8 prohormone was achieved by affinity chromatography using an anti-FLAG® M2 affinity gel (Sigma-Aldrich Corp., St. Louis, Mo.).

B. DJ5 Specific Antibody Purification

DJ5 (SEQ ID NO: 8; See Table 2, below) specific antibody fractions were purified by affinity column chromatography. An affinity column was prepared by coupling 10 mg of DJ5 synthetic peptide to 0.8 g of cyanogen bromide-activated Sepharose 4B (Sigma Genosys, Woodlands, Tex.). The column was washed and equilibrated with PBS. Approximately 11 ml of Goat IgG fraction (10 mg/ml) was applied to the affinity column and washed with 25 ml of PBS. Fractions of 1.0 ml were collected and monitored for absorbance at 280 nm. Bound material was eluted with approximately 10 ml of 0.2 M glycine (pH 1.85). Fractions of 1.0 ml were collected and neutralized with 0.25 ml of 0.5 M sodium phosphate, 0.75 M NaCl, pH 7.4. Approximately 25 µl aliquots of unbound fractions 1-10 and bound fractions 25-35 were assayed for ELISA reactivity to DJ5 peptide. Unbound fractions were found to be negative for DJ5 reactivity. Bound fractions exhibited a strong peak of reactivity to the DJ5 peptide. Unbound fractions 1-11 and bound fractions 26-34 were pooled. Pooled samples were concentrated and their buffer exchanged with phosphate buffered saline (PBS) as indicated below. Sample concentrations were determined by the OD 280 method (*CURRENT PROTOCOLS IN IMMUNOLOGY,* 2.7.3, John Wiley & Sons, Inc.). The unbound sample was adjusted to 10 mg/ml and the bound sample was adjusted to 1 mg/ml, for subsequent use.

Example 2

Goat Anti-GDF8 Polyclonal IgG Serum

Goat anti-precursor GDF8 IgG was obtained from an immunized goat by the following methods:

A. Immunization of Goat

A Saanen (dairy) goat (approximately 2 year old male) was immunized with purified recombinant GDF8 prohormone (obtained as described by Example 1, above), as follows. One half mg of protein was emulsified in Freund's complete adjuvant (CFA) and injected subcutaneously (SC) beneath the skin of the goat. Subsequent booster immunizations administered SC at weeks three, six, and ten contained 0.3 mg of protein emulsified in Freund's incomplete adjuvant (IFA). Blood was collected from the jugular vein with a syringe and needle, and taken with vacuum bottle and tubing. The blood was collected in bottles containing anticoagulant and centrifuged at 2500 RPM for 20 minutes to remove the red blood cells. The plasma was re-calcified to produce serum. The serum sample collected 15 weeks post initial immunization was used for further analysis.

B. Collection and Purification of Goat Polyclonal IgG

Serum was harvested from the goat after 15 weeks, and the IgG fraction was purified from this serum, as follows. The IgG fraction of goat sera was purified on a Protein G agarose column according to the manufactures protocol (Kirkegaard and Perry Laboratories, Inc., Gaithersburg, Md.). Eluted fractions were pooled, concentrated, and buffer exchanged with phosphate buffered saline (PBS) utilizing Centriprep centrifugal Filters (Centriprep YM-10, Millipore Corporation, Billerica, Mass.). Sample concentrations were determined by the OD 280 method.

Example 3

Characterization of Goat Antiserum

The goat antiserum provided by Example 2, above, is designated as PGA. It is expected that the PGA IgG fraction contains antibodies directed against various epitopes on the GDF8 prohormone molecule. The PGA antiserum was characterized by an in vitro transcription activation assay, as follows. The in vitro transcriptional activation assay used to quantitatively measure GDF8 bio-neutralization is essentially that of Thies et. al. (*Growth Factors* 18, 251 (2001)). Ninety-six well tissue culture treated luminometer View-Plate™ assay plates (PerkinElmer Life and Analytical Sciences, Inc., Boston, Mass.) were seeded with $1.0 \times 10^5$ cells/well of A204 Rhabdomyosarcoma cells (ATCC HTB-82) and incubated in a 37° C., 5% $CO_2$, humidified chamber. Complete A204 culture media consists of McCoy's 5A medium, 10% fetal bovine serum, 2% L-glutamine, and 1% Penn/Strep. Upon reaching greater than 80% confluence, the cells were transiently transfected with a mixture of plasmid pDPC4-luciferase and HCMV IE-lacZ using the protocol recommended by the manufacturer of the FUGENE transfection reagent (Roche Diagnostics Corporation, Indianapolis, Ind.) and incubated 16 hours in a 37° C., 5% $CO_2$, humidified chamber. Plasmid pDPC4-luciferase contains four copies of the CAGA box, derived from the human plasminogen activator inhibitor (PAI-1), which confers GDF8 responsiveness to the heterologous promoter reporter construct.

Plasmid HCMV IE-lacZ contains a beta-galactosidase gene under the control of the constitutive human cytomegalovirus immediate early promoter. This gene is added as a control to normalize for transfection efficiencies. Cells were then treated with 100 ng/well GDF8 protein (R&D Systems Inc., Minneapolis, Minn.) and incubated an additional 16 hours in a 37° C., 5% $CO_2$, humidified chamber. Luciferase and beta-galactosidase were quantified in the treated cells using the Dual-Light Luciferase Assay (Tropix, Applied Biosystems, Foster City, Calif.).

Each sample was run in duplicate (2 wells). The signal for each well was calculated as the luciferase signal divided by the beta-glactosidase signal times 100. The sample signal was calculated as the average of the two wells.

To test the bio-neutralization activity of an antibody sample various concentrations of purified IgG fractions were incubated with the GDF8 protein (approximately 16 hours at 4° C.) prior to treatment of the cells. The percent inhibition was calculated as 100−(100× sample signal)/(signal with GDF8 alone−signal with no GDF8 added). The results of the in vitro transcription activation assay are summarized by Table 1, below.

TABLE 1

| GDF8 neutralization titers for Goat Serum PGA | |
|---|---|
| Sample (μg IgG) | % Inhibition of GDF8 Activity |
| Goat - normal (250) | 0 |
| Goat - PGA (250) | 95 |
| Goat - PGA (125) | 86 |
| Goat - PGA (63) | 62 |
| Goat - PGA (31) | 22 |
| Goat - PGA (16) | 3 |

The neutralization assay confirmed that the IgG fraction of the harvested goat serum contains antibodies capable of neutralizing at least 95% of the GDF8 used in this activity assay.

Example 4

Goat Polyclonal Antibody Defines a Specific Neutralization Epitope of the GDF8 Protein In order to determine the specificity of the neutralizing immune response the PGA IgG fraction was assayed for its reactivity with a set of seven overlapping peptides (DJ1-7 see Table 2 and FIG. 1) that span the entire coding region of the active GDF8 protein. Reactivity of the Goat PGA IgG to each individual peptide was determined by Enzyme-Linked Immunosorbent Assay (ELISA) assay. The GDF8 peptide ELISA was performed essentially as described in Protein Detector™ ELISA Kit HRP, ABTS System (Kirkegaard and Perry Laboratories, Inc., Gaithersburg, Md.). The following modifications were used in the assay. Synthetic peptides DJ1-7 (see Table 2, below) were custom synthesized under our direction by ProSci, Inc. (Poway, Calif.). Plates were coated with synthetic peptides at 500 ng per well and purified GDF8 prohormone at 250 ng per well. Primary antibodies were IgG fractions from various samples. Secondary antibodies were used at a dilution of 1:2000. For goat primary antibody samples the secondary antibody was rabbit peroxidase-labeled antibody to goat IgG. For rat primary antibody samples the secondary antibody was goat peroxidase-labeled antibody to rat IgG. The OD 405 nm was read for 15 minutes with an ELISA plate reader. The ELISA reactivity was calculated as OD 405 per minute times 1000.

TABLE 2

| GDF8 Active Region Peptides | | | |
|---|---|---|---|
| Name | Coordinates* | Amino acid sequence | |
| DJ1 | 267-286 | DFGLDCDEHSTESRCCRYPL | SEQ ID NO:4 |
| DJ2 | 282-301 | CRYPLTVDFEAFGWDWIIAP | SEQ ID NO:5 |
| DJ3 | 297-316 | WIIAPKRYKANYCSGECEFV | SEQ ID NO:6 |

TABLE 2-continued

GDF8 Active Region Peptides

| Name | Coordinates* | Amino acid sequence | |
|---|---|---|---|
| DJ4 | 312-331 | ECEFVFLQKYPHTHLVHQAN | SEQ ID NO:7 |
| DJ5 | 327-346 | VHQANPRGSAGPCCTPTKMS | SEQ ID NO:8 |
| DJ6 | 342-361 | PTKMSPINMLYFNGKEQIIY | SEQ ID NO:9 |
| DJ7 | 357-375 | EQIIYGKIPAMVVDRCGCS | SEQ ID NO:10 |

*relative to Human GDF8 prohormone (Genebank Accession Number NP_005250)

The ELISA results are summarized by Table 3, below.

TABLE 3

ELISA reactivity of PGA IgG (10 mg/ml) to GDF8 Active Region Peptides

| | OD 405/ minute × 1000 | | |
|---|---|---|---|
| Antigen | 1:20 | 1:40 | 1:80 |
| DJ1* | 23 | 10 | 1 |
| DJ2* | 3 | 0 | 0 |
| DJ3* | 0 | 10 | 0 |
| DJ4* | 3 | 0 | 0 |
| DJ5* | 121 | 37 | 27 |
| DJ6* | 3 | 0 | 0 |
| DJ7* | 10 | 1 | 0 |
| proGDF8** | 194 | 196 | 199 |

*peptide,
**prohormone

The PGA IgG fraction reacted specifically with both the purified GDF8 prohormone and with the DJ5 peptide. Among the GDF8 active region peptides the IgG fraction reacts specifically and exclusively with the DJ5 peptide. This is a strong indication that the neutralizing capability of this serum is directed against an epitope defined by the DJ5 peptide. In order to confirm this hypothesis the DJ5 specific fraction of PGA IgG was purified. This was accomplished by affinity chromatography as described by Example 1, supra. The PGA antibodies were separated into DJ5 peptide bound and unbound fractions. Both fractions were assayed for neutralization activity against the GDF8 protein.

The results in Table 4, below, show that the majority of GDF8 neutralization capacity resides with the antibody that binds specifically to the DJ5 peptide. This clearly demonstrates that the DJ5 peptide defines a neutralizing epitope of the GDF8 protein.

TABLE 4

GDF8 neutralization activity of DJ5 specific antibodies

| Sample (μg IgG) | % Inhibition of GDF8 Activity |
|---|---|
| Goat - normal (250)** | 7 |
| DJ5 unbound IgG (250) | 26 |
| DJ5 bound IgG (25) | 90 |

**The normal goat IgG was a negative control purified from non-immunized goat sera (commercially purchased).

Curiously, in a preliminary experiment, neutralizing GDF8 antibodies were not obtained when two rabbits were injected with the human DJ5 antigen conjugated to keyhole limpet hemocyanin. As can be seen in FIG. 2, the amino acid sequences corresponding to DJ5 for rabbit and human GDF8 are identical, whereas the amino acid sequence of goat DJ5 is different. Therefore, in view of the data provided above for the goat, the preliminary rabbit data suggests that it may be advantageous to use a DJ5 antigen that comprises a different amino acid sequence than that for the corresponding region/portion of the host animal GDF8. Thus, in this case, the ability of the recombinant human GDF8 prohormone to induce bio-neutralizing antibodies in a goat may be due, at least in part, to the fact that the antigen used comprised an amino acid sequence that differs from that of the host sequence by a single amino acid substitution in the DJ5 region/portion of GDF8 [see, amino acid residue 333 in FIG. 2]. More particularly, as FIG. 2 shows, the $Arg_{333}$ in the human sequence is replaced by a $Lys_{333}$ residue in the goat sequence. This lone conservative amino acid substitution may constitute an alteration that is significant enough to render the protein "foreign" to the goat immunological surveillance system.

Example 5

GDF8 Neutralizing Rat mAB 788 Defines a Specific Neutralization Epitope of the GDF8 Protein Rat monoclonal antibody MAB788 is reported to neutralize mouse GDF8 bioactivity (R&D Systems Inc., Cat. No. MAB788, Minneapolis, Minn.). In order to confirm this result we assayed the monoclonal antibody for neutralization activity against the GDF8 protein. The antibody was characterized as described by Example 3, above. The results of this assay are summarized by Table 5, as follows.

TABLE 5

GDF8 neutralization titers for monoclonal antibody 788

| Sample (μg IgG) | % Inhibition of GDF8 Activity |
|---|---|
| MAB - 788 (12.5) | 47 |
| MAB - 788 (6.3) | 17 |
| MAB - 788 (3.1) | 7 |
| MAB - 788 (1.8) | 0 |
| MAB - 788 (0.1) | 0 |

Table 5 confirms that this antibody is capable of neutralizing the activity of the GDF8 protein. In order to determine the specificity of this neutralizing immune response the rat monoclonal antibody was assayed for its reactivity with a set of seven overlapping peptides (DJ1-7 see Table 2 and FIG. 1) that span the entire coding region of the active GDF8 protein.

Reactivity of the monoclonal antibody to each individual peptide was determined by ELISA assay (see Example 4, supra).

TABLE 6

ELISA reactivity of Rat MAB 788 (10 mg/ml) to GDF8 active region peptides

| | OD 405/ minute × 1000 | | |
|---|---|---|---|
| Antigen | 1:20 | 1:40 | 1:80 |
| DJ1* | 4 | 0 | 0 |
| DJ2* | 0 | 0 | 0 |
| DJ3* | 0 | 0 | 0 |
| DJ4* | 0 | 0 | 0 |
| DJ5* | 133 | 118 | 102 |
| DJ6* | 0 | 0 | 0 |
| DJ7* | 0 | 0 | 0 |
| proGDF8** | 132 | 127 | 132 |

*peptide,
**protein

The rat monoclonal antibody reacted specifically with both the purified GDF8 prohormone and with the DJ5 peptide. Typically a monoclonal antibody has mono specificity to a single epitope. Among the GDF8 active region peptides this monoclonal antibody reacts specifically and exclusively with the DJ5 peptide. This result provides further independent evidence that the DJ5 peptide defines a neutralizing epitope of the GDF8 protein.

Example 6

Construction of Vectors for Inserting Epitopes into the Coat Protein Through Oligonucleotide Annealing The cloning of different epitopes into different locations of the TMV coat protein was simplified by creating five different acceptor vectors (FIG. 5). Table 7 lists these vectors along with their properties. These vectors contain the NcoI (5') and NgoMIV (3') restriction sites that were placed at the appropriate location of the coat protein open reading frame (ORF) for the TMV U1 or U5 strain. For the TMV U1 strain, the restriction site pair was placed at the N-terminal Loop, between amino acids 155 and 156 (GPAT) and at the C-terminus, while for the U5 strain it was only placed between amino acids 155 and 156 (TPAT). Any pair of oligonucleotides coding for a peptide, having the 5' and 3' overhangs of "CATG" and "CCGG", respectively, can easily be cloned into these acceptor vectors. The construction of three of these vectors, pLSB2268, pLSB2269, and pLSB2109 was described by Palmer et al. (April 2004; world patent publication no. WO 2004/032622 A2). The construction of the remaining two vectors, pLSB2110 and pLSB1806, is described below.

TABLE 7

Characteristics of Acceptor Vectors For Inserting DJ5 Epitopes Into TMV Coat Protein

| Plasmid name | Insert location | Source of coat protein | Added non-native sequence | SEQ ID |
|---|---|---|---|---|
| pLSB2268 | N-terminal | U1 | -----AG | * |
| pLSB2269 | Loop | U1 | GSPM-----AGPSG | (residues 64-93 of SEQ ID NO: 50) |
| pLSB2109 | Before the last 4 amino acids (GPAT) | U1 | AM-----A | * |
| pLSB2110 | C-terminal | U1 | AM-----AG | |
| pLSB1806 | Before the last 4 amino acids (TPAT) | U5 | AM-----AG | |

*More detailed information on this vector is available in Palmer et al. (April 2004, WO 2004/032622 A2, incorporated by reference herein). The nucleic acid sequences for pLSB2110 and pLSB1806 are for the coat protein open reading frame.
"-----" The dashed lines indicate the GDF8 peptide domain of interest, e.g., DJ5, that is inserted into the respective acceptor vector. The additional non-native sequence is due to the amino acids generated at the insertion site.

To generate pLSB2110, a 0.8 kilobase (kb) fragment of DNA was amplified from plasmid pLSB2108, a derivative of PBTI 2150 (Pogue et al, 2004; U.S. Pat. No. 6,730,306 B1) where the AflIII restriction site was removed, using the following primers:

```
                                            (SEQ ID NO:37)
GCGCACATGTCTTACAGTATCACTAC;

(SEQ ID NO:38)
TGGTCCTGCAACTGCCATGGACAGTGCCGGCTGAGGTAGTCAAGAT;

(SEQ ID NO:39)
CGGATAACAATTTCACACAGGA.
```

The SEQ ID NO: 37 primer (AflIII 5'coat), contains the starting sequence of the U1 coat protein and the AflIII recognition site is underlined. In the case of the SEQ ID NO: 38 primer (NcoI/NgoMIV loopout at end), the NcoI and NgoMIV recognition sites are underlined. The SEQ ID NO: 39 oligonucleotide (30B 7792R) anneals just downstream of the PstI site. The resulting product from this polymerase chain reaction (PCR) contained the coat protein that was modified at the C-terminus to provide two cloning sites, NcoI and NgoMIV, and the 3' untranslated region (UTR) of the virus. This 0.8 kb AflIII/PstI fragment was inserted into the 8.4 kb NcoI/PstI fragment of vector pBTI 2150. The resulting plasmid, pLSB2110, allows the insertion of any peptide sequence, possessing both NcoI and NgoMIV overhangs, at the C-terminus of the U1 coat protein.

To generate pLSB1806, overlapping PCR was employed. Two DNA fragments, 0.5 kb and 0.3 kb in size, were amplified using plasmid BSG1057 as a template (Fitzmaurice et al., U.S. Pat. No. 6,656,726 B1). The 0.5 kb fragment was amplified using oligonucleotides Afl-U5-F (CCACATGTATACAATCAACTCTCCGAG; SEQ ID NO: 40) and U5-NN-TPAT-R (CACTGTCCATGGCTGTGGTCC; SEQ ID NO: 41). This resulting fragment contained most of the U5 coat protein (amino acid no. 1-155), however, it lacks the second amino acid residue (proline). The 0.3 kb fragment was amplified using oligonucleotides U5-NN-TPAT (CTTGTCTGGACCACAGCCATGGACAGTGCCGGCACTCCGGCTACTTAG; SEQ ID NO: 42;) and JAL302

(AAACATGATTACGCCMGCTTGCATG; SEQ ID NO: 43). This fragment contains the C-terminal four amino acids of the U5 coat protein as well as the 3' UTR. In addition, it also possesses the two cloning sites, NcoI and NgoMIV, that were placed between amino acid number 155 and 156. Both 0.5 and 0.3 kb fragments were purified to remove all remaining oligonucleotides. These purified DNA fragments were mixed together and amplified by PCR using the two outermost oligonucleotides, AflIII and JAL302. The resultant 0.8 kb AflIII/PstI fragment was subsequently cloned into the 8.4 kb NcoI/PstI fragment from plasmid pBTI 2150. The resulting plasmid pLSB1806 allows the insertion of any peptide sequence, possessing both NcoI and NgoMIV overhangs, at position 155 of the U5 coat protein (before the last four amino acids).

Example 7

Construction of Coat Protein Fusions Displaying the 20 Amino Acid DJ5 Peptide

The initial five DJ5 coat protein fusion constructs are summarized in Table 8. Four of these constructs employed the U1 strain of TMV. The 20 amino acid DJ5 peptide (VHQANPRGSAGPCCTPTKMS; SEQ ID NO: 8) was fused on the surface exposed N and C terminus of the coat protein as well as within the surface exposed "60s" loop between amino acids 64 (Pro) and 67 (Asp), with the concomitant deletion of amino acids 65 (Asp) and 66 (Ser). In the final U1 strain fusion, the epitope was placed internal to the coat protein C-terminal four amino acids (the GPAT position). For the one U5 strain coat protein fusion, the epitope was also placed internal to the C-terminal four amino acids (the TPAT position).

TABLE 8

Coat Protein Fusion Vectors Expressing Recombinant Virions Displaying The 20 Amino Acid DJ5 Peptide In Plants

| Vector Designation | Shorthand descriptor | Coat protein backbone | Epitope insertion location |
|---|---|---|---|
| pLSB-FV1 | DJ5(20)-U1-GPAT | strain U1 | GPAT position |
| pLSB-FV2 | DJ5(20)-U1-C | strain U1 | C-terminus |
| pLSB-FV3 | DJ5(20)-U1-N | strain U1 | N-terminus |
| pLSB-FV4 | DJ5(20)-U1-L | strain U1 | surface exposed "60s" loop |
| pLSB-FV5 | DJ5(20)-U5-TPAT | strain U5 | TPAT position |

To introduce the 20 amino acid DJ5 epitope into these 5 locations, i.e. into the five plasmids described in Example 6, a set of oligonucleotides was designed as illustrated in FIG. 6A. The sequences of the forward and reverse oligonucleotides that were employed in the cloning of 20 amino acid DJ5 peptide coat protein fusions, to yield plasmids pLSB-FV1, pLSB-FV2, pLSB-FV3, pLSB-FV4 and pLSB-FV5, together with associated SEQ ID NO:s, are shown in Table 9, below.

TABLE 9

Forward And Reverse Oligonucleotides

| Forward oligonucleotide | | Reverse oligonucleotide | |
|---|---|---|---|
| Nucleic acid sequence | SEQ ID NO: | Nucleic acid sequence | SEQ ID NO: |
| CATGGTTCATCAAGCTAATCCA GAGGATCTGCTGGACCATGTTG TACTCCAACTAAGATGTCTG | 45 | CCGGCAGACATCTTAGTTGGA GTACAACATGGTCCAGCAGAT CCTCTTGGATTAGCTTGATGA AC | 46 |

The *Nicotiana tabacum* codon usage database is well-known to the art, and as illustrated by FIGS. 8A and 8B, was employed to design the oligonucleotides in Table 9 (SEQ ID NOs 45 and 46). This resulted in codon optimized oligonucleotides for the DJ5(20) peptide. When these oligonucleotides were annealed, they generated a double stranded DNA fragment, with the appropriate 5, and 3, overhangs of "CATG" and "CCGG," respectively (as indicated in Example 6). These fragments were then cloned into the acceptor vectors outlined in Table 7. Insertion of this double stranded DNA fragment resulted in the placement of the DJ5(20) peptide in the various coat protein contexts.

To anneal the forward and the reverse oligonucleotides, 100 pmoles of each oligonucleotide was combined in 10×PCR buffer (Promega) and adjusted to a final volume of 20 µL with water. The oligonucleotide mix was heated to 95° C. for 3 minutes and subsequently cooled gradually to 30° C. at a rate of 0.1° C. per second. The reaction was held at 30° C. and 80 µL of water was added to each tube. For each ligation reaction, 1 µL of the annealed oligonucleotide mix (containing 1 pmole of each oligonucleotide) was employed and combined with 40 ng of the plasmid or vector of interest (cut with the NcoI and NgomIV restriction enzymes (both New England Biolabs)), together with 5 µL of 2× Quick ligation buffer (New England Biolabs) and 0.5 µL of Quick Ligase (New England biolabs). The ligation reaction volume was adjusted to 10 µL and following a 5 minute incubation at room temperature, 2 µL of the reaction was transferred to a 1.5 mL microfuge tube and chilled on ice. To this microfuge tube, 40 µL DH5a competent cells (MAX Efficiency® from Invitrogen Corp., Carlsbad, Calif.) were added and the cell/ligation reaction mixture was incubated on ice for 30 minutes. The cells were then heat shocked at 37° C. for 2 minutes and the microfuge tube immediately returned to the ice. 950 µL of SOC medium (Invitrogen Corp.) was added to the microfuge tube, which was capped and shaken horizontally at 200 rpm and 37° C. for 1 hour. The cells were plated on Luria broth (LB) agar plates (50 or 100 µL per plate), containing 100 mg/L ampicillin, and incubated overnight at 37° C. Single colonies were selected and 2 mL overnight cultures were grown in LB media containing 100 mg/L ampicillin. The plasmid was purified from the DH5a cells and sequenced to confirm the presence of the 20 amino acid DJ5 epitope sequence. The correspondence between the starting vectors and the final vectors containing the 20 amino acid DJ5 epitope at the various insertion sites is summarized in Table 10. Table 11 gives the final amino acid sequences of the translated coat protein fusions displaying the 20 amino acid DJ5 peptide and their associated SEQ ID NOs.

TABLE 10

Correspondence Between The Initial Cloning Vector And The Final Vector Containing The 20 Amino Acid DJ5 Peptide Sequence

| Cloning vector Designation | DJ5 Vector Designation | Shorthand descriptor |
|---|---|---|
| pLSB2109 | pLSB-FV1 | DJ5(20)-U1-GPAT |
| pLSB2110 | pLSB-FV2 | DJ5(20)-U1-C |
| pLSB2268 | pLSB-FV3 | DJ5(20)-U1-N |
| pLSB2269 | pLSB-FV4 | DJ5(20)-U1-L |
| pLSB1806 | pLSB-FV5 | DJ5(20)-U5-TPAT |

Example 8

Construction of Coat Protein Fusions Displaying the 12 Amino Acid N-Terminal Region of the DJ5 Peptide Two additional DJ5-derived coat protein fusion constructs are summarized in Table 12, below, both of which employed the U1 strain of TMV. The fusions displayed the 12 amino acid N-terminal region of the DJ5 peptide (VHQANPRG-SAGP; SEQ ID NO: 44) fused to either the surface exposed N terminus of the coat protein or placed internal to the coat protein C-terminal four amino acids (the GPAT position). Table 12 provides the coat protein fusion vectors used to express recombinant virions displaying the 12 amino acid N-terminal region of the DJ5 peptide in plants.

TABLE 11

Full Amino Acid Sequence Of The 20 Amino Acid DJ5 Peptide Coat Protein Fusion, Together With Their Associated SEQ ID NOs.

| Designation Shorthand descriptor | SEQ ID NOs: | Coat protein amino acid sequence (inserted amino acids are underlined) |
|---|---|---|
| pLSB-FV1 DJ5(20)-U1-GPAT | 47 | MSYSITTPSQFVFLSSAWADPIELINLCTNALGNQFQTQQARTVVQRQFSEVWKPSPQVTVRFPDSDFKVYRYNAVLDPLVTALLGAFDTRNRIIEVENQANPTTAETLDATRRVDDATVAIRSAINNLIVELIRGTGSYNRSSFESSSGLVWTSAMVHQANPRGSAGPCCTPTKMSAGPAT |
| pLSB-FV2 DJ5(20)-U1-C | 48 | MSYSITTPSQFVFLSSAWADPIELINLCTNALGNQFQTQQARTVVQRQFSEVWKPSPQVTVRFPDSDFKVYRYNAVLDPLVTALLGAFDTRNRIIEVENQANPTTAETLDATRRVDDATVAIRSAINNLIVELIRGTGSYNRSSFESSSGLVWTSGPATAMVHQANPRGSAGPCCTPTKMSAG |
| pLSB-FV3 DJ5(20)-U1-N | 49 | MVHQANPRGSAGPCCTPTKMSAGSYSITTPSQFVFLSSAWADPIELINLCTNALGNQFQTQQARTVVQRQFSEVWKPSPQVTVRFPDSDFKVYRYNAVLDPLVTALLGAFDTRNRIIEVENQANPTTAETLDATRRVDDATVAIRSAINNLIVELIRGTGSYNRSSFESSSGLVWTSGPAT |
| pLSB-FV4 DJ5(20)-U1-L | 50 | MSYSITTPSQFVFLSSAWADPIELINLCTNALGNQFQTQQARTVVQRQFSEVWKPSPQVTVRFPGSPMVHQANPRGSAGPCCTPTKMSAGPSGDFKVYRYNAVLDPLVTALLGAFDTRNRIIEVENQANPTTAETLDATRRVDDATVAIRSAINNLIVELIRGTGSYNRSSFESSSGLVWTSGPAT |
| pLSB-FV5 DJ5(20)-U5-TPAT | 51 | MYTINSPSQFVYLSSAYADPVQLINLCTNALGNQFQTQQARTTVQQQFADAWKPVPSMTVRFPASDFYVVYRYNSTLDPLITALLNSFDTRNRIIEVDNQPAPNTTEIVNATQRVDDATVAIRASINNLANELVRGTGMFNQASFETASGLVWTTAMVHQANPRGSAGPCCTPTKMSAGTPAT |

TABLE 12

| Coat Protein Fusion Vectors | | | |
|---|---|---|---|
| Designation | Shorthand descriptor | Coat protein backbone | Epitope insertion location |
| pLSB-FV6 | DJ5(12)-U1-N | strain U1 | N-terminus |
| pLSB-FV7 | DJ5(12)-U1-GPAT | strain U1 | GPAT position |

To introduce the 12 amino acid epitope (12 mer) into these 2 locations, a set of two oligonucleotides was designed, the sequences shown in Table 13, below, together with their associated SEQ ID NOs. To anneal the forward and the reverse oligonucleotides, the procedure outlined in Example 7 was followed. For each ligation reaction 1 μL of the annealed oligonucleotide mix, containing 1 pmole of each oligonucleotide, was employed. This was combined with the plasmid of interest (cut with the NcoI and NgomIV restriction enzymes) and the ligation reaction protocol together with its transformation into chemically competent DH5a cells was as detailed in Example 7, supra. Table 13, below, provides the forward and reverse primers employed in the cloning of the coat protein fusions consisting of the 12 amino acid N-terminal region of the DJ5 peptide, to yield plasmids pLSB-FV6 and pLSB-FV7.

TABLE 13

| Forward And Reverse Primers | | | |
|---|---|---|---|
| Forward primer | | Reverse primer | |
| Nucleic acid sequence | SEQ ID NOs | Nucleic acid sequence | SEQ ID |
| CATGGTTCATCAAGCTAATCCAAGAGGATCTGCTGGACCA G | 52 | CCGGCTGGTCCAGCAGATCCTCTTGGATTAGCTTGATGAAC | 53 |

The cells were plated on LB agar plates (50 or 100 μL per plate), containing 100 mg/L ampicillin, and incubated overnight at 37° C. Single colonies were selected and 2 mL overnight cultures were grown in LB media containing 100 mg/L ampicillin. The plasmid was purified from the DH5a cells and sequenced to confirm the presence of the 12 amino acid DJ5-derived epitope sequence. The correspondence between the starting vectors and the final vectors containing the 12 amino acid DJ5-derived epitope at the two chosen insertion sites is summarized in Table 14, below. Table 15, below, provides the final amino acid sequences of the translated coat protein fusions displaying the 12 amino acid N-terminal region of the DJ5 peptide and their associated SEQ ID NOs.

TABLE 14

Correspondence Between The Initial Cloning Vector And The Final Vector Containing The 12 Amino Acid DJ5-Derived Peptide Sequence

| Cloning vector Designation | DJ5 Vector Designation | Shorthand descriptor |
|---|---|---|
| pLSB2268 | pLSB-FV6 | DJ5(12)-U1-GPAT |
| pLSB2109 | pLSB-FV7 | DJ5(12)-U1-C |

TABLE 15

Full Amino Acid Sequence Of The Coat Protein Fusions Displaying The 12 Amino Acid N-Terminal Region Of The DJ5 Peptide, Together With Their Associated SEQ ID NOs

| Designation Shorthand descriptor | SEQ ID NOs | Amino acid sequence (inserted amino acids are underlined) |
|---|---|---|
| pLSB-FV6 DJ5(12)-U1-N | 54 | MVHQANPRGSAGPAGSYSITTPSQFVFLSSAWAD PIELINLCTNALGNQFQTQQARTVVQRQFSEVWK PSPQVTVRFPDSDFKVYRYNAVLDPLVTALLGAF DTRNRIIEVENQANPTTAETLDATRRVDDATVAI RSAINNLIVELIRGTGSYNRSSFESSSGLVWTSG PAT |
| pLSB-FV7 DJ5(12)-U1-GPAT | 55 | MSYSITTPSQFVFLSSAWADPIELINLCTNALGN QFQTQQARTVVQRQFSEVWKPSPQVTVRFPDSDF KVYRYNAVLDPLVTALLGAFDTRNRIIEVENQAN PTTAETLDATRRVDDATVAIRSAINNLIVELIRG TGSYNRSSFESSSGLVWTSAMVHQANPRGSAGPA GPAT |

Example 9

Production of TMV-FV1, TMV-FV2, TMV-FV3, TMV-FV4 and TMV-FV5

The virus TMV-FV1 was produced by transcription of plasmid pLSB-FV1. Infectious transcripts were synthesized from transcription reactions with T7 RNA polymerase (Ambion) according to the manufacturers instructions. Following the verification of transcript integrity by agarose gel electrophoresis, the RNA transcript was combined with an abrasive solution (a bentonite/celite mixture suspended in a glycine/phosphate buffer containing sodium pyrophosphate) and used to inoculate Nicotiana benthamiana leaves of 23 to 28 day old plants. Approximately 5 to 13 days post-inoculation, depending on the severity of the infection, systemic movement of the recombinant virus was visible in the plant tissue, by virtue of a mosaic phenotype on the virus-containing leaves. Systemically infected tissue was harvested for virus extraction and purification. It should be noted that alternative host plants, other than Nicotiana benthamiana can be employed in the production of TMV-FV1. For example, Nicotiana excelsiana or Nicotiana tabacum represent two possible alternative plant hosts. For the latter two hosts, tissue is harvested 2.5-5 weeks post inoculation, after systemic spread of the virus.

To produce TMV-FV2 virus, transcript was generated from plasmid pLSB-FV2, inoculated onto plants and systemically infected tissue harvested in a manner similar to that described for the production of virus TMV-FV1.

To produce TMV-FV3 virus, transcript was generated from plasmid pLSB-FV3, inoculated onto plants and systemically infected tissue harvested in a manner similar to that described for the production of virus TMV-FV1.

To produce TMV-FV4 virus, transcript was generated from plasmid pLSB-FV4, inoculated onto plants and systemically infected tissue harvested in a manner similar to that described for the production of virus TMV-FV1.

To produce TMV-FV5 virus, transcript was generated from plasmid pLSB-FV5, inoculated onto plants and systemically infected tissue harvested in a manner similar to that described for the production of virus TMV-FV1.

Example 10

Extraction and Purification of TMV-FV1, TMV-FV2. TMV-FV3. TMV-FV4 and TMV-FV5

The recombinant virus TMV can be extracted from the infected plant tissue immediately following harvesting. Alternatively, the tissue can be can be stored for 2 hours to 14 days at 4° C., or at −20° C. to −80° C. (for days to months) prior to performing the extraction. The tissue can also be flash frozen prior to extraction, to aid in tissue disintegration.

Several procedures have been documented for the purification of recombinant TMV virus from infected plant tissue. For examples Garger et al. (U.S. Pat. Nos. 6,033,895, 6,037, 456 and 6,303,779) and Pogue et al., (U.S. Pat. Nos. 6,740, 740 and 6,730,306, incorporated by reference herein) disclose methods based on the pH adjustment and heat treatment of the homogenate "green juice" obtained following extraction of the infected tissue. Pogue et al., also disclose a procedure based on the use of polyethyleneimine ("PEI") to aid in the separation of the plant host proteins and the recombinant TMV. These procedures and modifications thereof, designed to improve epitope stability (i.e. minimize degradation by proteolysis) during extraction and processing, and recombinant virion solubility, were used in the purification of virus TMV-FV1, the purification of TMV-FV2, the purification of TMV-FV3, the purification of TMV-FV4 and the purification of TMV-FV5.

A. Purification of TMV-FV1 Fusion VCP from Plant Tissue

TMV-FV1 was purified from plant tissue as follows. Systemically infected plant tissue (leaf and stalks) was harvested and combined with chilled extraction buffer EB (100 mM Tris, pH 8, 0.86 M sodium chloride, 0.2% v/v Triton® X-100), to which 0.04% w/v sodium metabisulfite had been added, at a buffer volume (mL) to tissue mass (g) ratio of 2:1. The plant tissue and extraction buffer were homogenized for 1 minute in a 1 L Waring® blender, transferred to an Erlenmeyer flask and further homogenized for 1 minute using a Polytron® (Brinkmann Instruments).

This homogenate was passed through four layers of cheesecloth, to remove the fiber, to yield a plant extract, which will hereafter be referred to as "green juice." The green juice was transferred to a centrifuge bottle, centrifuged at 10,000×G for 10 minutes and the supernatant discarded. The majority of TMV-FV1 fusion VCP, which was insoluble, was present in the pellet. The pellet was resuspended to the original green juice volume in the extraction buffer EB, with the aid of the Polytron® (1 minute of homogenization). Following the Polytron® treatment, the resuspended pellet was transferred to a centrifuge bottle, centrifuged at 10,000×G for 10 minutes and the supernatant discarded. This step: pellet resuspension in extraction buffer EB, Polytron® homogenization and centrifugation at 10,000×G for 10 minutes, was repeated two additional times. The purpose of these repeated steps was to effect the separation of the plant-derived proteins and pigments from the insoluble TMV DJ5 coat protein fusion, which was facilitated by the presence of a relatively high sodium chloride concentration and detergent in the buffer EB.

The number of repetitions required to remove all the plant-derived pigments, to yield a white to light tan pellet, may be dependent on the age of the harvested tissue and the TMV coat protein fusion being expressed.

If green host-derived pigment remains associated with the pellet, additional washes to the TMV coat protein fusion-containing pellet can be performed employing a high pH buffer, for example, 50 mM triethylamine containing 0.2% v/v Triton® X-100 and 0.04% w/v sodium metabisulfite (buffer B1). For TMV-FV1, these additional pellet washes were performed. Specifically the pellet obtained following the three buffer EB washes was resuspended to the original green juice volume in buffer B1 with the aid of the Polytron® (1 minute of homogenization) and then transferred to a centrifuge bottle, centrifuged at 10,000×G for 10 minutes and the supernatant discarded. This pellet was subjected to an additional buffer B1 wash, and the resulting pellet was then resuspended, with the aid of the Polytron®, in approximately the original green juice volume of 1× phosphate buffered saline ("PBS"), pH 7.4, centrifuged at 10,000×G for 10 minutes, and the supernatant discarded. The PBS wash of the pellet was repeated and the final pellet was resuspended in approximately one tenth of the original green juice volume of 1×PBS. The purpose of the two PBS washes was to remove residual detergent from the TMV DJ5 coat protein fusion-containing pellet and ensure that the final TMV coat protein fusion preparation was close to neutral pH.

Aliquots of the green juice, the discarded supernatants and the final pellet preparation, resuspended in 1×PBS, were subjected to PAGE analysis. The PAGE analysis showed that the supernatants contained minimal amounts of the TMV-FV1 DJ5 coat protein fusion, whereas this was the principal protein species present in the final pellet preparation. Conversely the majority of the plant-derived host proteins were present in the discarded supernatants, and minimal host protein was detected in the final pellet. The same procedure was employed in the purification of TMV-FV2, the purification of TMV-FV4 and the purification of TMV-FV5, with similar results.

B. Purification of TMV-FV3 Fusion VCP from Plant Tissue

TMV-FV3 was purified from plant tissue as follows. Systemically infected leaf and stalk tissue was macerated in a Waring® blender for 1 minute at the high setting with chilled buffer EB1 (0.86 M sodium chloride, containing 0.04% w/v sodium metabisulfite) at a buffer (mL) to tissue (g) ratio of 2:1. The macerated material was strained through four layers of cheesecloth to remove fibrous material. The resultant green juice was adjusted to a pH of 5.0 with phosphoric acid. The pH adjusted green juice was heated to 47° C. and held at this temperature for 5 minutes and then cooled to 15° C. The heat-treated green juice was centrifuged at 6,000×G for 3 minutes resulting in two fractions, supernatant S1 and pellet P1. The pellet P1 fraction was resuspended in distilled water using a volume of water equivalent to 1/2 of the initial green juice volume. The resuspended pellet P1 was adjusted to a pH of 7.5 with sodium hydroxide and centrifuged at 6,000×G for 3 minutes resulting in two fractions, supernatant S2 and pellet P2. Virus was precipitated from both supernatant fractions S1 and S2 by the addition of 4% w/v polyethylene glycol (PEG) 6,000 and 4% w/v sodium chloride. After incubation at 4° C. (1 hour), precipitated virus was recovered by centrifugation at 10,000×G for 10 minutes. The virus pellet was resuspended in 1×PBS, pH 7.4 and clarified by centrifugation at 10,000×G for 3 minutes to yield a final clarified TMV-FV3 preparation.

Aliquots of the green juice, the supernatants S1 and S2 and the final virus preparation pre and post the clarification spin were subjected to PAGE analysis. The PAGE analysis showed the majority of the principal coat protein band present in the green juice partitioned into the supernatant S1 with low levels present in the supernatant S2. With PEG precipitation of the supernatant S1 and the supernatant S2 and the final clarification spins, virus was further purified from the plant host proteins to yield two substantially pure TMV-FV3 virus preparations. The majority of the TMV-FV3 virus recovered was present in the pellet obtained following the supernatant S1 PEG precipitation. A minor portion of the TMV-FV3 virus was removed by the final clarification spin, together with residual plant host proteins.

C. Purification of TMV-FV1, TMV-FV2, TMV-FV4 and TMV-FV5 Fusion VCP from Plant Tissue The procedure outlined for TMV-FV3, supra, was applied to the other DJ5 epitope TMV coat protein fusions, namely TMV-FV1, TMV-FV2, TMV-FV4 and TMV-FV5. For TMV-FV1, TMB-FV2 and TMV-FV4, PAGE analysis indicated that the coat protein band was present in the initial green juice, however the band was absent from both the supernatant S1 and the supernatant S2 and no TMV coat protein fusion was recovered by the procedure outlined for TMV-FV3. Further analysis showed that TMV-FV1, TMV-FV2 and TMV-FV4 were insoluble and present in the pellet P2, together with plant pigments and proteins.

In order to purify the insoluble TMV-FV1, TMV-FV2 and TMV-FV4 fusion proteins from the plant-derived proteins and pigments, the procedure outlined above for TMV-FV1 was employed. In the case of TMV-FV5, the procedure outlined for TMV-FV3 was initially unsuccessful. When extractions of freshly harvested infected tissue were performed, employing a Waring® blender for homogenization, minimal full length TMV-FV5 was recovered, due to degradation that occurred during processing. By modifying the procedure, and starting with frozen tissue that was processed with a mortar and pestle, followed by Polytron® homogenization, approximately 30-40% of full-length TMV-FV5 was present in the supernatant S1. This was further concentrated by PEG precipitation, and 15-17% of this TMV-FV5 remained soluble following the final clarification spin, with the remainder present in the clarification pellet. Both the clarification pellet and the clarified virus preparation contained significant quantities of plant host proteins, resulting in a final product with low purity.

These results suggested that the starting tissue state (fresh vs. frozen) and/or the tissue disintegration step(s) employed played a role in epitope stability.

D. Optimizing Purification of TMV-FV5 Fusion VCP from Plant Tissue

Since TMV-FV5 exhibited partial solubility with the purification methods of Part C, supra, further optimization was performed on the TMV-FV3 procedure, to determine if recovery and purity of the final TMV-FV5 virus preparation could be improved.

Frozen, systemically infected leaf and stalk tissue was combined with 2 volumes of buffer EB1 and macerated with a pestle and mortar, followed by further homogenization using a Polytron®. This extract was strained through four layers of cheesecloth and the resultant green juice was adjusted to a pH of 5.0 with phosphoric acid. The pH adjusted green juice was centrifuged at 6,000×G for 3 minutes resulting in two fractions, supernatant S1 and pellet P1, the latter of which was not processed further. The supernatant S1 was adjusted to pH 6 by the addition of sodium hydroxide and contacted with 5% w/v activated carbon powder (e.g. Nuchar grade SA-20 or Norit grade KB-FF) for 1 hour at 4° C. The activated carbon containing supernatant S1 was then adjusted to pH 8 with sodium hydroxide and centrifuged at 3000×G for 15 minutes to remove the activated carbon. The supernatant from this was taken forward and the TMV-FV5 precipitated by the addition of 4% w/v polyethylene glycol (PEG) 6,000 and 4% w/v sodium chloride. After incubation at 4° C. (1 hour), precipitated virus was recovered by centrifugation at 10,000×G for 10 minutes. The virus pellet was resuspended in 1×PBS, pH 7.4 and no clarification spin was performed.

Aliquots of the green juice, the supernatant S1 at the various stages of processing, the resuspended pellet P1 and the final TMV-FV5 preparation were subjected to PAGE analysis. As noted previously, approximately 40% of the green juice coat protein was present in the supernatant S1 together with substantial levels of plant host proteins, while visually the majority of the green pigment partitioned into the pellet P1. Following the activated carbon treatment at pH 6 there was a substantial reduction in the host protein level in the supernatant with recovery of 70-80% of the TMV-FV5. With pH 8 adjustment and centrifugation to remove the activated carbon the TMV-FV5 losses were minimal. PEG precipitation, as described above, from the pH 8 supernatant was performed to further concentrate the TMV-FV5, resulting in a final virus preparation with satisfactory purity and a notable improvement over the virus obtained from the same procedure where no activated carbon or pH steps were employed.

Polyacrylamide gel electrophoresis (PAGE) analysis, and Western blot analysis (Table 16) were performed on the purified recombinant viruses to assess purity and epitope immunoreactivity. For the Western blot analysis a goat antibody raised against the pro-form of GDF8 was employed. This polyclonal antibody, denoted Goat #661, was determined to be neutralizing in an in vitro GDF8 neutralization assay. Western blots were also performed with a rabbit antibody raised against wild-type TMV, denoted PVAS 135D (obtained from the ATCC collection). Table 16, below, summarizes the solubility, purity, polyacrylamide gel electrophoresis (PAGE) profile and reactivity, of the 20 amino acid DJ5 peptide coat protein fusions, with the GDF8 neutralizing Goat #661 antibody, and with the anti-TMV antibody (PVAS-135D), by Western blotting.

TABLE 16

Physical Properties Of The 20
Amino Acid DJ5 Peptide Coat Protein Fusions

| Designation | | | | Western blot detection | |
|---|---|---|---|---|---|
| Shorthand descriptor | Solubility | Purity | PAGE profile | Anti-GDF8 | Anti-TMV |
| TMV-FV1 DJ5(20)-U1-GPAT | Insoluble | >90% | Oligomeric ladder (7 to 9 bands) | Yes (5 to 6 bands) | Yes (5 to 6 bands) |
| TMV-FV2 DJ5(20)-U1-C | Insoluble | >90% | Oligomeric ladder (5 to 6 bands) | Yes (5 to 6 bands) | Yes (5 to 6 bands) |

TABLE 16-continued

Physical Properties Of The 20
Amino Acid DJ5 Peptide Coat Protein Fusions

| Designation | | | | Western blot detection | |
|---|---|---|---|---|---|
| Shorthand descriptor | Solubility | Purity | PAGE profile | Anti-GDF8 | Anti-TMV |
| TMV-FV3 DJ5(20)-U1-N | Soluble | >90% | Single band | No | Yes |
| TMV-FV4 DJ5(20)-U1-L | Insoluble | >90% | Oligomeric ladder (5 to 6 bands) | Yes (5 to 6 bands) | Yes (5 to 6 bands) |
| TMV-FV5 DJ5(20)-U5-TPAT | Partially soluble | >90% | Oligomeric ladder (5 to 6 bands) | Yes (5 to 6 bands) | Yes (5 to 6 bands) |

All the recombinant TMV fusions listed in Table 16 were successfully purified to greater than 90% purity. In the case of TMV-FV1, TMV-FV2 and TMV-FV4, the purified TMV was insoluble. When analyzed by PAGE, a characteristic laddering pattern was observed for the three U1 strain fusions. On 10-20% Tris-glycine gels, the lowest (monomer) band migrated at approximately 22 kDa, as expected for the 20 amino acid DJ5 peptide coat protein fusion. The protein band above this monomer migrated at 45 kDa and the protein band above this at 65-70 kDa. By Western blot the majority of these bands were detected by the Goat #661 antibody as well as the anti-TMV PVAS-135D antibody (very high molecular weight bands, >200 kDa, were not always detected due to poor transfer from the gel to the membrane). Together with the observed molecular weights, these results indicate that the additional bands represent dimers, timers and higher multimers of the 20 amino acid DJ5 peptide coat protein fusion. When the PAGE analysis of TMV-FV1, TMV-FV2 and TMV-FV4 was performed in the absence of reducing agent, the proportion of monomer decreased, with an observable increase in the proportion of higher order oligomers. This suggests that disufilde bridging between the 20 amino acid DJ5 peptide coat protein fusions was occurring. The 20 amino acid DJ5 peptide contains two cysteine residues, which are likely involved in the formation of the observed higher order oligomers. For TMV-FV5, the final virus preparation was partially soluble and exhibited the same reducing agent-dependent oligomeric banding pattern as TMV-FV1, TMV-FV2 and TMV-FV4 by both PAGE and Western blot analysis. The slightly improved solubility of TMV U5 may be due to the use of the strain U5 coat protein in place of the strain U1 coat protein. The only soluble TMV fusion from the series listed in Table 15 was TMV-FV3, where the 20 amino acid DJ5 peptide was displayed as an N-terminal fusion to the strain U1 coat protein. For TMV-FV3, the coat protein migrated with a mass of approximately 18 kDa on the PAGE gel, similar to the wild-type U1 coat protein. This suggested truncation of the epitope. No oligomeric ladder was observed and by Western blot the TMV fusion was detected by the anti-TMV PVAS 135D antibody but not by the GDF8 neutralizing Goat #661 antibody. This lack of reactivity with the Goat #661 antibody supports truncation of some or all of the 20 amino acid DJ5 peptide fusion in the case of TMV-FV3.

Example 11

Characterization of TMV-FV1, TMV-FV2, TMV-FV3. TMV-FV4 and TMV-FV5 by MALDI

In addition to PAGE and Western blot analysis, the virus preparations were characterized using Matrix Assisted Laser Desorption Ionization—Time of Flight (MALDI-TOF) (Table 17). PEG precipitated, resuspended virus preparations were diluted in a sinapinic acid (Aldrich, Milwaukee, Wis.) solution, with the dilution in the range of 1:1 to 1:20 depending in the virus concentration, to obtain a final concentration of 1 to 1.5 mg/mL. The sinapinic acid was prepared at a concentration of 10 mg/mL in 0.1% aqueous triflouroacetic acid/acetonitrile (70/30 by volume). The sinapinic acid treated sample (1.0 µl) was applied to a stainless steel MALDI plate surface and allowed to air dry at room temperature. MALDI-TOF mass spectra were obtained with a PerSeptive Biosystems DE-PRO (Houston, Tex.) operated in the linear mode. A pulsed laser operating at 337 nm was used in the delayed extraction mode for ionization. An acceleration voltage of 25 kV with a 90% grid voltage and a 0.1% guide wire voltage was used. Approximately 100 scans were acquired and averaged over the mass range 2,000-156,000 Da with a low mass gate of 2,000. Ion source and mirror pressures were approximately $1.2 \times 10^{-7}$ and $1.6 \times 10^{-7}$ Torr, respectively. All spectra were mass calibrated with a two-point fit using horse apomyoglobin (16,952 Da) and insulin (5734 Da) as standards. Table 17, below, provides a summary of the expected and observed molecular weights, by MALDI, for the 20 amino acid DJ5 peptide fusions.

TABLE 17

Expected And Observed Molecular Weights
20 Amino Acid DJ5 Peptide Fusions, By MALDI

| Designation | MALDI analysis | | |
|---|---|---|---|
| Shorthand descriptor | Expected MW | Observed MW | Match |
| TMV-FV1 DJ5(20)-U1-GPAT | 19,833 Da (-Met/Acetyl) | 19,829 Da | Yes |
| TMV-FV2 DJ5(20)-U1-C | 19,890 Da (-Met/Acetyl) | 19,890 Da | Yes |
| TMV-FV3 DJ5(20)-U1-N | 19,685 (-Met/Acetyl) | 17,745 Da | No |
| TMV-FV4 DJ5(20)-U1-L | 20,100 Da (-Met/Acetyl) | 20,097 Da | Yes |
| TMV-FV5 DJ5(20)-U5-TPAT | 19,878 Da (-Met/Acetyl) | 19,876 Da | Yes |

For TMV-FV1, TMV-FV2, TMV-FV4 and TMV-FV5 the observed molecular weights matched the expected molecular weights, for the case where the coat protein fusion's N-terminal Met residue was removed and the adjacent amino acid acetylated. The presence of the intact 20 amino acid DJ5 epitope on TMV-FV1, TMV-FV2, TMV-FV4 and TMV-FV5, together with the positive anti-GDF8 Western blot reported in Table 16, confirmed that all four of these TMV fusions were potential vaccine candidates. For the N-terminal fusion, TMV-FV3, a mass of 17,745 Da was obtained, representing multiple truncation possibilities. By performing liquid chromatography on a tryptic digest of TMV-FV3 and analyzing the resolved peptide fragments by tandem mass spectrometry it was determined that the C-terminus of TMV-FV3 was intact and that the DJ5 epitope was cleaved, to leave only the final C-terminal serine, which was acetylated. Since this fusion failed to retain the 20 amino acid DJ5 epitope and was not detected in Western blots by the anti-GDF8 Goat #661 antibody, it was not pursued further as a vaccine candidate. The confirmation by mass spectrometry that TMV-FV3 lacked the DJ5 epitope and its migration as a single band by PAGE analysis (Table 16), indicates that amino acid residues within the DJ5 epitope were responsible for the cross-linking and higher order oligomer formation. As indicated above, the two cysteines within the DJ5 epitope were considered the most likely amino acids to be involved in this cross-linking.

Example 12

Extraction and Purification of TMV-FV6 and TMV-FV7

Of the five 20 amino acid DJ5 peptide fusions purified (see Example 10), and characterized by mass spectrometry (Example 11), four were identified as potential vaccine candidates, namely TMV-FV1, TMV-FV2, TMV-FV4 and TMV-FV5. These four TMV fusions, however, were insoluble. Since the TMV fusion insolubility was correlated with the presence of the 20 amino acid DJ5 peptide, which resulted in coat protein cross-linking, it was hypothesized that the oligomer formation was related to the TMV fusion insolubility. Furthermore, the two cysteines present in the DJ5 peptide appeared responsible for this cross-linking, and so two new constructs were proposed in which these two residues were eliminated. The two new constructs, pLSB-FV6 and pLSB-FV7, were designed to display the N-terminal 12 amino acids of the DJ5 peptide, as N-terminal and GPAT fusions respectively, to the U1 coat protein.

The same points raised in Example 10, regarding tissue harvesting and storage prior to the extraction also apply to TMV-FV6 and TMV-FV7. As noted in Example 10, supra, several procedures have been documented for the purification of recombinant TMV virus from infected plant tissue. These procedures and modifications thereof, designed to improve epitope stability (i.e. minimize degradation by proteolysis) during extraction and processing, and improve virion solubility, were used in the purification of virus TMV-FV6 and the purification of TMV-FV7.

For TMV-FV7, the procedure outlined for TMV-FV3 in Example 10 was employed starting from freshly harvested, systemically infected plant tissue. PAGE analysis of the in process samples and the final clarified virus preparation showed that approximately 80% of the TMV-FV7 present in the green juice partitioned into the supernatant S1, with the remainder present in the supernatant S2. Only the supernatant S1 was carried forward for PEG precipitation and following the final clarification spin, which precipitated some residual host proteins, the majority of the purified TMV-FV7 remained soluble.

When the procedure outlined for TMV-FV3 in Example 10 was employed for the purification of TMV-FV6, starting from freshly harvested tissue, only low levels of the product was present in the supernatant S1, with the majority of the TMV-FV6 associated with the pellet P2. The protocol was then modified such that the systemically infected tissue was frozen prior to extraction and tissue maceration was performed with the aid of a mortar and pestle. With these alterations PAGE analysis indicated that approximately 30% of the TMV-FV6 partitioned into the supernatant S1, with the remainder detected in the supernatant S2 and pellet P2. The supernatant S1 was PEG precipitated as described in Example 10, supra, and the concentrated virus subjected to a clarifying spin. The TMV-FV6 partitioned into the clarification spin pellet, and PAGE analysis showed minimal contamination by plant host proteins Polyacrylamide gel electrophoresis (PAGE) analysis, and Western blot analysis (Table 18) was performed on the purified recombinant viruses to assess purity. For the Western blot analysis a goat antibody raised against the pro-form of GDF8 was employed. This antibody, denoted Goat #661, was determined to be neutralizing in an in vitro GDF8 neutralization assay. Western blots were also performed with a rabbit antibody raised against wild-type TMV, denoted PVAS 135D [obtained from the ATCC collection (ATCC No. PVAS 135D]. Table 18, below, provides data for the solubility, purity, polyacrylamide gel electrophoresis (PAGE) profile and reactivity with the GDF8 neutralizing Goat #661 antibody and the anti-TMV antibody (PVAS-135D) by Western blot, for the shortened 12 amino acid DJ5 peptide coat protein fusions.

TABLE 18

Physical Properties Of The 12 Amino Acid DJ5 Peptide Coat Protein Fusions

| Designation Shorthand descriptor | Solubility | Purity | PAGE profile | Western blot detection | |
|---|---|---|---|---|---|
| | | | | Anti-GDF8 | Anti-TMV |
| TMV-FV6 DJ5(12)-U1-N | Partially soluble | >90% | Single band | Yes | Yes |
| TMV-FV7 DJ5(12)-U1-N | Soluble | >90% | Single band | Yes | Yes |

Both recombinant TMV fusions listed in Table 18 were successfully purified to greater than 90% purity. In the case of TMV-FV6, the final purified virus was partially soluble, while TMV-FV7 was completely soluble. When analyzed by PAGE, both TMV fusions migrated as a single band and these coat protein fusions were detected by both the anti-TMV PVAS-135 and the anti-GDF8 Goat #661 antibodies. Minimal or no higher molecular weight species were detected by PAGE or Western blot, supporting the hypothesized role played by the two DJ5 epitope cysteines in coat protein cross-linking. The improved solubility observed also indicates that the oligomerization was responsible for the macromoleular association of the recombinant TMV virions.

Example 13

Characterization of TMV-FV6 and TMV-FV7 by MALDI

In addition to PAGE and Western blot analysis, the TMV-FV6 and TMV-FV7 virus preparations were characterized using Matrix Assisted Laser Desorption Ionization—Time of Flight (MALDI-TOF) (Table 19). The preparation and spotting of the PEG precipitated and resuspended virus in sinapinic acid was as outlined in Example 11. MALDI-TOF spectra acquisition on a PerSeptive Biosystems DE-PRO (Houston, Tex.) was also performed as described in Example 11, using horse apomyoglobin and insulin as mass standards. Table 19, below. provides a summary of the expected and observed molecular weights, by MALDI, for the shortened 12 amino acid DJ5 peptide fusions.

TABLE 19

Expected And Observed Molecular Weights 12 Amino Acid DJ5 Peptide Fusions, By MALDI

| Designation Shorthand descriptor | MALDI analysis | | |
|---|---|---|---|
| | Expected MW | Observed MW | Match |
| TMV-FV6 DJ5(12)-U1-N | 18,794 Da (-Met/Acetyl) | 18,792 Da | Yes |
| TMV-FV7 DJ5(12)-U1-GPAT | 18,981 Da (-Met/Acetyl) | 18,977 Da | Yes |

For both TMV-FV6 and TMV-FV7, the observed molecular weights matched the expected molecular weights, for the case where the coat protein fusion's N-terminal Met residue was removed and the adjacent amino acid acetylated. The presence of the intact 12 amino acid DJ5 epitope on TMV-FV6 and TMV-FV7, together with the positive anti-GDF8 Western blot data reported in Table 18, confirmed that both of these TMV fusions were potential vaccine candidates.

Example 14

Characterization of TMV-FV5. TMV-FV6 and TMV-FV7 by ELISA

In addition to immunoanalysis by Western blot, enzyme linked immunosorbant assays (ELISAs) were also performed with the soluble and partially soluble DJ5 peptide fusions, namely TMV-FV5, TMV-FV6 and TMV-FV7. Since the TMV fusions are not denatured prior to contact with antibody, the ELISAs permit evaluation of epitope recognition and accessibility in the context of the assembled recombinant virion. The ELISAs were performed in two formats; by coating the TMV fusion onto the ELISA plate and by displaying the recombinant TMV fusion in a sandwich format using the anti-TMV PVAS-135D antibody. For detection of the recombinant TMV fusion three antibodies were employed:

Goat #661. This goat polyclonal antibody was raised against purified recombinant GDF8 prohormone (see Example 2)GDF8 and was determined to be neutralizing in an in vitro GDF8 neutralization assay (see Example 3).

Rabbit #1286. This rabbit polyclonal antibody was raised against a Keyhole limpet hemocyanin (KLH) conjugate of the 20 amino acid DJ5 peptide (SEQ ID NO: 8) and though capable of recognizing this peptide in ELISA format, it was not capable of in vitro GDF8 neutralization.

Rat MAB788 (R&D Systems, Inc.; Minneapolis, Minn.). This monoclonal anti-mouse GDF8 antibody was purified from a hybridoma resulting from the fusion of a mouse myeloma with B cells obtained from a rat immunized with purified, NSO-derived recombinant mouse GDF8. The monoclonal antibody was capable of neutralization of mouse GDF8 bioactivity.

For the indirect ELISA, the recombinant TMV fusion TMV-FV5, TMV-FV6 or TMV-FV7, was diluted in carbonate/bicarbonate buffer (pH 9.6) and was used to coat a 96-well microtiter plate (MaxSorb, Nunc) overnight at 4° C. (50 µL per well). A maximum of 200 ng target antigen was coated with a 2-fold serial dilution performed. As a control GDF8 prohormone (see Example 1) was employed, with a maximum of 100 ng per well. A 2-fold serial dilution was also performed with GDF8 prohormone. The coating solution was removed and the plates blocked with 5% w/v dry skim milk in 1×TBST buffer (Tris-buffered saline with TWEEN™ 20) for 1 to 2 hours at room temperature (200 μL blocking solution per well). The wells were washed twice with 1×TBST and 50 μL of the antibody (Goat #661, Rat MAB788 or Rabbit #1286), diluted in 1×TBST with 0.5% w/v dry skim milk, was added per well. All antibodies were employed at a dilution of 1:1000, with the exception of Rabbit #1286, which was employed at 1:100. Following a 1 hour incubation at room temperature with the primary antibody, the plate was washed 5 times with 1×TBST and 50 μL of the appropriate horseradish peroxidase (HRP) conjugated secondary antibody was added at a dilution of 1:10,000 in 1×TBST containing 0.5% w/v dry skim milk. The plate was incubated with the secondary antibody for 1 hour at room temperature, washed five times with 1×TBST and 50 μL of 3,3',5,5'-tetramethyl bezidine substrate solution was added per well. The HRP catalyzed reaction was permitted to proceed for 5 to 20 minutes and stopped by the addition of 50 μL of 1 N sulfuric acid. The plate absorbance (OD) was read at 450 nm in a 96-well plate spectrophotometer (Molecular Devices).

For the double antibody sandwich (DAS) ELISA, 50 μL of anti-TMV polyclonal antibody PVAS-135D, diluted at 1:500 in carbonate/bicarbonate buffer (pH 9.6) was used to coat 96-well microtiter plates (MaxSorb, Nunc) overnight at 4° C. The coating solution was removed and the wells were blocked with 200 μL of 1×TBST buffer containing 5% w/v dry skim milk for 1 to 2 hours at room temperature. Following the blocking step, the wells were washed 5 times and 50 μL of a recombinant TMV virion solution, containing TMV-FV5, TMV-FV6 or TMV-FV7, was added per well (1×TBST with 0.2% w/v dry skim milk employed as a buffer). A maximum of 11 pmoles of coat protein was employed per well, with a two-fold serial dilution of the recombinant virion present on each plate. To permit capture of the TMV virion by the coated PVAS-135D antibody, the plate was incubated for 1 hour at room temperature. Excess TMV virion was removed by washing the plate 5 times with 1×TBST and the primary antibody (either Goat #661 or Rat MAS788, diluted at 1:1000 in 1×TBST with 0.5% w/v dry skim milk) was added for a 1 hour incubation at room temperature. The plate was then washed 5 times with 1×TBST and 50 μL of the appropriate horse-radish peroxidase (HRP) conjugated secondary antibody was added at a dilution of 1:10,000 in 1×TBST containing 0.5% w/v skim milk. The plate was incubated with the secondary antibody for 1 hour at room temperature, washed five times with 1×TBST and 50 μL of 3,3',5,5'-tetramethyl bezidine substrate solution was added per well. The HRP catalyzed reaction was permitted to proceed for 5 to 20 minutes and stopped by the addition of 50 μL of 1 N sulfuric acid. The plate absorbance was read at 450 nm in a 96-well plate Spectrophotometer (Molecular Devices). Sandwich ELISAs were also performed where the Rat MAB788 antibody (diluted at 1:1000) was employed as the capture antibody. For these ELISAs the primary antibody employed was the Goat #661 antibody. These sandwich ELISAs also included a GDF8 prohormone positive control, present at a highest concentration of 11 pmoles per well, with a two-fold serial dilution performed. The ELISA data for both the indirect and DAS ELISAs is summarized in Table 20, below, that provides a summary of indirect and double antibody sandwich ELISA data. The indirect ELISA the response per pmole is reported relative to the CHO GDF8 prohormone positive control.

TABLE 20

Summary Of Indirect And Double Antibody Sandwich ELISA Data

| Designation | Direct ELISA | | | Sandwich ELISA | | |
|---|---|---|---|---|---|---|
| Shorthand descriptor | Goat #661 | Rabbit #1286 | Rat MAb | 135D C Goat 1° | 135D C Rat 1° | Rat C Goat 1° |
| TMV-FV5 DJ5(20)-U5-TPAT | + | ++++ | − | − | − | + |
| TMV-FV6 DJ5(12)-U1-N | ++ | ++++ | ++ | + | + | + |
| TMV-FV7 DJ5(12)-U1-GPAT | ++ | ++++ | ++ | ++++ | ++++ | ++++ |

For Table 20:
++++ indicates a comparable response to the GDF8 prohormone control. The primary antibodies employed are listed. For the sandwich ELISA, the highest response obtained was with the-FV7 construct, which was set to ++++. Data for the other fusions is reported relative to this.
C; capture antibody,
135D; PVAS-135D anti-TMV PAb;
1°, primary antibody.

For TMV-FV5 tested in direct ELISA format, the fusion titered in a manner similar to the GDF8 prohormone control when the Rabbit #1286 antibody was employed for detection. In comparison, only a minimal response was obtained when the Goat #661 or the Rat MAB788 antibodies were employed as the primary antibodies. In the sandwich ELISA format the responses were weak compared to TMV-FV7. However it should be noted that the PVAS-135D antibody employed for capture was raised against the U1 strain of TMV and TMV-FV5 is based on the U5 strain.

Both the 12 amino acid DJ5-derived peptide fusions (TMV-FV6 and TMV-FV7) were detected by all three anti-GDF8/DJ5 antibodies in the direct ELISA format and the response profiles for both fusions were similar, with the OD response per pmole being slightly higher for TMV-FV7. However, this may simply reflect the improved solubility of this fusion. With Rabbit #1286 detection, the response to both TMV-FV6 and-FV7 was comparable to the GDF8 prohormone control. In the case of the Goat #661 and Rat MAb, the response to the GDF8 prohormone control was 2-3 fold higher. For the double antibody sandwich ELISAs, the N-terminal fusion showed a poor response in all cases; possibly due to poor capture resulting from its aggregated state. For the C-terminal (GPAT) fusion, a response was obtained with both the Goat #661 and Rat MAB788 as primary antibodies, having captured with the PVAS-135D polyclonal. With anti GDF8 capture and detection (Rat MAB788 capture and Goat #661 detection), TMV-FV7 showed an OD response per pmol greater than the GDF8 prohormone control. This may reflect the fact that each captured rod displayed over 2000 copies of the reactive epitope, resulting in signal amplification. Together with the Western blot data discussed in Example 12, the ELISA data indicates that the 12 amino acid N-terminal portion of the 20 amino acid DJ5 epitope was recognized by neutralizing antibodies to the full GDF8 protein and therefore appears to be a viable vaccine candidate.

Example 15

Choice of TMV Coat Protein Fusion for Animal Testing and Vaccine Manufacture

A total of seven candidate recombinant TMV DJ5 fusions, detailed in Tables 8 and 12, were evaluated for their expression in *N. benthamiana* and their immunoreactivity to a series of antibodies directed against either the 20 amino acid DJ5 peptide or the full GDF8 prohormone. Based on the cumulative data the constructs listed in Table 21, below, were taken forward for manufacturing, in order to generate sufficient quantities of qualified, sterilized and inactivated recombinant virion, for testing in a series of animal trials.

TABLE 21

Four Recombinant TMV DJ5 Fusions Selected For The Manufacture Of Investigative Vaccines For Animal Testing

| Vector Designation | Shorthand descriptor | Coat protein backbone | Epitope insertion location |
|---|---|---|---|
| pLSB-FV1 | DJ5(20)-U1-GPAT | strain U1 | GPAT position |
| pLSB-FV5 | DJ5(20)-U5-TPAT | strain U5 | TPAT position |
| pLSB-FV6 | DJ5(12)-U1-N | strain U1 | N-terminus |
| pLSB-FV7 | DJ5(12)-U1-GPAT | strain U1 | GPAT position |

The reasoning behind this selection was as follows. The fusions displaying the 12 amino acid N-terminal region of the DJ5 peptide, namely TMV-FV6 and TMV-FV7, possessed the most desirable characteristics in terms of accumulation in plants, extraction and purification. Since the immunoreactivity analysis by Western blot and ELISA demonstrated that these modified DJ5 peptide TMV fusions were recognized by the Goat #661 and Rat MAB788 antibodies, which are GDF8 neutralizing, both were carried forward for vaccine manufacturing. To complement these two vaccines, the 20 amino acid DJ5 fusions considered were those that carried the epitope at either the N-terminus (TMV-FV3) or at the GPAT/TPAT position (TMV-FV1 and TMV-FV5). Owing to epitope truncation in the case of TMV-FV3 (see Example 10 and 11), TMV-FV1 and TMV-FV5 were chosen. This selection also permits vaccines of different physical forms to be compared, from soluble (TMV-FV7), through partially soluble (TMV-FV6 and TMV-FV5) to insoluble (TMV-FV1).

For the manufacturing of the four TMV DJ5 fusions for animal use, the procedures employed were as outlined in Example 10 and Example 12, with the following modifications. At all stages in the process, water for injection (WFI) was employed and all reagents were from dedicated stocks. Where possible laboratory ware used to process the virus preparations was baked at 225° C. for a minimum of 6 hours. In cases where this was not possible the laboratory ware was soaked in a 10% sodium hypochlorite solution for 20 minutes, rinsed extensively in WFI and autoclaved at 121° C. for 20 minutes.

The final recombinant virus was resuspended in sterile phosphate buffered saline. This preparation was sterilized and the TMV genomic RNA inactivated by treating with binary ethyleneimine ("BEI"). Briefly, a 0.1 M BEI stock solution was added to a final concentration of 5 mM BEI. Samples were incubated for 48 hours at 37° C. with constant mixing. After 48 hours, the BEI was neutralized by the addition of a 3 molar excess of sodium thiosulfate. The protein content of the BEI-inactivated TMV DJ5 fusion preparations was determined by amino acid analysis (AAA), the pH adjusted to approximately 7.4, by the addition of 10% v/v of a 50 mM monobasic potassium phosphate solution and the preparation diluted to 1 mg/mL with sterile phosphate-buffered saline before aliquoting into 2 mL sterile glass vials. The final vialed product was release tested as outlined by Example 16, below.

Example 16

Characterization of the TMV Coat Protein Fusion Vaccines for Animal Testing

The vialed vaccines TMV-FV1, TMV-FV5, TMV-FV6 and TMV-FV7 were subjected to a series of tests to confirm identity, purity, sterility, TMV genomic RNA inactivation and the absence of endotoxin. The assays and release criteria employed are outlined in brief below.

The molecular weight of each vaccine was determined by MALDI-TOF mass spectrometry and for release must match the expected MW within ±0.05%. All vaccines were analyzed by 16% Tris-glycine SDS-PAGE. After electrophoresis, gels were stained with Coomassie Brilliant Blue and analyzed densitometrically. The TMV DJ5 coat protein fusion band or bands must constitute 90% or higher of the total protein detectable. The identity of each vaccine was determined by tryptic digest MALDI-TOF mass spectrometry. The molecular masses for at least four unique, unmodified tryptic peptide fragments must match the molecular mass of the corresponding theoretical unmodified tryptic peptide fragments ±0.5 and the tryptic peptide fragments must confirm DJ5 peptide fusion integrity. The final protein concentration of the vaccine was determined using amino acid analysis, which also provided the amino acid composition of the TMV DJ5 fusions. The appearance of the vaccines in solution was determined by visual inspection and the pH of the vialed product was determined by standard methods using a calibrated pH meter (acceptable range, pH 7.4+/−0.4).

The TMV infectivity was determined using a local lesion host plant, *N. tabacum* var. *xanthi*, "Glurk". Local lesion assays were performed on Glurk plants 4-6 weeks post-sowing. One hundred µl of the sample to be assayed was inoculated per leaf with silicon carbide employed as an abrasive. Samples were run in triplicate and the local lesions were scored 4-6 days post-inoculation. Detection of less than one local lesion was required for release. For bioburden determination, the 10 µL and 100 µL samples were plated on LB nutrient agar, using aseptic technique under a laminar flow hood. The plates were inverted and incubated at room temperature for four days. The number of colonies was recorded after the four day incubation and the plates were then moved to a 33° C. incubator for a further 4 days and scored a second time. For release, no colony forming units must be detected. Finally, the endotoxin content of the vialed TMV DJ5 fusions was determined using the *Limulus Amebocyte* Lysate (LAL) assay. To meet specifications, each vaccine dose should deliver no more than 10 EU of endotoxin. The release testing results for the four vaccines is summarized by Tables 22A and 22B, below.

TABLE 22A

Release Testing Results For BEI-Treated DJ5 Fusion Vaccine Proteins

| Designation | SDS-PAGE (purity) | MALDI-Tof MS MW | pH | appearance | Protein Conc. (mg/mL) |
|---|---|---|---|---|---|
| TMV-FV1 | >90% | 19833 Pass | 7.4 | Opaque, White ppt | 0.95 |
| TMV-FV5 | >90% | Minor peak: 19875 Major peaks: Multiple truncations | 7.2 | Opaque, Tan/green tint | 0.98 |

TABLE 22A-continued

Release Testing Results For
BEI-Treated DJ5 Fusion Vaccine Proteins

| Designation | SDS-PAGE (purity) | MALDI-Tof MS MW | pH appearance | Protein Conc. (mg/mL) |
|---|---|---|---|---|
| TMV-FV6 | 95% | 18799 Pass | 7.1 Opaque, Tan/green tint | 0.83 |
| TMV-FV7 | 98.9% | 18981 Pass | 7.1 Opaque, Whitish | 1.05 |

TABLE 22B (Additional Data)
Release testing results for
BEI-treated DJ5 fusion vaccine proteins

| Designation | Protein Conc. (mg/mL) | Local lesion assay | Bio-Burden | LAL (endotoxin) EU/mL | Tryptic MALDI T of (identity) |
|---|---|---|---|---|---|
| TMV-FV1 | 0.95 | Pass | Pass | 0.845 | Pass |
| TMV-FV5 | 0.98 | Pass | Pass | 7.70 | Pass |
| TMV-FV6 | 0.83 | Pass | Pass | 3.32 | Pass |
| TMV-FV7 | 1.05 | Pass | Pass | 1.21 | Pass |

The results for the vaccine lots produced for animal testing were as follows. For TMV-FV1, a total of 24 vials were prepared (1 mL/vial), with a target protein concentration of 1 mg/mL. By PAGE analysis under reducing conditions, there appeared to be a reduction in the monomer level present in the purified vaccine following the BEI treatment. This may possibly be due to increased disulfide bond formation caused by the high pH conditions employed in BEI inactivation. To determine if the BEI treatment affected the fusion antigenicity, Western blots were performed on both the pre- and post-BEI treated samples using the following antibodies; PVAS 135D (anti-TMV), Goat #661, Rabbit #1286 and rat MAB788. The profiles observed with all four antibodies were essentially identical, with both the pre- and post-BEI samples containing the expected oligomeric ladder. ELISAs were not performed due to the particulate nature of the purified fusion. The quality analysis for the vialed TMV-FV1 was completed and the release data is summarized in Tables 22A and 22B. The fusion passed all the release criteria. In the case of purity, this was estimated at greater than 90%, based on the one to one correspondence between the PAGE gel and Western blot oligomeric profiles. However, an exact percent purity was not reported, as tryptic digest confirmation of each individual band was not performed.

For TMV-FV5, a total of 9 vials were prepared (1.4 mL/vial), with a target protein concentration of 1 mg/mL. To determine if there were any detrimental effects of the BEI treatment on the fusion, Western blots were performed using the GDF8 neutralizing rat MAB788 for detection. For the pre-BEI treatment sample, a single band was observed. However, after BEI treatment an oligomeric ladder was present, possibly due to increased disulfide cross-linking, which may be the result of the alkaline pH conditions during BEI treatment. Also, for the post-BEI monomer species a doublet was evident by Western blot. The Western blot data correlated with the full-length MALDI data, which showed a product with multiple truncations. Both bands of the doublet are reactive to the antibody, suggesting the truncated product retained some antigenicity. Direct ELISAs were performed on the samples with the three anti-DJ5/GDF8 antibodies (Goat #661, Rabbit #1286 and rat MAB788) and one anti-TMV antibody (PVAS 135D). The pre-BEI samples were substantially more reactive than the BEI-treated final product. A possible explanation for this is that the cross-linking of the TMV fusion reduced epitope accessibility and/or reduced solubility of the virions, resulting in a lowered coating level on the microtiter plate. The quality analysis for the vialed TMV-FV5 was completed and the release data is summarized in Tables 22A and 22B. In the case of purity, this was estimated at greater than 90%, based on the one to one correspondence between the PAGE gel and Western blot oligomeric profiles. However, an exact percent purity was not reported, as tryptic digest confirmation of each individual band was not performed. As noted above, the truncation species in the BEI-treated final product was immunoreactive by Western blot. In addition, gel and liquid typtic mass mapping indicated that the truncated species retained all of the DJ5 epitope except the C-terminal two amino acids (MS). Therefore, this vaccine candidate was carried forward for animal testing.

For TMV-FV6, a total of 9 vials were prepared (1.4 mL/vial), with a target protein concentration of 1 mg/mL. To determine if there were any detrimental effects of the BEI treatment on the fusion, Western blots were performed, on the pre- and post-BEI samples, using the GDF8 neutralizing Rat MAb for detection. A single band was observed for both samples. Direct ELISAs were also performed with the three anti-DJ5/GDF8 antibodies and one anti-TMV antibody. Similar profiles were observed for both the pre- and post-BEI samples. Together with the Western blot data, these results indicate no detrimental modifications to the epitope following BEI treatment. Tables 22A and 22B summarize the release data from the quality analysis for the vialed TMV-FV6. The vaccine product passed all release criteria and was carried forward for animal testing.

For TMV-FV7, a total of 32 vials were prepared (1 mL/vial), with a target protein concentration of 1 mg/mL. To determine if the BEI treatment had any detrimental effects on the DJ5 fusion, Western blots were performed, using the following antibodies; PVAS 135D (anti-TMV), Goat #661, Rabbit #1286 and rat MAB788. Both the pre- and post-BEI samples were detected by all four antibodies and the fusion migrated as a single band. In addition, since this fusion was soluble, both direct capture ELISAs and double-antibody sandwich (DAS) ELISAs were performed, to determine if alterations to the epitope, resulting from BEI treatment, could be detected in the context of the undenatured coat protein and assembled virion. CHO-derived GDF8 prohormone (Example 1) was employed as a positive control. For the DAS ELISAs, nearly identical profiles were obtained for both the pre- and post-BEI treatment samples, indicating that the BEI treatment has minimal impact on the product's antigenicity. Similarly, for the direct capture ELISAs, the BEI treated product was comparable to the untreated fusion, and for three of the four antibodies the post-BEI treatment sample gave a slightly higher OD reading. The quality analysis for the vialed product was completed and TMV-FV7 passed all release criteria (Tables 22A and 22B) and could therefore be carried forward for animal testing.

Example 17

Stability Study for TMV-FV1, TMV-FV5, TMV-FV6 And TMV-FV7 with Storage at 4° C. for 6 Months The four BEI-treated and vialed TMV DJ5 fusions were subjected to a stability study of 6 month duration, to evaluate the candidate vaccines integrity with storage at 4° C. The 6 month time period covered the time frame over which the vaccines were evaluated in the animal studies. A total of six timepoints were taken, at approximately one month intervals and the vialed vaccines were analyzed by PAGE gel, Western blot and MALDI-Tof mass spectrometry. For the Western blot analysis, the anti-GDF8 Goat #661 antibody was employed. The PAGE analysis and Western blot data for the 6 month timepoint is summarized in Table 23 and the MALDI-Tof mass spectrometry information for all timepoints is summarized in Table 24.

poorly to the membrane. In the case of TMV-FV5, the monomer species was a doublet in the release sample as noted in Example 16. Over the course of the stability study a gradual shift to the lower molecular weight species in the monomer doublet was observed by PAGE analysis. However, both monomeric species retained immunoreactivity by Western blot over the six month window of analysis. The higher molecular weight oligomeric species of TMV-FV5 were also evident by Western blot. However, for the six month timepoint only the TMV-FV5 putative dimer was visible by Western blot, possibly due to poor transfer: 4 to 6 bands were typically detected.

Table 24, below, provides MW MALDI analysis for the release sample (R) and for the six samples taken throughout the stability study for the BEI-treated and vialed vaccines. For the release sample, only the major peak is reported.

TABLE 24

MW MALDI Analysis

| | Expected | | Observed MW (Da) (Timepoint #) | | | | | | |
|---|---|---|---|---|---|---|---|---|---|
| Designations | MW (Da) | Modifications | R | 1 | 2 | 3 | 4 | 5 | 6 |
| TMV-FV1 | 19833 | Met cleaved, Ser acetylated | 19833 | 19842 | 19993 | 20023 | 20006 | 20037 | 19997 |
| TMV-FV5 | 19878 | None | 19875 | 19066 17723 | 19032 17719 | 19142 17830 | 19243 17717 | 19157 17718 | 19227 17719 |
| TMV-FV6 | 18794 | Met cleaved, Val not acetylated | 18799 | 18797 18841 | 18795 18838 | 18792 18836 | 18795 18838 | 18794 18837 | 18795 18838 |
| TMV-FV7 | 18981 | Met cleaved, Ser acetylated | 18981 | 18986 19024 | 18984 19027 | 18984 19029 | 18985 19027 | 18985 19029 | 18985 19028 |

Specifically, Table 23, below, provides a summary of PAGE analysis and Western blot analysis of the DJ5 peptide coat protein fusions stored at 4° C. The data is for the final time point of the six-month study.

TABLE 23

Summary of PAGE And Western Blot Analysis

| Designation Shorthand descriptor | PAGE profile | Western blot detection Anti-GDF 8 |
|---|---|---|
| TMV-FV1 DJ5(20)-U1-GPAT | Oligomeric ladder (7 to 9 bands) | Yes (5 to 6 bands) |
| TMV-FV5 DJ5(20)-U5-GPAT | Oligomeric ladder (5 to 6 bands) | Yes (2 bands) |
| TMV-FV6 DJ5(12)-U1-N | Major band at ~21 kDa. Minor 40 kDa band | Yes Single band ~21 kDa |
| TMV-FV7 DJ5(12)-U1-GPAT | Major band at ~23 kDa. | Yes Single band ~23 kDa |

For TMV-FV6, TMV-FV7 and TMV-FV1, the PAGE profile was maintained throughout the course of the six month stability study. Similarly for the Western blot profile, no deviations were observed relative to the release samples. The difference in band number detected by Western blot, relative to the PAGE profile, corresponds to the higher molecular weight bands (greater than 200 kDa), which transferred Mass spectrometry analysis (Table 24, above) indicated that the full-length species, with the noted modifications, was present for both TMV-FV6 and TMV-FV7 and an additional major peak, corresponding to the addition of one BEI to the coat protein, was also detected. These two species were maintained throughout the stability study. For TMV-FV1, the principal peak in the majority of the spectra (timepoints 3 to 6) was approximately 170 Da greater than expected. This corresponds to the addition of 4 or 5 BEI moieties per coat protein. However, it should be noted that the spectra quality for the TMV-FV1 samples was poor. In the case of pLSB-FV5, minimal full length species was detected after timepoint one. The two principal species observed had approximate molecular weights of 19130+/−100 Da and 17719 Da. The release sample for TMV-FV5 did contain a 19038 Da species that was positively identified and shown to possess the majority of the 20 amino acid DJ5 epitope (Example 16). The 17719 Da species represents a species only 2 to 3 amino acids larger than TMV U5 (17,489 Da, Met cleaved) and therefore does not correspond to the lower band in the monomer doublet, suggesting that this is 19,130+/−100 Da species. By Western blot this 19.1 kDa species retained immunoreactivity.

Overall the data indicates that TMV-FV1, TMV-FV6 and TMV-FV7 were stable for at least 6 months with storage at 4° C. In the case of TMV-FV5, degradation did occur with storage at 4° C., to yield a principle species with an approximate molecular weight of 19.1 kDa. This truncation product appeared stable with storage and from the Western blot data was immunoreactive with the GDF8 neutralizing Goat #661 antibody.

Example 18

Refinement in the DJ5 Peptide Region Capable of Binding a GDF8 Neutralizing Antibody During the course of the Western blot analysis, the GDF8 neutralizing rat monoclonal antibody (MAB788) was determined to react strongly with the U1 coat protein. The observed response appeared comparable to TMV-FV7, when this fusion was analyzed in parallel. In contrast, the goat #661 polyclonal sera, which is also GDF8 neutralizing, reacted only weakly with the U1 control. When the U5 strain coat protein was included in the Western blot analysis, no cross-reactivity was detected with the rat MAB788 antibody. This result prompted a comparison of the rat monoclonal antibody reactivity to the U1 and U5 coat proteins by indirect ELISA (Table 25). For this ELISA, the rat MAB788 was initially diluted at 1:20; no cross-reactivity against the U5 coat protein was detected, supporting the Western blot data, while the U1 coat protein was detected with an end-point dilution of 1:1620. The response against the TMV DJ5 peptide fusion positive control (TMV-FV7) was 3-fold higher. In the indirect ELISA, the virion was adsorbed to the ELISA plate surface, a step that is expected to result in some disruption of the virus structure.

Since a clear difference in rat MAB788 reactivity was observed between TMV U1 and the TMV-FV7 in ELISA format, while the reactivity by Western blot was comparable, it was hypothesized that the putative TMV U1 epitope detected by the rat monoclonal antibody was internal to the virus structure. To test this hypothesis, a double antibody sandwich ELISA was performed (Table 25), where either TMV U1 or TMV-FV7 was displayed as an intact virion, through capture by an anti-TMV polyclonal antibody. In contrast to the ELISA against the adsorbed TMV U1, there was minimal cross-reactivity to the wild-type U1 virus when presented as an intact virion, indicating that the reactivity against TMV-FV7 virion was specific for the displayed DJ5-derived epitope. This result supported the hypothesis that the putative U1 epitope was not surface exposed in the intact virion.

Table 25, below, provides endpoint dilution results for indirect and DAS ELISAs, to compare the reactivity of the anti-GDF8 rat monoclonal (MAB788) and the goat #661 polyclonal antibodies to the TMV U1 coat protein and the U5 coat protein, as follows.

TABLE 25

Endpoint Dilution Results For Indirect And DAS ELISAs

| | Indirect ELISA | | | DAS ELISA (PVAS-135D capture antibody) | | |
|---|---|---|---|---|---|---|
| | Primary Antibody | | | Primary antibody | | |
| Coating antigen | Goat #661 | Rat MAb | Virion captured | Goat prebleed | Goat #661 | Rat MAb |
| TMV U1 | 60 | 1,620 | TMV U1 | 180 | 540 | 180 |
| TMV-FV7 | 4,860 | 4,860 | TMV-FV7 | 180 | 14,580 | 14,580 |
| TMV U5 | 60 | <20 | | | | |

For Table 25, TMV-FV7 was included as a positive control. For the DAS ELISA, the TMV U1 or TMV-FV7 virion was captured using the anti-TMV polyclonal antibody PVAS 135D. As a negative control, goat prebleed sera was employed. For all the ELISAs, the antigen was employed at 5 µg/mL. The rat and goat antibodies were initially diluted at 1:20 and a three-fold serial dilution performed for each, in duplicate. The endpoint dilution was taken as the highest dilution at which the OD reading was at twice background.

Due to the stark difference in the rat MAB788 reactivity against the U1 and U5 TMV coat proteins, an alignment of the two coat protein sequences with the N-terminal 12 amino acids of the DJ5 peptide was performed (FIG. 6B). This alignment showed that the DJ5 peptide and the U1 coat protein share a common four amino acids sequence, QANP (SEQ ID NO: 58), that is disrupted in the case of the U5 coat protein by the presence of a proline. From the virus X-ray diffraction structure, QANP (residue 329 to residue 332 of natural, human precursor GDF8), is located on the inner surface of the virion (FIG. 6C), in agreement with the Western blot and ELISA data discussed. Overall, this data provides an explanation for the observed rat MAB788 cross-reactivity with the U1 coat protein, and aids in delineating an essential and necessary amino acid sequence within the DJ5 peptide, to which neutralizing antibodies can be raised.

Interestingly, the goat #661 polyclonal antibodies show minimal reactivity to the U1 coat protein in both a Western blot and indirect ELISA format. Similar to the rat monoclonal, this antibody is capable of neutralizing GDF8 in an in vitro transcription activation assay (Example 3). Since the Goat #661 sera reacts strongly with TMV-FV7, this may indicate that there are other regions within the N-terminal 12 amino acids of the DJ5 peptide that are capable of generating GDF8 neutralizing antibodies.

Example 19

Superiority of DJ5 Peptide Display in the Context of a Molecular Fusion to TMV Compared to Chemical Fusion to Keyhole Limpet Hemocyanin (KLH)

During the initial investigative studies, which identified the DJ5 peptide, the GDF8 neutralizing rat monoclonal (MAB788, R&D systems) and Goat #661 antibodies were compared to two rabbit-derived hyper immune sera (Table 26). The rabbit antibodies were raised against KLH conjugates of either the SP2 or DJ5 peptide. FIG. 7 indicates that the SP2 peptide contains the QANP (SEQ ID NO: 58) residues at its C-terminus. The rat MAB788 cross-reactivity with the U1 coat protein (Example 18) provided strong evidence of the importance of the QANP (SEQ ID NO: 58) residues in generating a neutralizing response. However, neither rabbit sera was capable of GDF8 neutralization, although they did recognize their respective peptide immunogens in ELISA format. Also of interest is the relative response of the Goat #661 and rat MAB788 to the peptides in ELISA format. Neither antibody detected the DJ4 peptide, in which the proline residue of QANP (SEQ ID NO: 58) was absent (FIG. 7), while they were weakly reactive to SP2 and reactive to the DJ5 epitope. In contrast, the rabbit #92 sera (SP2 peptide antigen), was reactive to DJ4 and unreactive to DJ5. This suggests that the context in which this region of GDF8 is displayed may be important for the generation of a neutralizing response.

Table 26, below, provides a summary of relative ELISA reactivity and GDF8 neutralization for a selection of commercial and in house-generated antibodies.

TABLE 26

Summary Of Relative ELISA Reactivity And GDF8 Neutralization

| Antibody | Antigen* | ELISA reactivity | | | GDF8 neutralization |
|---|---|---|---|---|---|
| | | DJ5 | SP2 | DJ4 | |
| Goat #661 | CHO-proGDF8 | (++) | (+) | (−) | (+) |
| Rat MAB788 | NOS-proGDF8 | (++) | (+) | (−) | (+) |
| Rabbit #92 | Peptide SP2** | (−) | (++) | (++) | (−) |
| Rabbit #1286 | Peptide DJ5** | (++) | ND | (+) | (−) |

*GDF8 mature region = human/pig/chick/rat amino acid sequence. proGDF8 = GDF8 prohormone human amino acid sequence.
**peptides coupled to KLH.

To further investigate the differences in the Goat #661, rat MAB788 and Rabbit #1286 antibodies, a series of ELISAs were performed against the following targets:

- The DJ5 (20) peptide conjugated to BSA (BSA-DJ5 (20), see FIG. 7).
- The DJ5 (12) peptide conjugated to BSA (BSA-DJ5 (12), see FIG. 7).
- The DJ5 (8) peptide conjugated to BSA (BSA-DJ5(8), see FIG. 7).
- BSA alone.
- TMV-FV7, which displays DJ5(12) as a GPAT fusion to the U1 coat protein. The virions were presented as intact rods in a double antibody sandwich format, employing the rabbit anti-TMV U1 polyclonal PVAS 135D.
- proGDF8FLAG, a mammalian cell produced and affinity purified GDF8.

Table 27, below, provides a summary of the ELISA coatings and the estimated pmoles of DJ5 peptide present per well.

TABLE 27

Summary Of The ELISA Coatings

| Plate Coating | Protein concentration (μg/mL) | Volume (μL) | Peptide MW (Da) | Carrier or Fusion or GDF8 MW (Da) | pmoles DJ5 peptide[c] |
|---|---|---|---|---|---|
| DJ5 (20) BSA[a] | 5 | 50 | 2040 | 67,000 | 131 |
| DJ5 (12) BSA[a] | 5 | 50 | 1190 | 67,000 | 131 |
| DJ5 (8) BSA[a] | 5 | 50 | 850 | 67,000 | 131 |
| BSA | 5 | 50 | | 67,000 | 0 |
| PVAS 135D --FV7 | 5 | 50 | | 18,981 | 13[d] |
| proGDF8FLAG[b] | 5 | 50 | | 50,000 (80%) 12,500 (20%) | 8 (20[e]) |

[a]BSA possesses a total of 59 lysine ε-amine groups (with only 30-35 of these typically available for derivatization). For the glutaraldehyde conjugation reactions, the peptide was present in a 2-fold molar excess and it was assumed that all free lysines were loaded, i.e. 35 displayed peptides per BSA molecule.
[b]For the CHO-derived proGDF8FLAG (FLAG tagged GDF8 prohormone), the purified material was a heterogeneous mixture of the 50 kDa propolypeptide and the fully processed 12.5 kDa GDF8 in an 80:20 ratio.
[c]In calculating the pmoles of the target antigen adsorbed per well, it was assumed that all the protien present in the coating solution bound to the plate. For all antigens, 250 ng was present in the coating solution and the Nunc MaxiSorp plates employed have an adsorption capacity of 500-600 ng IgG/cm$^2$, and 0.6 cm$^2$ of surface area was in contact with the coating solution.
[d]Assumes that all of the TMV-FV7 added to the well was captured by the coating PVAS 135D antibody.
[e]Theoretical maximum pmoles of GDF8 coated per well, were the GDF8 prohormone 100% processed to the 12.5 kDa species.

Table 28, below, provides an ELISA endpoint dilution comparison of the Goat #661, Rabbit #1286 and rat MAB788 antibodies, in terms of their reactivity to a series of DJ5-derived peptide-BSA conjugates, the GDF8 prohormone (proGDF8FLAG) and TMV-FV7 (displayed in a double antibody sandwich format).

TABLE 28

ELISA Endpoint Dilution Comparisons

| Coating antigen | Primary antibody employed | | |
|---|---|---|---|
| | Goat #661 | Rabbit #1286 | Rat MAB788 |
| BSA-DJ5 (20) | 2,430 | 81,000 | 270 |
| BSA-DJ5 (12) | 90 | 27,000 | <10 |
| BSA-DJ5 (8) | 90 | 27,000 | <10 |
| BSA alone | 10 | <1,000 | <10 |
| PVAS 135D-TMV-FV7 (DAS) | 7,290 | ND | 7,290 |
| proGDF8FLAG | 21,870 | 27,000 | 21,870 |

It should be noted that no TMV U1/PVAS 135D double antibody sandwich was present as a negative control, however, Table 25, supra, shows that when presented as a virion, there is minimal reactivity against the U1 coat protein by either the rat MAB788 or the goat #661 antibodies. For the Table 28 data, the goat #661 and rat monoclonal MAB788 antibodies were initially diluted at 1:10 and a three-fold serial dilution performed for each in duplicate. For the purified rat monoclonal, a 1:10 dilution corresponded to an antibody concentration of 50 μg/mL. In the case of the Rabbit #1286 antibody, the initial dilution was 1:1000. The endpoint dilution was taken as the highest dilution at which the OD reading was at twice background. ND, not determined as a rabbit polyclonal was employed for virion capture.

For the rat monoclonal antibody, there was weak reactivity to the full DJ5 peptide conjugated to BSA, DJ5(20), however, neither of the shorter DJ5-derived peptides were detected. In contrast, for the GDF8 prohormone, which displayed approximately 10-fold lower levels of the DJ5 peptide per well (relative to DJ5(20) BSA), the endpoint dilution was 2 log$_{10}$ higher. Also, there was strong reactivity to TMV-FV7, with an endpoint dilution only 3-fold lower than for the GDF8 prohormone. For TMV-FV7, 13 pmoles was determined to be the maximum DJ5 content per well, approximately twice the GDF8 value, however, this assumes 100% capture of the virion by the coating antibody.

The stark difference in the rat MAB788 reactivity to TMV-FV7 versus the DJ5(12) BSA conjugate is of particular interest, because the same peptide was displayed in both cases. For DJ5(12), glutaraldehyde conjugation to BSA is via the primary amino group of the peptide's N-terminus. This may sterically hinder accessibility to the QANP (SEQ ID NO: 58) residues of the peptide (FIG. 7). This is supported by the fact that the DJ5(20) peptide is detected, albeit weakly. For DJ5 (20), a lysine (K) is present in the C-terminal region of the peptide and is an alternative conjugation site that should result in improved display of the peptide's N-terminal region. An alternative explanation is that the presentation of the QANP (SEQ ID NO: 58) residues in the context of a molecular fusion to the TMV coat protein allows the epitope to adopt a more "native" conformation. The latter hypothesis is supported by the GDF8 neutralization data presented in Table 26, supra. Table 26 indicates that the SP2 and DJ5 peptides, conjugated to KLH, failed to generate GDF8 neutralizing antibodies, although for both the QANP (SEQ ID NO: 58) region should have been adequately displayed, owing to its location relative to the peptide N-terminus and/or to the reactive lysines (FIG. 7). However, when the DJ5 peptide was displayed in the context of TMV a strong immune response was observed in both goat and swine (see Examples 20 and 21) and the sera was GDF8 neutralizing, based on an in vitro transcription assay For the goat #661 antibody, the overall response profile against the different target antigens was qualitatively similar to the rat MAB788 monoclonal. However, the difference in response between the DJ5(20)-BSA conjugate and the GDF8 prohormone was 1 $\log_{10}$ lower than for the rat monoclonal, owing to the 10-fold higher endpoint dilution against DJ5 (20)-BSA. In addition, the goat #661 antibodies were weakly reactive with the DJ5(12) and the DJ5(8) peptide BSA conjugates, although the endpoint dilution against TMV-FV7 was still 2 $\log_{10}$ higher than for DJ5(12)-BSA. For the rabbit #1286 polyclonal, raised against a DJ5(20)-KLH conjugate, the endpoint dilution was greatest for the DJ5(20)-BSA conjugate, while the response to the GDF8 prohormone, DJ5 (12)-BSA and DJ5(8)-BSA were similar. In the case of Rabbit #1286, no endpoint dilution data was available for TMV 2264 as a target, as the capture antibody employed in the sandwich was rabbit-derived.

The results with the GDF8 neutralizing goat #661 antibody further support the hypothesis that the display of peptides from the DJ5 region in the context of a molecular fusion permits the peptide to adopt an appropriate conformation for the generation of neutralizing antibodies. From the rabbit #1286 data, it is clear that the KLH peptide conjugate was a potent immunogen, however, the inability of this polyclonal to neutralize GDF8 suggests that the peptide failed to adopt the appropriate conformation when presented in the context of a glutaraldehyde conjugate.

Example 20

Serological Analysis of Bleeds from Goats Following Immunization with TMV 2665, TMV-FV5, TMV-FV6, TMV-FV7 or the Pro GDF8 Protein In order to measure the immunogenicity of the above-described TMV fusion vectors, two additional studies were performed with goats. Each study was identical except for the location: one was performed under our direction by ProSci, Inc. (Goat study #1) and the other was performed in house and was blinded (Goat Study #2). Adult dairy goats were used for each study. Each study was performed as follows:

Goats were vaccinated with 2 mL of vaccine as shown in Table 29, below. The first vaccine (day 0), contained Complete Freund's Adjuvant, whereas subsequent vaccine doses contained Incomplete Freund's Adjuvant. The first vaccination was given subcutaneously (SQ) on the right side of the neck. Subsequent vaccinations alternated between right and left sides of the neck. Blood samples were collected from animals by venipuncture of the jugular veins using evacuated SST blood collection tubes on days 0, 28, 49, 63, 77 and 91. Blood was allowed to clot for a minimum of two hours at room temperature, centrifuged and the serum collected. Serum samples were labeled with animal number, type of specimen, date collected, and study number. Serum was stored at −10° C., or colder, until assayed.

TABLE 29

Experimental Set-up For Goat Study #1 and Goat Study #2

| Group | No. of Animals | Test Product Identification | Dose (µg) | Adjuvant | Injection Route | Location | Treatment Days |
|---|---|---|---|---|---|---|---|
| 1 | 2 | proGDF8 P2 Cterm | 250 | Freund's | SQ | Neck (alternating) | 0, 21, 42, 70 |
| 2 | 2 | TMV-FV1 | 250 | Freund's | SQ | Neck (alternating) | 0, 21, 42, 70 |
| 3 | 2 | TMV-FV5 | 250 | Freund's | SQ | Neck (alternating) | 0, 21, 42, 70 |
| 4 | 2 | TMV-FV6 | 250 | Freund's | SQ | Neck (alternating) | 0, 21, 42, 70 |
| 5 | 2 | TMV-FV7 | 250 | Freund's | SQ | Neck (alternating) | 0, 21, 42, 70 |

The vaccines tested, together with their physical forms were:

| | |
|---|---|
| GDF8 P2-Cterm (P2) | soluble globular protein |
| TMV-FV1 | insoluble precipitate |
| TMV-FV5 | mixture of soluble and precipitated virions |
| TMV-FV6 | aggregated virion rods |
| TMV-FV7 | soluble virion rods |

For Goat study #1, animals were bled prior to the first vaccination ("pre-bleed") and sera taken one week after the third vaccination ("bleed 1"), and two weeks after the third vaccination ("bleed 2") were analyzed by ELISA. For the ELISAs, the following targets were employed:

Tobacco mosaic virus (type U1 or U5, corresponding to vaccine TMV scaffold) coated directly.

Tobacco mosaic virus (type U1 or U5, corresponding to vaccine TMV scaffold) displayed as intact rods in a double antibody sandwich (DAS) format, employing the rabbit anti TMV U1 polyclonal PVAS 135D.

The DJ5 (20) peptide conjugated to BSA (see FIG. 7).

The DJ5 (12) peptide conjugated to BSA (see FIG. 7).

The DJ5 (8) peptide conjugated to BSA (see FIG. 7).

CHO expressed and purified FLAG tagged GDF8 prohormone.

For the indirect TMV ELISAs, 50 µL of TMV U1 or TMV U5, diluted to 5 µg/mL in carbonate/bicarbonate buffer (pH 9.6) was used to coat 96-well microtiter plates (MaxiSorp, Nunc) overnight or over the weekend at 4° C. The coating solution was removed and the plates blocked with 100 mM Tris (pH 7.5), containing 0.5% v/v TWEEN™ 20, and 2% w/v BSA for 2 hours at room temperature (200 µL blocking solution per well). The wells were washed twice with 1×TBST buffer (Tris-buffered saline with TWEEN™ 20) and 50 µL of goat serum, diluted in 1×PBS with 2% w/v BSA was added per well. A three-fold serial dilution for each serum was employed starting at an initial dilution of 1:50. The GDF8 P2-Cterm pre-bleed serum was employed as a negative control on all plates.

Following a one-hour incubation at room temperature with the sera, the plates were washed with 0.9% w/v sodium chloride, 2% v/v Triton® X-100, using a microtiter plate washer (Skatron Instruments). 50 µL of rabbit anti-goat HRP conjugated secondary antibody (Pierce) was added at a dilution of 1:10,000 in 1×PBS containing 2% w/v BSA. The plates were incubated for one hour at room temperature, washed with the plate washer, and 50 µL of 3,3', 5,5'-tetramethyl bezidine substrate solution was added per well. The HRP catalyzed reaction was permitted to proceed for 5 to 20 minutes and was stopped by the addition of 50 µL of 1 N sulfuric acid. The plate absorbance (OD) was read at 450 nm in a 96-well plate Spectrophotometer (Molecular Devices).

For the double antibody sandwich (DAS) ELISA, 50 µL of anti-TMV polyclonal antibody PVAS-135D, diluted at 1:4000 in carbonate/bicarbonate buffer (pH 9.6) was used to coat 96-well microtiter plates (MaxiSorp, Nunc) overnight or over the weekend at 4° C. The coating solution was removed and the wells were blocked with 200 µL of 100 mM Tris (pH 7.5), containing 0.5% v/v TWEEN™ 20, 2% w/v BSA for one hour at room temperature. Following the blocking step, the wells were washed twice with 1×TBST buffer and 50 µL of either TMV U1 or TMV U5, diluted to 5 µg/mL in 1×PBS containing 2% w/v BSA, was added per well. The plates were incubated for one hour at room temperature, then washed with 0.9% w/v sodium chloride, 2% v/v Triton® X-100 using a microtiter plate washer (Skatron Instruments). The addition and dilution of the goat sera, addition of the secondary antibody and development of the ELISA plate were performed according to protocol outlined for the indirect TMV ELISAs.

To determine the reactivity of the Goat Study #1 serum to CHO-derived GDF8 prohormone, ELISAs were performed by directly coating the plates with the GDF8 prohormone. The GDF8 was diluted to 5 µg/mL in carbonate/bicarbonate buffer (pH 9.6) and 50 µL per well was employed to coat 96-well microtiter plates (MaxiSorp, Nunc) overnight at 4° C. All subsequent steps in the ELISA protocol were as outlined for the indirect TMV ELISAs.

For the ELISAs against the DJ5 peptides (FIG. 7), the three peptides, DJ5(20), DJ5(12) and DJ5(8) were conjugated to the carrier BSA. Briefly, the peptides were resuspended in 50% DMSO at 1 mg/mL and were combined with BSA and glutaraldehyde to give final concentrations of 1 mg/mL BSA and 1% glutaraldehyde for all conjugation reactions. The final concentrations of the peptides in the different reactions were: DJ5(8), 1 mg/mL; DJ5(12), 1.4 mg/mL; and DJ5(20), 2.6 mg/mL. The reactions were rotated at 4° C. overnight and subsequently dialyzed against 1×PBS to remove any unreacted peptide. Conjugation was confirmed by PAGE analysis on a 10-20% Tris-Glycine gel. Microtiter plates (96 well) were coated overnight at 4° C. with each of the three DJ5 peptide-BSA conjugates, diluted to 5 µg/mL in carbonate/bicarbonate buffer (pH 9.6). Following the microtiter plate coating, the ELISAs were performed following the procedures outlined for the indirect TMV ELISAs.

The anti-TMV response data for Goat Study #1 is summarized in tabular format in Table 30. As expected no response to TMV was observed in the P2 vaccinated animal. For the TMV peptide fusion vaccines, a 2 to 3 $\log_{10}$ increase in anti-TMV serum endpoint dilution was observed for the majority of the vaccines in both the indirect and DAS ELISA format. In the case of the TMV-FV5 vaccinated animal, the DAS response was notably lower. This may simply reflect poor capture of the TMV U5 virus by the PVAS 135D antibody, a polyclonal antibody raised against TMV U1. Following the third vaccination, the anti-TMV response appeared highest in the TMV-FV6 vaccinated animal with the lowest response in the TMV-FV1 vaccinated animal. This difference may be attributable to the different vaccine forms: TMV-FV6 exists as intact partially soluble virion that aggregates in solution, whereas TMV-FV1 is an insoluble precipitate in which the rod-like structure of TMV is likely compromised. Table 30, below, provides a summary of the endpoint dilution data for the anti-TMV indirect and double antibody sandwich (DAS) ELISAs, testing sera from goat study #1.

TABLE 30

Endpoint dilution Data From Goat Study #1
Anti-TMV Indirect And Double Antibody Sandwich (DAS) ELISAs

|  |  | Indirect ELISA | | | DAS ELISA | | |
| --- | --- | --- | --- | --- | --- | --- | --- |
| Vaccine | Capture antigen | Pre-bleed | Bleed 1 | Bleed 2 | Pre-bleed | Bleed 1 | Bleed 2 |
| U1 control | TMV U1 | 150 | 50 | 50 | 450 | 150 | 150 |
| U5 control | TMV U5 | 50 | (—) | 150 | 450 | 150 | 150 |
| P2 | TMV U1 | 50 | 50 | 50 | 150 | 1350 | 150 |
| TMV-FV1 | TMV U1 | 50 | 12,150 | 4,050 | 150 | 12,150 | 36,450 |
| TMV-FV5 | TMV U5 | (—) | 36,450 | 12,150 | 450 | 4,050 | 4,050 |
| TMV-FV6 | TMV U1 | 50 | 109,350 | 36,450 | 150 | 109,350 | 109,350 |
| TMV-FV7 | TMV U1 | 50 | 36,450 | 36,450 | 150 | 36,450 | 36,450 |

For the data presented by Table 30, Bleed 1 and Bleed 2 were taken 7 and 14 days after the third vaccination respectively. Sera were initially diluted at 1:50 and a three-fold serial dilution performed for each bleed in duplicate. The endpoint dilution was taken as the highest dilution at which the OD reading was at twice background. (–), indicates that the OD reading was below twice background. The U1 control and U5 control represent wells containing TMV U1 or TMV U5 respectively, which were probed with P2 prebleed sera and were present on all plates to account for any plate-to-plate variability in the background.

The results for the peptide specific ELISAs for sera from Goat Study #1, employing the 20 amino acid DJ5 epitope, together with peptides of the 12 N-terminal and 8 C-terminal amino acids, are summarized in Table 31. For the 20 amino acid DJ5 peptide ELISA, the immune response generated by the TMV peptide fusion vaccines paralleled very closely the observed anti-TMV U1 response, with the TMV-FV6 vaccine producing a 2.5 $\log_{10}$ increase in serum endpoint dilution compared to the 1 $\log_{10}$ increase with the TMV-FV1 vaccine. The response generated by immunization with the GDF8 protein was comparable to that of the TMV-FV1 vaccine. When the 12 amino acid N-terminal region of DJ5 was employed as the capture antigen, the response profile across the sera was comparable to that obtained with the full DJ5 peptide (DJ5(20)), although the endpoint dilutions were approximately 1 $\log_{10}$ lower. In contrast, the response to the C-terminal 8 amino acid region of DJ5 was minimal for all vaccines. This data supports the hypothesis that the putative neutralizing epitope of DJ5 is located in the N-terminal region of the peptide. The 1 $\log_{10}$ difference in the endpoint dilutions against the DJ5(20) versus the DJ5(12)-BSA conjugates may be attributable to epitope accessibility, as discussed in Example 19. Table 31, below provides a summary of the endpoint dilution data for the anti-DJ5 indirect ELISAs, testing sera from Goat Study #1.

TABLE 31

Endpoint Dilution Data From Goat Study #1
Anti-GDF8 ELISAs

|  | Pre-bleed | Bleed 1 | Bleed 2 |
| --- | --- | --- | --- |
| P2 | 150 | 36,450 | 36,450 |
| TMV-FV1 | 150 | 4,050 | 1,350 |
| TMV-FV5 | 150 | 12,150 | 1,350 |
| TMV-FV6 | 150 | 36,450 | 36,450 |
| TMV-FV7 | 150 | 12,150 | 4,050 |

For the data presented by Table 31, the amino acid sequences for the peptides conjugated to BSA (DJ5(20), DJ5(12) and DJ5(8)) are illustrated in FIG. 7. The well-coating conditions for the three peptide BSA conjugates were as described in Table 27, supra. Bleed 1 and Bleed 2 were taken 7 and 14 days after the third vaccination, respectively. Sera were initially diluted at 1:50 and a three-fold serial dilution performed for each bleed in duplicate. The endpoint dilution was taken as the highest dilution at which the OD reading was at twice background. The pre-bleed P2 control was present on all plates to account for any plate-to-plate variability in the background.

ELISAs employing GDF8 prohormone as the capture antigen were also performed to evaluate the ability of the TMV DJ5 peptide fusion vaccines to elicit antibodies capable of recognizing the DJ5 region in its native context. Table 32 summarizes the results. All the TMV DJ5 peptide fusion vaccines elicited antibodies that recognized GDF8, with a 1.5 to 2 $\log_{10}$ increase in endpoint dilution observed one week post the third vaccine (bleed 1), relative to the prebleed. The observed titers dropped for all the TMV vaccines by bleed 2, with the exception of TMV-FV6, where titers were maintained. The-FV6 vaccine also generated the highest endpoint dilution titer, mirroring the anti-TMV and anti-peptide ELISAs, and resulting in a response comparable to that observed in the P2-vaccinated animal. A large proportion of the FLAG tagged GDF8 prohormone protein employed to coat the ELISA plates possesses the propolypeptide region of GDF8, which is normally cleaved by a furin protease activity in vivo. Although the mature GDF8 is highly conserved pan species the propolypeptide region shows more amino acid heterogeneity. Therefore a large portion of the GDF8 P2 C-term (human sequence), employed as the positive control antigen in these studies, will likely be viewed as non-self by the immune system of the immunized goats. The extent to which this will influence the observed ELISA serum endpoint dilutions is unknown, but this fact needs to be considered in evaluating and comparing the responses between the different vaccine groups. Table 32, below, provides a summary of the endpoint dilution data for the anti-GDF8 ELISAs, testing sera from Goat Study #1.

TABLE 32

Endpoint Dilution Data From Goat Study #2
Anti-TMV and Anti-DJ5 ELISAs

| | | Target antigen | | |
| --- | --- | --- | --- | --- |
| Vaccine administered | Goat # | TMV U1 | BSA-DJ5(20) | BSA-DJ5(12) |
| P2-prebleed | | (–) | (–) | (–) |
| P2 | #10509 | 50 | 450 | (–) |
| TMV-FV1 | #10505 | 109,530 | 12,150 | 150 |
| TMV-FV5 | #10506 | 36,450 | 36,450 | 1,350 |
| TMV-FV6 | #10508 | 36,450 | 109,350 | 1,350 |
| TMV-FV7 | #10507 | 109,350 | 109,350 | 109,350 |

For Table 32, the well-coating conditions for the GDF8 were as described in Table 27, supra. Bleed 1 and Bleed 2 were taken 7 and 14 days after the third vaccination respectively. Sera were initially diluted at 1:50 and a three-fold serial dilution performed for each bleed in duplicate. The endpoint dilution was taken as the highest dilution at which the OD reading was at twice background.

For Goat Study #2, bleeds 7 days after the third vaccination were evaluated in ELISA format against the following targets:

Tobacco mosaic virus (type U1 only) coated directly.
The DJ5 (20) peptide conjugated to BSA (see FIG. 7).
The DJ5 (12) peptide conjugated to BSA (see FIG. 7).

The DJ5(8) peptide was omitted, based on the poor response to this region observed for Goat Study #1. For this study, no pre-bleed samples were available, therefore, the P2-prebleed from Goat Study #1 was employed as an negative control on each plate. The results are summarized in Table 33. For the full DJ5 peptide (DJ5(20)) conjugated to BSA, the highest endpoint dilutions were obtained with the soluble TMV-FV6 and TMV-FV7 vaccines, while the response to the insoluble TMV-FV1 vaccine was 1 $\log_{10}$ lower. Together with the first study this data suggests that the more soluble vaccine forms are capable of generating a more potent DJ5-specific response. For the first study there was a good correlation between the endpoint dilutions obtained when either TMV U1 or the DJ5 peptide was the ELISA target antigen. However, in the present study the TMV-FV1 vaccine generated one of the highest anti-TMV responses, comparable to the TMV-FV7 vaccine, while the end-point dilutions for the other two vaccines, TMV-FV6 and TMV-FV5, were only 3-fold lower. This indicates that the relation between vaccine form, i.e., soluble vs. precipitated, and the observed immune response may not be as clear-cut in the case of the TMV scaffold. As in the first study, the response to the DJ5(12)

BSA conjugate was 1 to 2 $\log_{10}$ lower than for the 20 amino acid DJ5 peptide, with the exception of-FV7 were the end-point dilution obtained was comparable. Table 33, below, provides a summary of the unblinded results for goat study #2, comparing the sera end point dilutions by anti-TMV U1 ELISAs and in ELISAs against BSA conjugates of the full length DJ5 peptide (20 amino acids; DJ5(20)) and the N-terminal 12 amino acids (DJ5(12)).

TABLE 33

Endpoint Dilution Data From Goat Study #2 Anti-TMV and Anti-DJ5 ELISAs

| | | Target antigen | | |
|---|---|---|---|---|
| Vaccine administered | Goat # | TMV U1 | BSA-DJ5(20) | BSA-DJ5(12) |
| P2-prebleed | | (–) | (–) | (–) |
| P2 | #10509 | 50 | 450 | (–) |
| TMV-FV1 | #10505 | 109,530 | 12,150 | 150 |
| TMV-FV5 | #10506 | 36,450 | 36,450 | 1,350 |
| TMV-FV6 | #10508 | 36,450 | 109,350 | 1,350 |
| TMV-FV7 | #10507 | 109,350 | 109,350 | 109,350 |

For Table 33, the well-coating conditions for the various targets were as described in Table 27, supra. Serum samples were taken 7 days after the third vaccination. The sera were initially diluted at 1/50 and a three-fold serial dilution performed for each bleed in duplicate. The endpoint dilution was taken as the highest dilution at which the OD reading was at twice background. (–), indicates that the OD reading was below twice background.

Employing the sera obtained from Goat Study #1 and Goat study #2, Western blots were performed as described in Harlow and Lane, *Antibodies. A Laboratory Manual*, Cold Spring Harbor Laboratory (1988). Reducing and non-reducing PAGE was performed in the same manner except that reducing sample buffer containing 5% beta-mercaptoethanol was used. A summary of the Westenr blot data is provided in Table 34.

The various goat antisera from Goat Study #1 and Goat Study #2 were also characterized by an in vitro transcription activation assay, as follows. The in vitro transcriptional activation assay used to quantitatively measure GDF8 bio-neutralization is essentially that of Thies et. al. (*Growth Factors* 18, 251 (2001)). Ninety-six well tissue culture treated luminometer ViewPlate™ assay plates (PerkinElmer Life and Analytical Sciences, Inc., Boston, Mass.) were seeded with $1.0\times10^5$ cells/well of A204 Rhabdomyosarcoma cells (ATCC HTB-82) and incubated in a 37° C., 5% CO2, humidified chamber. Complete A204 culture media consists of McCoy's 5A medium, 10% fetal bovine serum, 2% L-glutamine, and 1% Penn/Strep. Upon reaching greater than 80% confluence, the cells were transiently transfected with a mixture of plasmid pDPC4-luciferase and HCMV IE-lacZ using the protocol recommended by the manufacturer of the FUGENE transfection reagent (Roche Diagnostics Corporation, Indianapolis, Ind.) and incubated 16 hours in a 37° C., 5% CO2, humidified chamber. Plasmid pDPC4-luciferase contains four copies of the CAGA box, derived from the human plasminogen activator inhibitor (PAI-1), which confers GDF8 responsiveness to the heterologous promoter reporter construct.

Plasmid HCMV IE-lacZ contains a beta-galactosidase gene under the control of the constitutive human cytomegalovirus immediate early promoter. This gene is added as a control to normalize for transfection efficiencies. Cells were then treated with 100 ng/well GDF8 protein (R&D Systems Inc., Minneapolis, Minn.) and incubated an additional 16 hours in a 37° C., 5% CO2, humidified chamber. Luciferase and beta-galactosidase were quantified in the treated cells using the Dual-Light Luciferase Assay (Tropix, Applied Biosystems, Foster City, Calif.).

Each sample was run in duplicate (2 wells). The signal for each well was calculated as the luciferase signal divided by the beta-glactosidase signal times 100. The sample signal was calculated as the average of the two wells.

To test the bio-neutralization activity of a goat serum samples, the IgG from 200 μL of serum were incubated with the GDF8 protein (approximately 16 hours at 4° C.) prior to treatment of the cells. The percent inhibition was calculated as 100–(100× sample signal)/(signal with GDF8 alone–signal with no GDF8 added).

The results of the in vitro transcription activation assay are summarized by Table 34, below. The data for each vaccine designation is a cumulative for the results obtained for Goat Study #1 and Goat Study #2. The Mature GDF-8 data refers to the Western blots where the 12.5 kDa mature GDF-8 was employed as the target antigen.

TABLE 34

Western blot data and in vitro GDF8 neutralization data for sera from Goat Study #1 and Goat Study #2

| Vaccine designation | Antigen/Antibody | Mature GDF8, reduced | Mature GDF8, non-reduced | Neutralization Assay |
|---|---|---|---|---|
| ProGDF8P2 | GDF8 P2-Cterm | + | – | – |
| TMV-FV1 | DJ5(20)-TMV U1-GPAT | + | – | –/+ |
| TMV-FV5 | DJ5(20)-TMV U5-TPAT | +++ | ++ | + |
| TMV-FV6 | DJ5(12)-TMV U1-N term | +++ | – | + |
| TMV-FV7 | DJ5(12)-TMV U1-GPAT | +++ | – | + |
| Pro-CHO-GDF8flag | Goat #661 | +++ | +++ | +++ |
| Wyeth | A16 | +++ | +++ | +++ |
| R&D Systems | Rat mAb788 | +++ | +++ | +++ |

Consistent with ELISA data, all antigens elicited GDF8-specific immune responses in the treated goats when tested by standard Western blot methods. When tested for bio-neutralization, it was found that some sera from the immunized goats was neutralizing (TMV-FV5, -FV6 and-FV7) but that antigens TMV-FV1 and ProGDF8P2 did not elicit neutralizing antibody as detectable in the assay.

In one further examination of antibody specificity, it was determined that antigen TMV-FV5 (DJ5(20)-TMVU5-TPAT) was able to elicit antibody capable of recognizing non-denatured GDF8 in a non-denaturing Western blot format. For the purpose of comparison, all confirmed neutralizing antibody—one with reported biologic activity in-vivo (A16), also reacts with the non-denatured form of GDF8.

The non-denatured form of the GDF8 antigen in this assay is acknowledged by the scientific community as being more like "native" GDF8 and thus the inference is that antibody that reacts in this format is more likely to be biologically relevant.

This is the first demonstration of a recombinant GDF8 peptide capable of eliciting antibody that is reactive with the native form of GDF8 and neutralizing in the bio-assay.

Example 21

Serological Analysis of Bleeds from Swine Following Immunization with TMV-FV1, TMV-FV5, TMV-FV6, TMV-FV7 or the Pro GDF8 Protein For the study in swine (Swine Study #1), a total of 6 vaccines were tested, together with a wild-type TMV U1 control. Each vaccine or control was administered at a 250 µg dose in one of two adjuvants, to give a total of 14 combinations. The adjuvants considered were either Emunade (an oil in water emulsion) given at all immunizations, or complete Freund's adjuvant (CFA) administered with the first vaccine dose and incomplete Freund's adjuvant (IFA) for subsequent vaccinations. For this blinded study, there was one animal per vaccine/adjuvant combination and an unimmunized control for a total of 15 animals. The vaccines tested were:

GDF8 P2-Cterm (P2)
GDF8 prohormone
Wild-type TMV U1
TMV-FV1
TMV-FV5
TMV-FV6
TMV-FV7

Sera, obtained 7 days after the third vaccination, was evaluated in ELISA format against the same targets employed for the sera from Goat Study #2, namely tobacco mosaic virus (type U1 only), the DJ5 (20) peptide BSA conjugate and the DJ5 (12) peptide BSA conjugate (see FIG. 7). Microtiter plates were coated with the target antigen, at 5 µg/mL in carbonate/bicarbonate buffer (pH 9.6), overnight at 4° C. The ELISA protocol employed was that outlined for the indirect TMV ELISAs (Example 20), with the following modification: Rabbit anti-pig IgG (Sigma) was used as a secondary antibody in place of the rabbit anti-goat secondary. The results are summarized in tabular format in Table 35. As expected the anti-TMV response was specific to the TMV vaccinated animals, with end-point dilution titers at least 2 $\log_{10}$ higher than the control animal for the majority of the vaccine/adjuvant combinations. For the TMV-FV5/Freunds adjuvant combination, the animal had only received two doses due to health considerations and so the serum tested was four weeks post the second vaccination, which accounts for the low response observed. In general the anti-TMV immune response was greater for the vaccines administered with the more potent Freund's adjuvant, the exception being TMV-FV6, where the reverse was the case. For the DJ5(20)-BSA conjugate ELISAs, the GDF8 and P2 vaccinated animals sera had endpoint dilution titers at or below the unvaccinated and TMV U1 vaccinated controls. For the animals that received the TMV DJ5 peptide vaccines, the highest responses were 1 $\log_{10}$ higher than the controls and generally higher for the vaccines administered in conjunction with Freund's adjuvant. Only for vaccine-FV6 was the response with both adjuvants similar. As observed with the two goat studies, the serum endpoint dilutions on the DJ5(12)-BSA conjugate ELISA plates were lower for all animals that responded, relative to the DJ5(20) ELISA.

The ELISAs for the Goat Study #2 and Swine Study #1 were processed in parallel. Of note was the observation that the serum endpoint dilutions were substantially higher for the goat-derived sera; the ELISAs with the goat study were only permitted to develop for 5 minutes, compared to 20 minutes for the swine study ELISAs. This suggests that both the anti-carrier and peptide specific immune responses obtained in goats were greater than those observed in swine. The mature goat GDF8 protein sequence differs from that of other mammalian species, including swine, cattle and humans by one amino acid; the arginine that is C-terminal to the QANP (SEQ ID NO: 58) residues in the DJ5 region is substituted by a lysine. Therefore the human GDF8, employed in the current study together with the DJ5 peptide displayed on the surface of TMV were not true autoantigens in goats. Since the vaccine doses employed in both goat and swine were identical, this may be one possible explanation for the more robust response observed in goats. However, the fact that an immune response was observed in swine is encouraging. Table 35, below, provides a summary of the unblinded results for swine study #1, comparing the sera end point dilutions by anti-TMV U1 ELISAs and in ELISAs against BSA conjugates of the full length DJ5 peptide (20 amino acids; DJ5(20)) and the N-terminal 12 amino acids (DJ5(12)).

TABLE 35

Endpoint Dilution Data From Swine Study #1 Anti-TMV and Anti-DJ5 ELISAs

| Vaccine administered (adjuvant) | Swine # | Target antigen | | |
|---|---|---|---|---|
| | | TMV U1 | BSA-DJ5 (12) | BSA-DJ5 (20) |
| Control | #10491 | 150 | (–) | 50 |
| ProGDF8 (E) | #10485 | 150 | 50 | 50 |
| ProGDF8 (F) | #10487 | 150 | 50 | (–) |
| P2 (E) | #10495 | 50 | (–) | (–) |
| P2 (F) | #10501 | 50 | (–) | (–) |
| TMV-FV1 (E) | #10498 | 12,150 | 150 | 150 |
| TMV-FV1 (F) | #10484 | 3,6450 | 150 | 4,050 |
| TMV-FV5 (E) | #10483 | 4,050 | 450 | 1,350 |
| TMV-FV5 (F) | #10497 | 150 | (–) | 450 |
| TMV-FV6 (E) | #10490 | 36,450 | 50 | 1,350 |
| TMV-FV6 (F) | #10499 | 12,150 | 150 | 1,350 |
| TMV-FV7 (E) | #10496 | 12,150 | 450 | 150 |
| TMV-FV7 (F) | #10500 | 36,450 | 450 | 4,050 |
| TMV U1 (E) | #10488 | 36,450 | (–) | (–) |
| TMV U1 (F) | #10502 | 109,350 | 50 | 50 |

For Table 35, the well-coating conditions for the various targets were as described in Table 27, supra. Serum samples were taken 7 days after the third vaccination. The sera were initially diluted at 1:50 and a three-fold serial dilution performed for each bleed in duplicate. The endpoint dilution was taken as the highest dilution at which the OD reading was at twice background. (–), indicates that the OD reading was below twice background. (E), Emunade adjuvant; (F), Freund's adjuvant.

Example 22

Construction of GENEWARE® Vector for the Expression of the GDF8 Prohormone in Plants To generate pLSB2661, a FLAG tagged GDF8 (human myostatin prohormone gene)-containing fragment was amplified from plasmid 1202-37.39 by PCR. The actual sequences of the two oligonucleotides employed, together with their associated SEQ IDs, are shown in Table 36, below. The plasmid 1202-37.39 was generated by inserting the nucleototide sequence for a FLAG-tagged human proGDF8 into the plasmid pcDNA3.1/hygro (Invitrogen Corp., Carlsbad, Calif.).

TABLE 36

Forward And Reverse Oligonucleotides For PCR Amplification Of The ProgdF8 FLAG Insert From Plasmid 1202-37.39

| Forward oligonucleotide | | Reverse oligonucleotide | |
|---|---|---|---|
| Nucleic acid sequence GDF8-S1-Pac | SEQ ID NO | Nucleic acid sequence GDF8-A1-Sal | SEQ ID NO |
| CC TTAATTA ATG GAT CTA CAG AAG TTG CAG | 59 | CTT GTCGAC CTA CTT ATC GTC GTC ATC CTT G | 60 |

This PCR amplified fragment contains the entire ORF of the GDF8 prohormone that was followed by a FLAG epitope. This insert was digested with PacI and SalI, and was subsequently ligated to a 9.5 kb PacI/XhoI fragment of vector DN15, a derivative of BSG1037 (TMV vector expressing a green fluorescence protein; Fitzmaurice et al, U.S. Pat. No. 6,656,726 B1) that contains a "D" to "N" change at amino acid #1177 (D1177N) in the replicase protein and a "P" to "R" change at amino acid #30 (P30R) in the movement protein. This resulted in the generation of plasmid pLSB2661 and the FLAG-tagged GDF8 prohormone ORF region in pLSB2661 was sequenced confirmed (SEQ ID NO: 61). Table 37, below gives the final amino acid sequences of the FLAG tagged GDF8 prohormone (proGDF8 FLAG) expressed from pLSB2661, based on the obtained sequence

TABLE 37

Full Amino Acid Sequence Of Pro FDG-8 FLAG Together With Its Associated SEQ ID NOs.

| Shorthand descriptor | SEQ ID | Coat protein amino acid sequence |
|---|---|---|
| pro GDF8 FLAG | 62 | MDLQKLQLCVYIYLFMLIVAGPVDLNENSEQKENVE KEGLCNACTWRQNTKSSRIEAIKIQILSKLRLETAP NISKDVIRQLLPKAPPLRELIDQYDVQRDDSSDGSL EDDDYHATTETIITMPTESDFLMQVDGKPKCCFFK FSSKIQYNKVVKAQLWIYLRPVETPTTVFVQILRLI KPMKDGTRYTGIRSLKLDMNPGTGIWQSIDVKTVLQ NWLKQPESNLGIEIKALDENGHDLAVTFPGPGEDGL NPFLEVKVTDTPKRSRRDFGLDCDEHSTESRCCRYP LTVDFEAFGWDWIIAPKRYKANYCSGECEFVFLQKY PHTHLVHQANPRGSAGPCCTPTKMSPINMLYFNGKE QIIYGKIPAMVVDRCGCSLEDYKDDDDK |

Example 23

Production and Characterization of the GDF8 Prohormone Expressed in Plants

The FLAG tagged GDF8 prohormone was produced by transcription of plasmid PLSB 2661. Transcript synthesis, verification of integrity and inoculation onto plants was performed as described in Example 9. As noted in Example 9, alternative host plants, other than N. benthamiana can be employed in the production of the FLAG tagged GDF8 prohormone. For example, N. excelsiana or N. tabacum represent two possible alternative plant hosts. To evaluate the level of expression of the GDF8 prohormone as a function of the days post inoculation (DPI), leaf punches of systemically infected tissue were taken at 5 DPI through 8 DPI. The leaf punch samples were stored at −20° C. until processing. In addition to the leaf punch samples taken for plants inoculated with pLSB2661, uninoculated plants and plants inoculated with a GENEWARE® vector expressing GFP were sampled as controls.

The leaf punch samples were homogenized in PAGE loading dye and analyzed in PAGE gel and Western blot analysis. The Western blots were probed with either the anti-GDF8 Goat #661 polyclonal or an anti-FLAG monoclonal (Sigma). From the PAGE gels, unique bands corresponding to the GENEWARE® derived U5 coat protein (~20 kDa) and the expressed GFP (~30 kDa) were detectable at 6 and 8 DPI (the two time points analyzed) for the GFP control. Both these bands were absent in the case of the uninfected control. For the pLSB2661 infected plants, a U5 coat protein band was only detectable at 8 DPI, although the plants were symptomatic at 5 DPI. No other unique bands were evident by PAGE gel over the time course. For the Western blot employing the Goat #661 antibody, a unique band migrating at ~50 kDa was present at 7 and 8 DPI, for the pLSB2661 inoculated plants. This band most likely corresponds to the unprocessed GDF8 prohormone, which has a molecular weight of 50 kDa. The Goat #661 antibody also cross-reacted with high molecular weight species that were detected over the same DPI range. The nonspecific cross-reactivity in the uninfected and GFP control lanes was minimal. When a parallel Western blot was probed with the anti-FLAG monoclonal, the cross-reactivity with plant host proteins was greater. However, for the lanes containing extracts from pLSB 2661 infected tissue, the same high MW species observed with the Goat #661 antibody were detected, at all DPI screened, with no cross-reacting bands of similar molecular weight present in either control. A 50 kDa species was also detected at 7 and 8 DPI, although a weak cross-reacting band co-migrated in all samples. Taken together this data indicates that GDF8 prohormone expression was obtained using GENEWARE®-based expression in plants and that the unprocessed prohormone accumulated as the principal species. In addition, a high molecular weight anti-FLAG and anti-GDF8 reactive species was present, which may represent a cross-linked form of the GDF8 prohormone. However, the level of proGDF8 FLAG accumulation obtained with the pLSB2661 vector was insufficient to allow for the economic purification and recovery of the protein at scale. It should be noted that further iterations of vector optimization would be possible, in order to improve proGDF8 accumulation in plants. For example, the native proGDF8 signal sequence could be replaced by a plant derived signal sequence e.g. the extensin or alpha amylase signal sequences, the protein could be retained in the endoplasmic reticulum (ER) by the addition of an ER retention signal at the C-terminus of the protein, e.g. the KDEL sequence and the codon usage of the proGDF8 ORF could be optimized so that the N. tabacum or TMV preferred codon usage is employed. Furthermore these different strategies can be combined to further improve accumulation.

TABLE 38

Additional sequences

| SEQ ID NOs | Nucleic acid sequence |
|---|---|
| 59 | Oligonucleotide primer GDF8-S1-Pac CC TTAATTA ATG GAT CTA CAG AAG TTG CAG |
| 60 | Oligonucleotide primer GDF8-A1-Sal CTT GTCGAC CTA CTT ATC GTC GTC ATC CTT G |

TABLE 38-continued

Additional sequences

| SEQ ID NOs | Nucleic acid sequence |
|---|---|
| 61 | Nucleotide sequence spanning the proGDF8FLAG ORF in vector pLSB2661<br>TTAATTAATGGATCTACAGAAGTTGCAGTTGTGTGTCTACATCTA<br>TTTGTTCATGTTGATCGTCGCCGGACCTGTTGACTTGAACGAAAA<br>TTCTGAACAGAAGGAGAACGTTGAGAAGGAAGGTTTGTGCAACGC<br>TTGTACATGGCGTCAAAATACAAAGTCCTCTCGTATTGAAGCTAT<br>CAAGATTCAAATTTTGTCTAAGTTGAGATTGGAAACTGCCCCAAA<br>TATTTCTAAGGACGTCATTCGTCAATTGTTGCCAAAGGCCCCACC<br>TTTGAGAGAATTGATCGACCAATACGATGTTCAAAGAGACGATTC<br>TTCTGACGGTTCCCTTGAAGACGATGACTACCATGCCACTACTGA<br>AACTATTATCACTATGCCAACTGAATCCGACTTTTTGATGCAGGT<br>TTGATGGTAAGCCAAAGTGCTGTTTTTTCAAGTTCTCTTCCAAGA<br>TTCAATACAACAAGGTTGTTAAAGCTCAATTGTGGATTTACCTTC<br>GTCCAGTTGAAACACCAACTACTGTGTTTGTTCAGATTTTGCGTT<br>TGATTAAGCCAATGAAGGATGGAACTAGATACACAGGTATTAGAT<br>CCTTGAAGTTGGATATGAATCCTGGTACAGGAATCTGGCAATCTA<br>TCGACGTTAAAACTGTTCTTCAAAACTGGTTGAAGCAACCAGAGT<br>CTAATTTGGGTATCGAGATTAAGGCCTTGACGAAAACGGACATG<br>ACTTGGCCGTTACTTTTCCTGGTCCTGGTGAAGACGGTTTGAACC<br>CATTTCTGGAAGTTAAGGTTACTGATACTCCTAAGCGTTCCAGGA<br>GAGACTTCGGATTGGATTGTGATGAACATTCTACTGAGTCTAGAT<br>GTTGTAGATATCCATTGACCGTTGATTTCGAGGCCTTCGGTTGGG<br>ATTGGATCATTGCCCCAAAGAGATACAAAGCTAACTATTGTTCCG<br>GTGAATGTGAGTTCGTTTTCTTGCAGAAGTACCCACATACCCATT<br>TGGTTCATCAGGCTAATCCAAGAGGATCTGCTGGTCCATGTTGTA<br>CCCCAACTAAAATGTCCCCTATCAACATGTTGTACTTCAACGGTA<br>AGGAGCAGATTATTTACGGTAAGATCCCTGCTATGGTTGTTGATA<br>GATGTGGTTGTTCTCTCGAGGATTACAAGGATGACGACGATAAGT<br>AGG:TCGAGGGGTAGTCAAGATGCATA |
| | pro FDG-8 FLAG |
| 62 | MDLQKLQLCVYIYLFMLIVAGPVDLNENSEQKENVEKEGLCNACTWR<br>QNTKSSRIEAIKIQILSKLRLETAPNISKDVIRQLLPKAPPLRELID<br>QYDVQRDDSSDGSLEDDDYHATTETIITMPTESDFLMQVDGKPKCCF<br>FKFSSKIQYNKVVKAQLWIYLRPVETPTTVFVQILRLIKPMKDGTRY<br>TGIRSLKLDMNPGTGIWQSIDVKTVLQNWLKQPESNLGIEIKALDEN<br>GHDLAVTFPGPGEDGLNPFLEVKVTDTPKRSRRDFGLDCDEHSTESR<br>CCRYPLTVDFEAFGWDWIIAPKRYKANYCSGECEFVFLQKYPHTHLV<br>HQANPRGSAGPCCTPTKMSPINMLYFNGKEQIIYGKIPAMVVDRCGC<br>SLEDYKDDDDK |

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled. Numerous references are cited in the specification, including Genebank accession numbers of published and/or internet-published nucleic acid and polypeptide/protein sequences, the disclosures of which are incorporated by reference in their entireties.

SEQUENCE LISTING

```
<160> NUMBER OF SEQ ID NOS: 36

<210> SEQ ID NO 1
<211> LENGTH: 375
<212> TYPE: PRT
<213> ORGANISM: Human
<220> FEATURE:
<221> NAME/KEY: Peptide
<222> LOCATION: (267)..(286)
<223> OTHER INFORMATION: DJ1
<220> FEATURE:
<221> NAME/KEY: Peptide
<222> LOCATION: (282)..(301)
<223> OTHER INFORMATION: DJ2
<220> FEATURE:
<221> NAME/KEY: Peptide
<222> LOCATION: (297)..(316)
<223> OTHER INFORMATION: DJ3
<220> FEATURE:
<221> NAME/KEY: Peptide
<222> LOCATION: (312)..(331)
<223> OTHER INFORMATION: DJ4
<220> FEATURE:
<221> NAME/KEY: Peptide
<222> LOCATION: (327)..(346)
<223> OTHER INFORMATION: DJ5
<220> FEATURE:
<221> NAME/KEY: Peptide
<222> LOCATION: (342)..(361)
<223> OTHER INFORMATION: DJ6
<220> FEATURE:
<221> NAME/KEY: Peptide
<222> LOCATION: (357)..(375)
<223> OTHER INFORMATION: DJ7

<400> SEQUENCE: 1
```

-continued

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 2
<211> LENGTH: 2823
<212> TYPE: DNA
<213> ORGANISM: Human
<220> FEATURE:
```

```
<221> NAME/KEY: misc_feature
<222> LOCATION: (134)..(1261)
<223> OTHER INFORMATION: Encodes Precursor GDF8
<220> FEATURE:
<221> NAME/KEY: Peptide
<222> LOCATION: (1112)..(1171)
<223> OTHER INFORMATION: Encodes DJ5

<400> SEQUENCE: 2
```

| | | | | | |
|---|---|---|---|---|---|
| agattcactg | gtgtggcaag | ttgtctctca | gactgtacat | gcattaaaat | tttgcttggc | 60 |
| attactcaaa | agcaaagaa | aagtaaaagg | aagaaacaag | aacaagaaaa | aagattatat | 120 |
| tgattttaaa | atcatgcaaa | aactgcaact | ctgtgtttat | atttacctgt | ttatgctgat | 180 |
| tgttgctggt | ccagtggatc | taaatgagaa | cagtgagcaa | aaagaaaatg | tggaaaaaga | 240 |
| ggggctgtgt | aatgcatgta | cttggagaca | aaacactaaa | tcttcaagaa | tagaagccat | 300 |
| taagatacaa | atcctcagta | aacttcgtct | ggaaacagct | cctaacatca | gcaaagatgt | 360 |
| tataagacaa | cttttacccca | aagctcctcc | actccgggaa | ctgattgatc | agtatgatgt | 420 |
| ccagagggat | gacagcagcg | atggctcttt | ggaagatgac | gattatcacg | ctacaacgga | 480 |
| aacaatcatt | accatgccta | cagagtctga | ttttctaatg | caagtggatg | gaaaacccaa | 540 |
| atgttgcttc | tttaaattta | gctctaaaat | acaatacaat | aaagtagtaa | aggcccaact | 600 |
| atggatatat | ttgagacccg | tcgagactcc | tacaacagtg | tttgtgcaaa | tcctgagact | 660 |
| catcaaacct | atgaaagacg | gtacaaggta | tactggaatc | cgatctctga | aacttgacat | 720 |
| gaacccaggc | actggtatt | ggcagagcat | tgatgtgaag | acagtgttgc | aaaattggct | 780 |
| caaacaacct | gaatccaact | taggcattga | aataaaagct | ttagatgaga | atggtcatga | 840 |
| tcttgctgta | accttcccag | gaccaggaga | agatgggctg | aatccgtttt | tagaggtcaa | 900 |
| ggtaacagac | acaccaaaaa | gatccagaag | ggattttggt | cttgactgtg | atgagcactc | 960 |
| aacagaatca | cgatgctgtc | gttaccctct | aactgtggat | tttgaagctt | ttggatggga | 1020 |
| ttggattatc | gctcctaaaa | gatataaggc | caattactgc | tctggagagt | gtgaatttgt | 1080 |
| attttacaa | aaatatcctc | atactcatct | ggtacaccaa | gcaaaccca | gaggttcagc | 1140 |
| aggcccttgc | tgtactccca | caaagatgtc | tccaattaat | atgctatatt | ttaatggcaa | 1200 |
| agaacaaata | atatatggga | aaattccagc | gatggtagta | gaccgctgtg | ggtgctcatg | 1260 |
| agatttatat | taagcgttca | taacttccta | aaacatggaa | ggttttcccc | tcaacaattt | 1320 |
| tgaagctgtg | aaattaagta | ccacaggcta | taggcctaga | gtatgctaca | gtcacttaag | 1380 |
| cataagctac | agtatgtaaa | ctaaaagggg | gaatatatgc | aatggttggc | atttaaccat | 1440 |
| ccaaacaaat | catacaagaa | agttttatga | tttccagagt | ttttgagcta | gaaggagatc | 1500 |
| aaattacatt | tatgttccta | tatattacaa | catcggcgag | gaaatgaaag | cgattctcct | 1560 |
| tgagttctga | tgaattaaag | gagtatgctt | taaagtctat | ttctttaaag | ttttgtttaa | 1620 |
| tatttacaga | aaaatccaca | tacagtattg | gtaaaatgca | ggattgttat | ataccatcat | 1680 |
| tcgaatcatc | cttaaacact | tgaatttata | ttgtatggta | gtatacttgg | taagataaaa | 1740 |
| ttccacaaaa | ataggatgg | tgcagcatat | gcaatttcca | ttcctattat | aattgacaca | 1800 |
| gtacattaac | aatccatgcc | aacggtgcta | atacgatagg | ctgaatgtct | gaggctacca | 1860 |
| ggtttatcac | ataaaaaaca | ttcagtaaaa | tagtaagttt | ctcttttctt | caggggcatt | 1920 |
| ttcctacacc | tccaaatgag | gaatggattt | tctttaatgt | aagaagaatc | atttttctag | 1980 |
| aggttggctt | tcaattctgt | agcatacttg | gagaaactgc | attatcttaa | aaggcagtca | 2040 |
| aatggtgttt | gttttatca | aaatgtcaaa | ataacatact | tggagaagta | tgtaattttg | 2100 |

```
tctttggaaa attacaacac tgcctttgca acactgcagt ttttatggta aaataataga    2160
aatgatcgac tctatcaata ttgtataaaa agactgaaac aatgcattta tataatatgt    2220
atacaatatt gttttgtaaa taagtgtctc ctttttttatt tactttggta tattttttaca   2280 ctaaggacat ttcaaattaa gtactaaggc acaaagacat gtcatgcatc acagaaaagc    2340
aactacttat atttcagagc aaattagcag attaaatagt ggtcttaaaa ctccatatgt    2400
taatgattag atggttatat tacaatcatt ttatattttt ttacatgatt aacattcact     2460 tatgattca tgatggctgt ataaagtgaa tttgaaatttt caatggttta ctgtcattgt      2520
gtttaaatct caacgttcca ttatttttaat acttgcaaaa acattactaa gtataccaaa    2580
ataattgact ctattatctg aaatgaagaa taaactgatg ctatctcaac aataactgtt    2640
acttttattt tataatttga taatgaatat atttctgcat ttatttactt ctgttttgta    2700
aattgggatt ttgttaatca aatttattgt actatgacta aatgaaatta tttcttacat    2760
ctaatttgta gaaacagtat aagttatatt aaagtgtttt cacattttttt tgaaagacaa    2820 aaa                                                                   2823

<210> SEQ ID NO 3
<211> LENGTH: 1164
<212> TYPE: DNA
<213> ORGANISM: Artificial Sequence
<220> FEATURE:
<223> OTHER INFORMATION: GDF8 prohormone FLAG tag fusion protein
<220> FEATURE:
<221> NAME/KEY: sig_peptide
<222> LOCATION: (10)..(75)
<223> OTHER INFORMATION:
<220> FEATURE:
<221> NAME/KEY: misc_feature
<222> LOCATION: (76)..(1131)
<223> OTHER INFORMATION: Encodes Precursor GDF8
<220> FEATURE:
<221> NAME/KEY: misc_feature
<222> LOCATION: (1132)..(1161)
<223> OTHER INFORMATION: Encodes C-terminal FLAG tag
<220> FEATURE:
<221> NAME/KEY: Peptide
<222> LOCATION: (985)..(1044)
<223> OTHER INFORMATION: Encodes DJ5 Peptide

<400> SEQUENCE: 3
atggatctac agaagttgca gttgtgtgtc tacatctatt tgttcatgtt gatcgtcgcc      60
ggacctgttg acttgaacga aaattctgaa cagaaggaga acgttgagaa ggaaggtttg    120
tgcaacgctt gtacatggcg tcaaaataca aagtcctctc gtattgaagc tatcaagatt    180
caaattttgt ctaagttgag attggaaact gccccaaata tttctaagga cgtcattcgt    240
caattgttgc caaaggcccc acctttgaga gaattgatcg accaatacga tgttcaaaga    300
gacgattctt ctgacggttc ccttgaagac gatgactacc atgccactac tgaaactatt    360
atcactatgc caactgaatc cgacttttg atgcaggttg atggtaagcc aaagtgctgt    420
tttttcaagt tctcttccaa gattcaatac aacaaggttg ttaaagctca attgtggatt    480
taccttcgtc cagttgaaac accaactact gtgtttgttc agattttgcg tttgattaag    540
ccaatgaagg atggaactag atacacaggt attgatcct tgaagttgga tatgaatcct    600
ggtacaggaa tctggcaatc tatcgacgtt aaaactgttc ttcaaaactg gttgaagcaa    660
ccagagtcta atttgggtat cgagattaag gccttggacg aaaacggaca tgacttggcc    720
gttacttttc ctggtcctgg tgaagacggt ttgaacccat ttctggaagt taaggttact    780
```

```
gatactccta agcgttccag gagagacttc ggattggatt gtgatgaaca ttctactgag    840
tctagatgtt gtagatatcc attgaccgtt gatttcgagg ccttcggttg ggattggatc    900
attgccccaa agagatacaa agctaactat tgttccggtg aatgtgagtt cgttttcttg    960
cagaagtacc cacatacccc tttggttcat caggctaatc caagaggatc tgctggtcca   1020
tgttgtaccc caactaaaat gtcccctatc aacatgttgt acttcaacgg taaggagcag   1080
attatttacg gtaagatccc tgctatggtt gttgatagat gtggttgttc tctcgaggat   1140
tacaaggatg acgacgataa gtag                                          1164
```

<210> SEQ ID NO 4
<211> LENGTH: 20
<212> TYPE: PRT
<213> ORGANISM: Human
<220> FEATURE:
<221> NAME/KEY: misc_feature
<223> OTHER INFORMATION: DJ1

<400> SEQUENCE: 4

Asp Phe Gly Leu Asp Cys Asp Glu His Ser Thr Glu Ser Arg Cys Cys
1               5                   10                  15

Arg Tyr Pro Leu
            20

<210> SEQ ID NO 5
<211> LENGTH: 20
<212> TYPE: PRT
<213> ORGANISM: Human
<220> FEATURE:
<221> NAME/KEY: misc_feature
<223> OTHER INFORMATION: DJ2

<400> SEQUENCE: 5

Cys Arg Tyr Pro Leu Thr Val Asp Phe Glu Ala Phe Gly Trp Asp Trp
1               5                   10                  15

Ile Ile Ala Pro
            20

<210> SEQ ID NO 6
<211> LENGTH: 20
<212> TYPE: PRT
<213> ORGANISM: Human
<220> FEATURE:
<221> NAME/KEY: misc_feature
<223> OTHER INFORMATION: DJ3

<400> SEQUENCE: 6

Trp Ile Ile Ala Pro Lys Arg Tyr Lys Ala Asn Tyr Cys Ser Gly Glu
1               5                   10                  15

Cys Glu Phe Val
            20

<210> SEQ ID NO 7
<211> LENGTH: 20
<212> TYPE: PRT
<213> ORGANISM: Human
<220> FEATURE:
<221> NAME/KEY: misc_feature
<223> OTHER INFORMATION: DJ4

<400> SEQUENCE: 7

Glu Cys Glu Phe Val Phe Leu Gln Lys Tyr Pro His Thr His Leu Val
1               5                   10                  15

-continued

```
His Gln Ala Asn
            20

<210> SEQ ID NO 8
<211> LENGTH: 20
<212> TYPE: PRT
<213> ORGANISM: Human
<220> FEATURE:
<221> NAME/KEY: misc_feature
<223> OTHER INFORMATION: DJ5

<400> SEQUENCE: 8

Val His Gln Ala Asn Pro Arg Gly Ser Ala Gly Pro Cys Cys Thr Pro
1               5                   10                  15

Thr Lys Met Ser
            20

<210> SEQ ID NO 9
<211> LENGTH: 20
<212> TYPE: PRT
<213> ORGANISM: Human
<220> FEATURE:
<221> NAME/KEY: misc_feature
<223> OTHER INFORMATION: DJ6

<400> SEQUENCE: 9

Pro Thr Lys Met Ser Pro Ile Asn Met Leu Tyr Phe Asn Gly Lys Glu
1               5                   10                  15

Gln Ile Ile Tyr
            20

<210> SEQ ID NO 10
<211> LENGTH: 20
<212> TYPE: PRT
<213> ORGANISM: Human
<220> FEATURE:
<221> NAME/KEY: misc_feature
<223> OTHER INFORMATION: DJ7

<400> SEQUENCE: 10

Val His Gln Ala Asn Pro Arg Gly Ser Ala Gly Pro Cys Cys Thr Pro
1               5                   10                  15

Thr Lys Met Ser
            20

<210> SEQ ID NO 11
<211> LENGTH: 20
<212> TYPE: PRT
<213> ORGANISM: Anas platyrhynchos

<400> SEQUENCE: 11

Val His Gln Ala Asn Pro Arg Gly Ser Ala Gly Pro Cys Cys Thr Pro
1               5                   10                  15

Thr Lys Met Ser
            20

<210> SEQ ID NO 12
<211> LENGTH: 20
<212> TYPE: PRT
<213> ORGANISM: Anser anser

<400> SEQUENCE: 12

Val His Gln Ala Asn Pro Arg Gly Ser Ala Gly Pro Cys Cys Thr Pro
1               5                   10                  15
```

Thr Lys Met Ser
            20

<210> SEQ ID NO 13
<211> LENGTH: 20
<212> TYPE: PRT
<213> ORGANISM: Anser anser

<400> SEQUENCE: 13

Val Leu Gln Ala Asn Pro Arg Gly Ser Ala Gly Pro Cys Cys Thr Pro
1               5                   10                  15

Thr Lys Met Ser
            20

<210> SEQ ID NO 14
<211> LENGTH: 20
<212> TYPE: PRT
<213> ORGANISM: Bos taurus

<400> SEQUENCE: 14

Val His Gln Ala Asn Pro Arg Gly Ser Ala Gly Pro Cys Cys Thr Pro
1               5                   10                  15

Thr Lys Met Ser
            20

<210> SEQ ID NO 15
<211> LENGTH: 20
<212> TYPE: PRT
<213> ORGANISM: Canis familiaris

<400> SEQUENCE: 15

Val His Gln Ala Asn Pro Arg Gly Ser Ala Gly Pro Cys Cys Thr Pro
1               5                   10                  15

Thr Lys Met Ser
            20

<210> SEQ ID NO 16
<211> LENGTH: 20
<212> TYPE: PRT
<213> ORGANISM: Capra hircus

<400> SEQUENCE: 16

Val His Gln Ala Asn Pro Lys Gly Ser Ala Gly Pro Cys Cys Thr Pro
1               5                   10                  15

Thr Lys Met Ser
            20

<210> SEQ ID NO 17
<211> LENGTH: 20
<212> TYPE: PRT
<213> ORGANISM: Columba livia

<400> SEQUENCE: 17

Val His Gln Ala Asn Pro Arg Gly Ser Ala Gly Pro Cys Cys Thr Pro
1               5                   10                  15

Thr Lys Met Ser
            20

<210> SEQ ID NO 18
<211> LENGTH: 20
<212> TYPE: PRT
<213> ORGANISM: Coturnix chinensis

```
<400> SEQUENCE: 18

Val His Gln Ala Asn Pro Arg Gly Ser Ala Gly Pro Cys Cys Thr Pro
1               5                  10                  15

Thr Lys Met Ser
            20

<210> SEQ ID NO 19
<211> LENGTH: 20
<212> TYPE: PRT
<213> ORGANISM: Danio rerio

<400> SEQUENCE: 19

Val Asn Lys Ala Ser Pro Arg Gly Thr Ala Gly Pro Cys Cys Thr Pro
1               5                  10                  15

Thr Lys Met Ser
            20

<210> SEQ ID NO 20
<211> LENGTH: 20
<212> TYPE: PRT
<213> ORGANISM: Equus caballus

<400> SEQUENCE: 20

Val His Gln Ala Asn Pro Arg Gly Ser Ala Gly Pro Cys Cys Thr Pro
1               5                  10                  15

Thr Lys Met Ser
            20

<210> SEQ ID NO 21
<211> LENGTH: 20
<212> TYPE: PRT
<213> ORGANISM: Gallus gallus

<400> SEQUENCE: 21

Val His Gln Ala Asn Pro Arg Gly Pro Ala Gly Pro Cys Cys Thr Pro
1               5                  10                  15

Thr Lys Met Ser
            20

<210> SEQ ID NO 22
<211> LENGTH: 20
<212> TYPE: PRT
<213> ORGANISM: Gallus gallus

<400> SEQUENCE: 22

Val His Gln Ala Asn Pro Arg Gly Ser Ala Gly Pro Cys Cys Thr Pro
1               5                  10                  15

Thr Lys Met Ser
            20

<210> SEQ ID NO 23
<211> LENGTH: 20
<212> TYPE: PRT
<213> ORGANISM: I. punctatus

<400> SEQUENCE: 23

Val Asn Lys Ala Ser Pro Arg Gly Thr Ala Gly Pro Cys Cys Thr Pro
1               5                  10                  15

Thr Lys Met Ser
            20
```

```
<210> SEQ ID NO 24
<211> LENGTH: 20
<212> TYPE: PRT
<213> ORGANISM: Lepus capensis

<400> SEQUENCE: 24

Val His Gln Ala Asn Pro Arg Gly Ser Ala Gly Pro Cys Cys Thr Pro
1               5                   10                  15

Thr Lys Met Ser
            20

<210> SEQ ID NO 25
<211> LENGTH: 20
<212> TYPE: PRT
<213> ORGANISM: Macaca fascicularis

<400> SEQUENCE: 25

Val His Gln Ala Asn Pro Arg Gly Ser Ala Gly Pro Cys Cys Thr Pro
1               5                   10                  15

Thr Lys Met Ser
            20

<210> SEQ ID NO 26
<211> LENGTH: 20
<212> TYPE: PRT
<213> ORGANISM: Meleagris gallopavo

<400> SEQUENCE: 26

Val His Gln Ala Asn Pro Arg Gly Ser Ala Gly Pro Cys Cys Thr Pro
1               5                   10                  15

Thr Lys Met Ser
            20

<210> SEQ ID NO 27
<211> LENGTH: 20
<212> TYPE: PRT
<213> ORGANISM: Morone chrysops

<400> SEQUENCE: 27

Val Asn Lys Ala Asn Pro Arg Gly Thr Ala Gly Pro Cys Cys Thr Pro
1               5                   10                  15

Thr Lys Met Ser
            20

<210> SEQ ID NO 28
<211> LENGTH: 20
<212> TYPE: PRT
<213> ORGANISM: Mus musculus

<400> SEQUENCE: 28

Val His Gln Ala Asn Pro Arg Gly Ser Ala Gly Pro Cys Cys Thr Pro
1               5                   10                  15

Thr Lys Met Ser
            20

<210> SEQ ID NO 29
<211> LENGTH: 20
<212> TYPE: PRT
<213> ORGANISM: O. mykiss

<400> SEQUENCE: 29

Val Asn Lys Ala Asn Pro Arg Gly Thr Ala Gly Pro Cys Cys Thr Pro
1               5                   10                  15
```

Thr Lys Met Ser
            20

<210> SEQ ID NO 30
<211> LENGTH: 20
<212> TYPE: PRT
<213> ORGANISM: Ovis aries

<400> SEQUENCE: 30

Val His Gln Ala Asn Pro Lys Gly Ser Ala Gly Pro Cys Cys Thr Pro
1               5                   10                  15

Thr Lys Met Ser
            20

<210> SEQ ID NO 31
<211> LENGTH: 20
<212> TYPE: PRT
<213> ORGANISM: Papio hamadryas

<400> SEQUENCE: 31

Val His Gln Ala Asn Pro Arg Gly Ser Ala Gly Pro Cys Cys Thr Pro
1               5                   10                  15

Thr Lys Met Ser
            20

<210> SEQ ID NO 32
<211> LENGTH: 20
<212> TYPE: PRT
<213> ORGANISM: Rattus norvegicus

<400> SEQUENCE: 32

Val His Gln Ala Asn Pro Arg Gly Ser Ala Gly Pro Cys Cys Thr Pro
1               5                   10                  15

Thr Lys Met Ser
            20

<210> SEQ ID NO 33
<211> LENGTH: 20
<212> TYPE: PRT
<213> ORGANISM: Salmo salar

<400> SEQUENCE: 33

Val Asn Lys Ala Asn Pro Arg Gly Thr Ala Gly Pro Cys Cys Thr Pro
1               5                   10                  15

Thr Lys Met Ser
            20

<210> SEQ ID NO 34
<211> LENGTH: 20
<212> TYPE: PRT
<213> ORGANISM: Sparus aurata

<400> SEQUENCE: 34

Val Asn Lys Ala Asn Pro Arg Gly Thr Ala Gly Pro Cys Cys Thr Pro
1               5                   10                  15

Thr Lys Met Ser
            20

<210> SEQ ID NO 35
<211> LENGTH: 20
<212> TYPE: PRT
<213> ORGANISM: Sus scrofa

-continued

```
<400> SEQUENCE: 35

Val His Gln Ala Asn Pro Arg Gly Ser Ala Gly Pro Cys Cys Thr Pro
1               5                   10                  15

Thr Lys Met Ser
            20

<210> SEQ ID NO 36
<211> LENGTH: 20
<212> TYPE: PRT
<213> ORGANISM: Sus scrofa

<400> SEQUENCE: 36

Val Leu Gln Ala Asn Pro Arg Gly Ser Ala Gly Pro Cys Cys Thr Pro
1               5                   10                  15

Thr Lys Met Ser
            20
```

What is claimed is:

1. A fusion protein comprising:
   (a) a GDF8 peptide domain of 50 amino acids or fewer, or an antigenic fragment of the GDF8 peptide domain; and
   (b) a plant virus coat protein from a single-stranded plus-sense RNA virus, or at least one fragment of the plant virus coat protein;
   wherein the GDF8 peptide domain comprises amino acid residues 327 to 346 of SEQ ID NO:1, or the antigenic fragment of the GDF8 peptide domain comprises amino acid residues 327 to 338 of SEQ ID NO: 1; and
   wherein the fragment of the virus coat protein is missing from 1 to about 10 amino acid residues relatives to the native virus coat protein, or has been divided into two or more domains by the insertion of the GDF8 peptide domain, or is missing from 1 to about 10 amino acid residues relative to the native virus coat protein and has been divided into two or more domains by the insertion of the GDF8 peptide domain.

2. The fusion protein of claim 1, wherein the plant virus coat protein is a tobamovirus coat protein.

3. The fusion protein of claim 2, wherein the GDF8 peptide domain or the antigenic fragment of the GDF8 peptide domain is fused to a fragment of the coat protein; and wherein the tobamovirus virus is a tobacco mosaic virus strain U1 or U5.

4. The fusion protein of claim 1 comprising an amino acid sequence selected from the group consisting of SEQ ID NO: 47, SEQ ID NO: 48, SEQ ID NO: 49, SEQ ID NO: 50, SEQ ID NO: 51, SEQ ID NO: 54, and SEQ ID NO: 55.

5. The fusion protein of claim 1,
   wherein the GDF8 peptide domain is fused to the viral coat protein at a position selected from the group consisting of:
   (i) the N-terminus of the viral coat protein,
   (ii) the C-terminus of the viral coat protein,
   (iii) four amino acids from the C-terminus of the viral coat protein, and
   (iv) within an externally exposed loop region of the viral coat protein; wherein the fusion protein elicits an immune response to GDF8, with or without an adjuvant.

6. The fusion protein of claim 1, wherein the GDF8 peptide domain comprises one or more amino acid substitutions, wherein there are no more than five amino acid substitutions between amino acid residues 327 to residue 346 of SEQ ID NO: 1; and
   wherein the fusion protein specifically binds to rat monoclonal antibody 788.

7. The fusion protein of claim 1 wherein the GDF8 peptide domain or the antigenic fragment of the GDF8 peptide domain comprises amino acid substitutions at a position selected from the group consisting of residues 328, 329, 331, 333, 335 of SEQ ID NO: 1, and any combination(s) thereof.

8. The fusion protein of claim 7 wherein,
   (a) amino acid residue 328 is His, Leu, or Asn;
   (b) amino acid residue 329 is Gln or Lys;
   (c) amino acid residue 331 is Asn or Ser;
   (d) amino acid residue 333 is Arg or Lys; and
   (e) amino acid residue 335 is Ser, Pro, or Thr.

9. The fusion protein of claim 8 comprising no more than one amino acid substitution between residues 327 to residue 346, provided that the fusion protein specifically binds to rat monoclonal antibody 788.

10. The fusion protein of claim 1 that comprises a specific neutralization epitope for an anti-GDF8 antibody.

11. The fusion protein of claim 10 wherein the anti-GDF8 antibody is selected from the group consisting of rat anti-GDF8 monoclonal antibody 788 and an IgG fraction of goat anti-GDF8 polyclonal antiserum.

12. The fusion protein of claim 1 that elicits an immune response to GDF8 when presented to the immune system of a vertebrate, with or without an adjuvant.

13. The fusion protein of claim 12 comprising an antigenic fragment of a GDF8 peptide that comprises about 4 to about 16 consecutive amino acid residues from human GDF8.

14. A nucleic acid that encodes a fusion protein comprising:
   (a) a GDF8 peptide domain of 50 amino acids or fewer, or an antigenic fragment of the GDF8 peptide domain; and
   (b) a plant virus coat protein from a single-stranded plus-sense RNA virus, or at least one fragment of the plant virus coat protein;
   wherein the GDF8 peptide domain comprises amino acid residues 327 to 346 of SEQ ID NO:1, or the antigenic fragment of the GDF8 peptide domain comprises amino acid residues 327 to 338 of SEQ ID NO: 1; and wherein the fragment of the virus coat protein is missing from 1 to about 10 amino acid residues relative to the native virus coat protein, or has been divided into two or more domains by the insertion of the GDF8 peptide domain, or is missing from 1 to about 10 amino acid residues to the native virus coat protein and has been divided into two or more domains by the insertion of the GDF8 peptide domain.

15. The nucleic acid of claim 14 that comprises nucleotide 1112 to nucleotide 1171 of SEQ ID NO: 2.

16. A replicable vector comprising the nucleic acid of claim 14.

17. The replicable vector of claim 16 that is a selected from the group consisting of a plasmid, a phage, a cosmid, and a virus.

18. The replicable vector of claim 17 that is a tobamo virus.

19. The replicable vector of claim 18 that is a tobacco mosaic virus selected from the group consisting of TMV-FV1, TMV-FV2, TMV-FV3, TMV-FV4, TMV-FV5, TMV-FV6 and TMV-FV7.

20. A host cell comprising the replicable vector of claim 16.

21. The host cell of claim 20 that is a plant cell.

22. A method of producing a fusion protein comprising a GDF8 peptide domain or an antigenic fragment of a GDF8 peptide domain comprising the steps of:
    (a) culturing the host cell of claim 20; and
    (b) expressing the encoded fusion protein.

23. The method of claim 22 further comprising the step of recovering the fusion protein.

24. A fusion protein produced by the method of claim 23.

25. A vaccine composition comprising the fusion protein of claim 1.

26. The vaccine composition of claim 25, further comprising an adjuvant.

27. A method of eliciting an anti-GDF8 immune response in an animal, comprising administering to the animal an effective amount of the vaccine composition of claim 25.

28. A method of down-regulating GDF8 activity in an animal comprising immunizing the animal with an effective amount of the vaccine composition of claim 25.

* * * * *

UNITED STATES PATENT AND TRADEMARK OFFICE
CERTIFICATE OF CORRECTION

| | | |
|---|---|---|
| PATENT NO. | : 7,432,079 B2 | Page 1 of 22 |
| APPLICATION NO. | : 11/314397 | |
| DATED | : October 7, 2008 | |
| INVENTOR(S) | : David E. Junker et al. | |

It is certified that error appears in the above-identified patent and that said Letters Patent is hereby corrected as shown below:

At the Sequence Listing:

Col. 71, below line 31 to Col. 91, above line 24, please replace the Sequence Listing section with the following:

```
                        -- SEQUENCE LISTING

<160> 62

<170> PatentIn ver. 3.3

<210> 1
        <211> 375
        <212> PRT
        <213> Homo sapiens

<400> 1
        Met Gln Lys Leu Gln Leu Cys Val Tyr Ile Tyr Leu Phe Met Leu Ile
         1               5                  10                  15

Val Ala Gly Pro Val Asp Leu Asn Glu Asn Ser Glu Gln Lys Glu Asn
                        20                  25                  30

Val Glu Lys Glu Gly Leu Cys Asn Ala Cys Thr Trp Arg Gln Asn Thr
                    35                  40                  45

Lys Ser Ser Arg Ile Glu Ala Ile Lys Ile Gln Ile Leu Ser Lys Leu
                50                  55                  60
```

```
Arg Leu Glu Thr Ala Pro Asn Ile Ser Lys Asp Val Ile Arg Gln Leu
 65              70              75              80
Leu Pro Lys Ala Pro Pro Leu Arg Glu Leu Ile Asp Gln Tyr Asp Val
             85              90              95
Gln Arg Asp Asp Ser Ser Asp Gly Ser Leu Glu Asp Asp Tyr His
             100             105             110
Ala Thr Thr Glu Thr Ile Ile Thr Met Pro Thr Glu Ser Asp Phe Leu
         115             120             125
Met Gln Val Asp Gly Lys Pro Lys Cys Cys Phe Phe Lys Phe Ser Ser
     130             135             140
Lys Ile Gln Tyr Asn Lys Val Lys Ala Gln Leu Trp Ile Tyr Leu
 145             150             155             160
Arg Pro Val Glu Thr Pro Thr Thr Val Phe Val Gln Ile Leu Arg Leu
             165             170             175
Ile Lys Pro Met Lys Asp Gly Thr Arg Tyr Thr Gly Ile Arg Ser Leu
             180             185             190
Lys Leu Asp Met Asn Pro Gly Thr Gly Ile Trp Gln Ser Ile Asp Val
         195             200             205
Lys Thr Val Leu Gln Asn Trp Leu Lys Gln Pro Glu Ser Asn Leu Gly
 210             215             220
Ile Glu Ile Lys Ala Leu Asp Glu Asn Gly His Asp Leu Ala Val Thr
 225             230             235             240
Phe Pro Gly Pro Gly Glu Asp Gly Leu Asn Pro Phe Leu Glu Val Lys
             245             250             255
Val Thr Asp Thr Pro Lys Arg Ser Arg Arg Asp Phe Gly Leu Asp Cys
             260             265             270
Asp Glu His Ser Thr Glu Ser Arg Cys Cys Arg Tyr Pro Leu Thr Val
         275             280             285
Asp Phe Glu Ala Phe Gly Trp Asp Trp Ile Ile Ala Pro Lys Arg Tyr
     290             295             300
Lys Ala Asn Tyr Cys Ser Gly Glu Cys Glu Phe Val Phe Leu Gln Lys
 305             310             315             320
Tyr Pro His Thr His Leu Val His Gln Ala Asn Pro Arg Gly Ser Ala
             325             330             335
Gly Pro Cys Cys Thr Pro Thr Lys Met Ser Pro Ile Asn Met Leu Tyr
             340             345             350
Phe Asn Gly Lys Glu Gln Ile Ile Tyr Gly Lys Ile Pro Ala Met Val
         355             360             365
Val Asp Arg Cys Gly Cys Ser
 370             375
```

<210> 2
<211> 2823
<212> DNA
<213> Homo sapiens

<400> 2
```
agattcactg gtgtggcaag ttgtctctca gactgtacat gcattaaaat tttgcttggc   60
attactcaaa agcaaaagaa aagtaaaagg aagaaacaag aacaagaaaa aagattatat  120
tgatttaaa atcatgcaaa aactgcaact ctgtgtttat atttacctgt ttatgctgat  180
tgttgctggt ccagtggatc taaatgagaa cagtgagcaa aaagaaaatg tggaaaaaga  240
ggggctgtgt aatgcatgta cttggagaca aaacactaaa tcttcaagaa tagaagccat  300
taagatacaa atcctcagta aacttcgtct ggaaacagct cctaacatca gcaaagatgt  360
tataagacaa ctttaccca aagctcctcc actccgggaa ctgattgatc agtatgatgt  420
ccagagggat gacagcagcg atggctcttt ggaagatgac gattatcacg ctacaacgga  480
aacaatcatt accatgccta cagagtctga tttctaatg caagtggatg gaaaacccaa  540
atgttgcttc tttaaattta gctctaaaat acaatacaat aaagtagtaa aggcccaact  600
atggatatat ttgagacccg tcgagactcc tacaacagtg tttgtgcaaa tcctgagact  660
catcaaacct atgaaagacg gtacaaggta tactggaatc cgatctctga aacttgacat  720
gaacccaggc actggtattt ggcagagcat tgatgtgaag acagtgttgc aaaattggct  780
caaacaacct gaatccaact taggcattga aataaaagct ttagatgaga atggtcatga  840
tcttgctgta accttcccag gaccaggaga agatgggctg aatccgtttt tagaggtcaa  900
ggtaacagac acaccaaaaa gatccagaag ggattttggt cttgactgtg atgagcactc  960
aacagaatca cgatgctgtc gttaccctct aactgtggat tttgaagctt ttggatggga 1020
ttggattatc gctcctaaaa gatataaggc caattactgc tctggagagt gtgaatttgt 1080
attttacaa aaatatcctc atactcatct ggtacaccaa gcaaacccca gaggttcagc 1140
aggcccttgc tgtactccca caaagatgtc tccaattaat atgctatatt taatgcaa   1200
agaacaaata atatatggga aaattccagc gatggtagta gaccgctgtg ggtgctcatg 1260
agatttatat taagcgttca taacttccta aaacatggaa ggttttcccc tcaacaattt 1320
tgaagctgtg aaattaagta ccacaggcta taggcctaga gtatgctaca gtcacttaag 1380
cataagctac agtatgtaaa ctaaagggg gaatatatgc aatggttggc atttaaccat 1440
ccaaacaaat catacaagaa agttttatga tttccagagt ttttgagcta gaaggagatc 1500
aaattacatt tatgttccta tatattacaa catcggcgag gaaatgaaag cgattctcct 1560
tgagttctga tgaattaaag gagtatgctt taaagtctat ttctttaaag ttttgtttaa 1620
tattacaga aaaatccaca tacagtattg gtaaaatgca ggattgttat ataccatcat 1680
tcgaatcatc cttaaacact tgaatttata ttgtatggta gtatacttgg taagataaaa 1740
ttccacaaaa atagggatgg tgcagcatat gcaatttcca ttcctattat aattgacaca 1800
gtacattaac aatccatgcc aacggtgcta atacgatagg ctgaatgtct gaggctacca 1860
ggtttatcac ataaaaaaca ttcagtaaaa tagtaagttt ctcttttctt caggggcatt 1920
ttcctacacc tccaaatgag gaatggattt tctttaatgt aagaagaatc atttttctag 1980
aggttggctt tcaattctgt agcatacttg gagaaactgc attatcttaa aaggcagtca 2040
aatggtgttt gttttatca aaatgtcaaa ataacatact tggagaagta tgtaatttg  2100
tctttggaaa attacaacac tgcctttgca acactgcagt ttttatggta aaataataga 2160
aatgatcgac tctatcaata ttgtataaaa agactgaaac aatgcattta tataatatgt 2220
atacaatatt gttttgtaaa taagtgtctc ctttttttatt tactttggta tattttaca  2280
ctaaggacat ttcaaattaa gtactaaggc acaaagacat gtcatgcatc acagaaaagc 2340
aactacttat atttcagagc aaattagcag attaaatagt ggtcttaaaa ctccatatgt 2400
taatgattag atggttatat tacaatcatt ttatattttt tacatgatt aacattcact  2460
tatggattca tgatggctgt ataagtgaa tttgaaattt caatggttta ctgtcattgt 2520
gtttaaatct caacgttcca ttatttaat acttgcaaaa acattactaa gtataccaaa 2580
ataattgact ctattatctg aaatgaagaa taaactgatg ctatctcaac aataactgtt 2640
acttttattt tataatttga taatgaatat atttctgcat ttattactt ctgttttgta 2700
aattgggatt ttgttaatca aatttattgt actatgacta aatgaaatta tttcttacat 2760
ctaatttgta gaaacagtat aagttatatt aaagtgtttt cacattttt tgaaagacaa 2820
aaa                                                               2823
```

<210> 3
<211> 1164
<212> DNA
<213> Artificial Sequence

<220>
<223> Description of Artificial Sequence: Synthetic
nucleotide construct

<400> 3
```
atggatctac agaagttgca gttgtgtgtc tacatctatt tgttcatgtt gatcgtcgcc  60
ggacctgttg acttgaacga aaattctgaa cagaaggaga acgttgagaa ggaaggtttg 120
tgcaacgctt gtacatggcg tcaaaataca aagtcctctc gtattgaagc tatcaagatt 180
caaattttgt ctaagttgag attggaaact gccccaaata tttctaagga cgtcattcgt 240
caattgttgc caaaggcccc acctttgaga gaattgatcg accaatacga tgttcaaaga 300
gacgattctt ctgacggttc ccttgaagac gatgactacc atgccactac tgaaactatt 360
atcactatgc caactgaatc cgactttttg atgcaggttg atggtaagcc aaagtgctgt 420
ttttcaagt tctcttccaa gattcaatac aacaaggttg ttaaagctca attgtggatt 480
taccttcgtc cagttgaaac accaactact gtgtttgttc agatttgcg tttgattaag 540
ccaatgaagg atggaactag atacacaggt attagatcct tgaagttgga tatgaatcct 600
ggtacaggaa tctggcaatc tatcgacgtt aaaactgttc ttcaaaactg gttgaagcaa 660
ccagagtcta atttgggtat cgagattaag gccttggacg aaaacggaca tgacttggcc 720
gttactttc ctggtcctgg tgaagacggt ttgaacccat ttctggaagt taaggttact 780
gatactccta agcgttccag gagagacttc ggattggatt gtgatgaaca ttctactgag 840
tctagatgtt gtagatatcc attgaccgtt gatttcgagg ccttcggttg ggattggatc 900
attgccccaa agagatacaa agctaactat tgttccggtg aatgtgagtt cgtttcttg 960
cagaagtacc cacataccca tttggttcat caggctaatc caagaggatc tgctggtcca 1020
tgttgtaccc caactaaaat gtcccctatc aacatgttgt acttcaacgg taaggagcag 1080
attatttacg gtaagatccc tgctatggtt gttgatagat gtggttgttc tctcgaggat 1140
```
tacaaggatg acgacgataa gtag                                        1164

<210> 4
<211> 20
<212> PRT
<213> Homo sapiens

<400> 4
Asp Phe Gly Leu Asp Cys Asp Glu His Ser Thr Glu Ser Arg Cys Cys
 1               5                  10                  15

Arg Tyr Pro Leu
            20

<210> 5
<211> 20
<212> PRT
<213> Homo sapiens

<400> 5
Cys Arg Tyr Pro Leu Thr Val Asp Phe Glu Ala Phe Gly Trp Asp Trp
 1               5                  10                  15

Ile Ile Ala Pro
            20

```
<210> 6
<211> 20
<212> PRT
<213> Homo sapiens

<400> 6
Trp Ile Ile Ala Pro Lys Arg Tyr Lys Ala Asn Tyr Cys Ser Gly Glu
 1               5                  10                  15
Cys Glu Phe Val
            20

<210> 7
<211> 20
<212> PRT
<213> Homo sapiens

<400> 7
Glu Cys Glu Phe Val Phe Leu Gln Lys Tyr Pro His Thr His Leu Val
 1               5                  10                  15
His Gln Ala Asn
            20

<210> 8
<211> 20
<212> PRT
<213> Homo sapiens

<400> 8
Val His Gln Ala Asn Pro Arg Gly Ser Ala Gly Pro Cys Cys Thr Pro
 1               5                  10                  15
Thr Lys Met Ser
            20

<210> 9
<211> 20
<212> PRT
<213> Homo sapiens

<400> 9
Pro Thr Lys Met Ser Pro Ile Asn Met Leu Tyr Phe Asn Gly Lys Glu
 1               5                  10                  15
Gln Ile Ile Tyr
            20

<210> 10
<211> 19
<212> PRT
<213> Homo sapiens

<400> 10
Glu Gln Ile Ile Tyr Gly Lys Ile Pro Ala Met Val Val Asp Arg Cys
 1               5                  10                  15
Gly Cys Ser
```

```
<210> 11
<211> 20
<212> PRT
<213> Anas platyrhynchos

<400> 11
Val His Gln Ala Asn Pro Arg Gly Ser Ala Gly Pro Cys Cys Thr Pro
1               5                   10                  15

Thr Lys Met Ser
            20

<210> 12
<211> 20
<212> PRT
<213> Anser anser

<400> 12
Val His Gln Ala Asn Pro Arg Gly Ser Ala Gly Pro Cys Cys Thr Pro
1               5                   10                  15

Thr Lys Met Ser
            20

<210> 13
<211> 20
<212> PRT
<213> Anser anser

<400> 13
Val Leu Gln Ala Asn Pro Arg Gly Ser Ala Gly Pro Cys Cys Thr Pro
1               5                   10                  15

Thr Lys Met Ser
            20

<210> 14
<211> 20
<212> PRT
<213> Bos taurus

<400> 14
Val His Gln Ala Asn Pro Arg Gly Ser Ala Gly Pro Cys Cys Thr Pro
1               5                   10                  15

Thr Lys Met Ser
            20

<210> 15
<211> 20
<212> PRT
<213> Canis familiaris

<400> 15
Val His Gln Ala Asn Pro Arg Gly Ser Ala Gly Pro Cys Cys Thr Pro
1               5                   10                  15

Thr Lys Met Ser
            20
```

```
<210> 16
<211> 20
<212> PRT
<213> Capra hircus

<400> 16
Val His Gln Ala Asn Pro Lys Gly Ser Ala Gly Pro Cys Cys Thr Pro
 1               5                  10                  15

Thr Lys Met Ser
            20

<210> 17
<211> 20
<212> PRT
<213> Columba livia

<400> 17
Val His Gln Ala Asn Pro Arg Gly Ser Ala Gly Pro Cys Cys Thr Pro
 1               5                  10                  15

Thr Lys Met Ser
            20

<210> 18
<211> 20
<212> PRT
<213> Coturnix chinensis

<400> 18
Val His Gln Ala Asn Pro Arg Gly Ser Ala Gly Pro Cys Cys Thr Pro
 1               5                  10                  15

Thr Lys Met Ser
            20

<210> 19
<211> 20
<212> PRT
<213> Danio rerio

<400> 19
Val Asn Lys Ala Ser Pro Arg Gly Thr Ala Gly Pro Cys Cys Thr Pro
 1               5                  10                  15

Thr Lys Met Ser
            20

<210> 20
<211> 20
<212> PRT
<213> Equus caballus

<400> 20
Val His Gln Ala Asn Pro Arg Gly Ser Ala Gly Pro Cys Cys Thr Pro
 1               5                  10                  15

Thr Lys Met Ser
            20
```

<210> 21
<211> 20
<212> PRT
<213> Gallus gallus

<400> 21
Val His Gln Ala Asn Pro Arg Gly Pro Ala Gly Pro Cys Cys Thr Pro
1               5                  10                  15
Thr Lys Met Ser
            20

<210> 22
<211> 20
<212> PRT
<213> Gallus gallus

<400> 22
Val His Gln Ala Asn Pro Arg Gly Ser Ala Gly Pro Cys Cys Thr Pro
1               5                  10                  15
Thr Lys Met Ser
            20

<210> 23
<211> 20

<212> PRT
<213> Ictalurus punctatus

<400> 23
Val Asn Lys Ala Asn Pro Arg Gly Thr Ala Gly Pro Cys Cys Thr Pro
1               5                  10                  15
Thr Lys Met Ser
            20

<210> 24
<211> 20
<212> PRT
<213> Lepus capensis

<400> 24
Val His Gln Ala Asn Pro Arg Gly Ser Ala Gly Pro Cys Cys Thr Pro
1               5                  10                  15
Thr Lys Met Ser
            20

<210> 25
<211> 20
<212> PRT
<213> Macaca fascicularis

<400> 25
Val His Gln Ala Asn Pro Arg Gly Ser Ala Gly Pro Cys Cys Thr Pro
1               5                  10                  15

Thr Lys Met Ser
            20

<210> 26
<211> 20
<212> PRT
<213> Meleagris gallopavo

<400> 26
Val His Gln Ala Asn Pro Arg Gly Ser Ala Gly Pro Cys Cys Thr Pro
 1               5                  10                  15
Thr Lys Met Ser
            20

<210> 27
<211> 20
<212> PRT
<213> Morone chrysops

<400> 27
Val Asn Lys Ala Asn Pro Arg Gly Thr Ala Gly Pro Cys Cys Thr Pro
 1               5                  10                  15
Thr Lys Met Ser
            20

<210> 28
<211> 20
<212> PRT
<213> Mus musculus

<400> 28
Val His Gln Ala Asn Pro Arg Gly Ser Ala Gly Pro Cys Cys Thr Pro
 1               5                  10                  15
Thr Lys Met Ser
            20

<210> 29
<211> 20
<212> PRT
<213> Oncorhynchus mykiss

<400> 29
Val Asn Lys Ala Asn Pro Arg Gly Thr Ala Gly Pro Cys Cys Thr Pro
 1               5                  10                  15
Thr Lys Met Ser
            20

<210> 30
<211> 20
<212> PRT
<213> Ovis aries

<400> 30
Val His Gln Ala Asn Pro Lys Gly Ser Ala Gly Pro Cys Cys Thr Pro
1               5                   10                  15
Thr Lys Met Ser
            20

<210> 31
<211> 20
<212> PRT
<213> Papio hamadryas

<400> 31
Val His Gln Ala Asn Pro Arg Gly Ser Ala Gly Pro Cys Cys Thr Pro
1               5                   10                  15
Thr Lys Met Ser
            20

<210> 32
<211> 20
<212> PRT
<213> Rattus norvegicus

<400> 32
Val His Gln Ala Asn Pro Arg Gly Ser Ala Gly Pro Cys Cys Thr Pro
1               5                   10                  15
Thr Lys Met Ser
            20

<210> 33
<211> 20
<212> PRT
<213> Salmo salar

<400> 33
Val Asn Lys Ala Asn Pro Arg Gly Thr Ala Gly Pro Cys Cys Thr Pro
1               5                   10                  15
Thr Lys Met Ser
            20

<210> 34
<211> 20
<212> PRT
<213> Sparus aurata

<400> 34
Val Asn Lys Ala Asn Pro Arg Gly Thr Ala Gly Pro Cys Cys Thr Pro
1               5                   10                  15
Thr Lys Met Ser
            20

<210> 35
<211> 20
<212> PRT
<213> Sus scrofa

```
<400> 35
Val His Gln Ala Asn Pro Arg Gly Ser Ala Gly Pro Cys Cys Thr Pro
 1               5                  10                  15
Thr Lys Met Ser
            20

<210> 36
<211> 20
<212> PRT
<213> Sus scrofa

<400> 36
Val Leu Gln Ala Asn Pro Arg Gly Ser Ala Gly Pro Cys Cys Thr Pro
 1               5                  10                  15
Thr Lys Met Ser
            20

<210> 37
<211> 26
<212> DNA
<213> Artificial Sequence

<220>
<223> Description of Artificial Sequence: Synthetic
      primer

<400> 37
gcgcacatgt cttacagtat cactac                                        26

<210> 38
<211> 46
<212> DNA
<213> Artificial Sequence

<220>
<223> Description of Artificial Sequence: Synthetic
      primer

<400> 38
tggtcctgca actgccatgg acagtgccgg ctgaggtagt caagat                  46

<210> 39
<211> 22
<212> DNA
<213> Artificial Sequence

<220>
<223> Description of Artificial Sequence: Synthetic
      primer

<400> 39
cggataacaa tttcacacag ga                                            22
```

```
<210> 40
<211> 27
<212> DNA
<213> Artificial Sequence

<220>
<223> Description of Artificial Sequence: Synthetic
      oligonucleotide

<400> 40
ccacatgtat acaatcaact ctccgag                                          27

<210> 41
<211> 21
<212> DNA
<213> Artificial Sequence

<220>
<223> Description of Artificial Sequence: Synthetic
      oligonucleotide

<400> 41
cactgtccat ggctgtggtc c                                                21

<210> 42
<211> 48
<212> DNA
<213> Artificial Sequence

<220>
<223> Description of Artificial Sequence: Synthetic
      oligonucleotide

<400> 42
cttgtctgga ccacagccat ggacagtgcc ggcactccgg ctacttag                   48

<210> 43
<211> 26
<212> DNA
<213> Artificial Sequence

<220>
<223> Description of Artificial Sequence: Synthetic
      oligonucleotide

<400> 43
aaacatgatt acgccaagct tgcatg                                           26

<210> 44
<211> 12
<212> PRT
<213> Homo sapiens

<400> 44
Val His Gln Ala Asn Pro Arg Gly Ser Ala Gly Pro
 1               5                  10
```

```
<210> 45
<211> 64
<212> DNA
<213> Artificial Sequence

<220>
<223> Description of Artificial Sequence: Synthetic
      oligonucleotides <400> 45
catggttcat caagctaatc cagaggatct gctggaccat gttgtactcc aactaagatg    60
tctg                                                                 64

<210> 46
<211> 65
<212> DNA
<213> Artificial Sequence

<220>
<223> Description of Artificial Sequence: Synthetic
      oligonucleotides <400> 46
ccggcagaca tcttagttgg agtacaacat ggtccagcag atcctcttgg attagcttga    60
tgaac                                                                65

<210> 47
<211> 182
<212> PRT
<213> Artificial Sequence

<220>
<223> Description of Artificial Sequence: Synthetic
      amino acid construct <400> 47
Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125
```

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Ala Met Val His Gln
145             150                 155                 160

Ala Asn Pro Arg Gly Ser Ala Gly Pro Cys Cys Thr Pro Thr Lys Met
            165                 170                 175

Ser Ala Gly Pro Ala Thr
            180

<210> 48
<211> 183
<212> PRT
<213> Artificial Sequence

<220>
<223> Description of Artificial Sequence: Synthetic
      amino acid construct <400> 48
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
            20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
    50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
            100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Gly Pro Ala Thr Ala
145             150                 155                 160

Met Val His Gln Ala Asn Pro Arg Gly Ser Ala Gly Pro Cys Cys Thr
                165                 170                 175

Pro Thr Lys Met Ser Ala Gly
            180

<210> 49
<211> 181
<212> PRT
<213> Artificial Sequence

<220>
<223> Description of Artificial Sequence: Synthetic
    amino acid construct

<400> 49

```
Met Val His Gln Ala Asn Pro Arg Gly Ser Ala Gly Pro Cys Cys Thr
 1               5                  10                  15
Pro Thr Lys Met Ser Ala Gly Ser Tyr Ser Ile Thr Thr Pro Ser Gln
             20                  25                  30
Phe Val Phe Leu Ser Ser Ala Trp Ala Asp Pro Ile Glu Leu Ile Asn
         35                  40                  45
Leu Cys Thr Asn Ala Leu Gly Asn Gln Phe Gln Thr Gln Gln Ala Arg
     50                  55                  60
Thr Val Val Gln Arg Gln Phe Ser Glu Val Trp Lys Pro Ser Pro Gln
 65                  70                  75                  80
Val Thr Val Arg Phe Pro Asp Ser Asp Phe Lys Val Tyr Arg Tyr Asn
                 85                  90                  95
Ala Val Leu Asp Pro Leu Val Thr Ala Leu Leu Gly Ala Phe Asp Thr
            100                 105                 110
Arg Asn Arg Ile Ile Glu Val Glu Asn Gln Ala Asn Pro Thr Thr Ala
        115                 120                 125
Glu Thr Leu Asp Ala Thr Arg Arg Val Asp Asp Ala Thr Val Ala Ile
    130                 135                 140
Arg Ser Ala Ile Asn Asn Leu Ile Val Glu Leu Ile Arg Gly Thr Gly
145                 150                 155                 160
Ser Tyr Asn Arg Ser Ser Phe Glu Ser Ser Ser Gly Leu Val Trp Thr
                165                 170                 175
Ser Gly Pro Ala Thr
            180
```

<210> 50
<211> 186
<212> PRT
<213> Artificial Sequence

<220>
<223> Description of Artificial Sequence: Synthetic
    amino acid construct

<400> 50

```
Met Ser Tyr Ser Ile Thr Thr Pro Ser Gln Phe Val Phe Leu Ser Ser
 1               5                  10                  15
Ala Trp Ala Asp Pro Ile Glu Leu Ile Asn Leu Cys Thr Asn Ala Leu
             20                  25                  30
Gly Asn Gln Phe Gln Thr Gln Gln Ala Arg Thr Val Val Gln Arg Gln
         35                  40                  45
```

```
Phe Ser Glu Val Trp Lys Pro Ser Pro Gln Val Thr Val Arg Phe Pro
 50                  55                  60
Gly Ser Pro Met Val His Gln Ala Asn Pro Arg Gly Ser Ala Gly Pro
 65                  70                  75                  80
Cys Cys Thr Pro Thr Lys Met Ser Ala Gly Pro Ser Gly Asp Phe Lys
                 85                  90                  95
Val Tyr Arg Tyr Asn Ala Val Leu Asp Pro Leu Val Thr Ala Leu Leu
            100                 105                 110
Gly Ala Phe Asp Thr Arg Asn Arg Ile Ile Glu Val Glu Asn Gln Ala
        115                 120                 125
Asn Pro Thr Thr Ala Glu Thr Leu Asp Ala Thr Arg Arg Val Asp Asp
    130                 135                 140
Ala Thr Val Ala Ile Arg Ser Ala Ile Asn Asn Leu Ile Val Glu Leu
145                 150                 155                 160
Ile Arg Gly Thr Gly Ser Tyr Asn Arg Ser Ser Phe Glu Ser Ser Ser
                165                 170                 175
Gly Leu Val Trp Thr Ser Gly Pro Ala Thr
                180                 185
```

<210> 51
<211> 182
<212> PRT
<213> Artificial Sequence

<220>
<223> Description of Artificial Sequence: Synthetic
      amino acid construct <400> 51
```
Met Tyr Thr Ile Asn Ser Pro Ser Gln Phe Val Tyr Leu Ser Ser Ala
 1               5                  10                  15
Tyr Ala Asp Pro Val Gln Leu Ile Asn Leu Cys Thr Asn Ala Leu Gly
             20                  25                  30
Asn Gln Phe Gln Thr Gln Gln Ala Arg Thr Thr Val Gln Gln Gln Phe
         35                  40                  45
Ala Asp Ala Trp Lys Pro Val Pro Ser Met Thr Val Arg Phe Pro Ala
 50                  55                  60
Ser Asp Phe Tyr Val Tyr Arg Tyr Asn Ser Thr Leu Asp Pro Leu Ile
 65                  70                  75                  80
Thr Ala Leu Leu Asn Ser Phe Asp Thr Arg Asn Arg Ile Ile Glu Val
                 85                  90                  95
Asp Asn Gln Pro Ala Pro Asn Thr Thr Glu Ile Val Asn Ala Thr Gln
            100                 105                 110
```

```
Arg Val Asp Asp Ala Thr Val Ala Ile Arg Ala Ser Ile Asn Asn Leu
        115                 120                 125

Ala Asn Glu Leu Val Arg Gly Thr Gly Met Phe Asn Gln Ala Ser Phe
        130                 135                 140

Glu Thr Ala Ser Gly Leu Val Trp Thr Thr Ala Met Val His Gln Ala
145                 150                 155                 160

Asn Pro Arg Gly Ser Ala Gly Pro Cys Cys Thr Pro Thr Lys Met Ser
                165                 170                 175

Ala Gly Thr Pro Ala Thr
            180
```

<210> 52
<211> 41
<212> DNA
<213> Artificial Sequence

<220>
<223> Description of Artificial Sequence: Synthetic
      primer

<400> 52
catggttcat caagctaatc caagaggatc tgctggacca g           41

<210> 53
<211> 41
<212> DNA
<213> Artificial Sequence

<220>
<223> Description of Artificial Sequence: Synthetic
      primer

<400> 53
ccggctggtc cagcagatcc tcttggatta gcttgatgaa c           41

<210> 54
<211> 173
<212> PRT
<213> Artificial Sequence

<220>
<223> Description of Artificial Sequence: Synthetic
      amino acid construct

```
<400> 54
Met Val His Gln Ala Asn Pro Arg Gly Ser Ala Gly Pro Ala Gly Ser
1               5                   10                  15

Tyr Ser Ile Thr Thr Pro Ser Gln Phe Val Phe Leu Ser Ser Ala Trp
            20                  25                  30

Ala Asp Pro Ile Glu Leu Ile Asn Leu Cys Thr Asn Ala Leu Gly Asn
        35                  40                  45
```

```
Gln Phe Gln Thr Gln Gln Ala Arg Thr Val Val Gln Arg Gln Phe Ser
         50                  55                  60
Glu Val Trp Lys Pro Ser Pro Gln Val Thr Val Arg Phe Pro Asp Ser
 65                  70                  75                  80
Asp Phe Lys Val Tyr Arg Tyr Asn Ala Val Leu Asp Pro Leu Val Thr
                 85                  90                  95
Ala Leu Leu Gly Ala Phe Asp Thr Arg Asn Arg Ile Ile Glu Val Glu
            100                 105                 110
Asn Gln Ala Asn Pro Thr Thr Ala Glu Thr Leu Asp Ala Thr Arg Arg
        115                 120                 125
Val Asp Asp Ala Thr Val Ala Ile Arg Ser Ala Ile Asn Asn Leu Ile
    130                 135                 140
Val Glu Leu Ile Arg Gly Thr Gly Ser Tyr Asn Arg Ser Ser Phe Glu
145                 150                 155                 160
Ser Ser Ser Gly Leu Val Trp Thr Ser Gly Pro Ala Thr
                165                 170

<210> 55
<211> 174
<212> PRT
<213> Artificial Sequence

<220>
<223> Description of Artificial Sequence: Synthetic
      amino acid construct <400> 55
Met Ser Tyr Ser Ile Thr Thr Pro Ser Gln Phe Val Phe Leu Ser Ser
 1               5                  10                  15
Ala Trp Ala Asp Pro Ile Glu Leu Ile Asn Leu Cys Thr Asn Ala Leu
             20                  25                  30
Gly Asn Gln Phe Gln Thr Gln Gln Ala Arg Thr Val Val Gln Arg Gln
         35                  40                  45
Phe Ser Glu Val Trp Lys Pro Ser Pro Gln Val Thr Val Arg Phe Pro
 50                  55                  60
Asp Ser Asp Phe Lys Val Tyr Arg Tyr Asn Ala Val Leu Asp Pro Leu
 65                  70                  75                  80
Val Thr Ala Leu Leu Gly Ala Phe Asp Thr Arg Asn Arg Ile Ile Glu
                 85                  90                  95
Val Glu Asn Gln Ala Asn Pro Thr Thr Ala Glu Thr Leu Asp Ala Thr
            100                 105                 110
Arg Arg Val Asp Asp Ala Thr Val Ala Ile Arg Ser Ala Ile Asn Asn
        115                 120                 125
Leu Ile Val Glu Leu Ile Arg Gly Thr Gly Ser Tyr Asn Arg Ser Ser
    130                 135                 140
```

```
Phe Glu Ser Ser Ser Gly Leu Val Trp Thr Ser Ala Met Val His Gln
145                 150                 155                 160

Ala Asn Pro Arg Gly Ser Ala Gly Pro Ala Gly Pro Ala Thr
                165                 170
```

<210> 56
<211> 159
<212> PRT
<213> Tobacco mosaic virus

<400> 56
```
Met Ser Tyr Ser Ile Thr Thr Pro Ser Gln Phe Val Phe Leu Ser Ser
1               5                   10                  15

Ala Trp Ala Asp Pro Ile Glu Leu Ile Asn Leu Cys Thr Asn Ala Leu
                20                  25                  30

Gly Asn Gln Phe Gln Thr Gln Gln Ala Arg Thr Val Val Gln Arg Gln
                35                  40                  45

Phe Ser Glu Val Trp Lys Pro Ser Pro Gln Val Thr Val Arg Phe Pro
        50                  55                  60

Asp Ser Asp Phe Lys Val Tyr Arg Tyr Asn Ala Val Leu Asp Pro Leu
65                  70                  75                  80

Val Thr Ala Leu Leu Gly Ala Phe Asp Thr Arg Asn Arg Ile Ile Glu
                85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
        115                 120                 125

Leu Ile Val Glu Leu Ile Arg Gly Thr Gly Ser Tyr Asn Arg Ser Ser
130                 135                 140

Phe Glu Ser Ser Ser Gly Leu Val Trp Thr Ser Gly Pro Ala Thr
145                 150                 155
```
<210> 57
<211> 159
<212> PRT
<213> Tobacco mild green mosaic virus
<400> 57
```
Met Pro Tyr Thr Ile Asn Ser Pro Ser Gln Phe Val Tyr Leu Ser Ser
1               5                   10                  15

Ala Tyr Ala Asp Pro Val Gln Leu Ile Asn Leu Cys Thr Asn Ala Leu
                20                  25                  30

Gly Asn Gln Phe Gln Thr Gln Gln Ala Arg Thr Thr Val Gln Gln Gln
                35                  40                  45

Phe Ala Asp Ala Trp Lys Pro Val Pro Ser Met Thr Val Arg Phe Pro
        50                  55                  60
```

```
         Ala Ser Asp Phe Tyr Val Tyr Arg Tyr Asn Ser Thr Leu Asp Pro Leu
          65                  70                  75                  80

Ile Thr Ala Leu Leu Asn Ser Phe Asp Thr Arg Asn Arg Ile Ile Glu
                          85                  90                  95

Val Asp Asn Gln Pro Ala Pro Asn Thr Thr Glu Ile Val Asn Ala Thr
                     100                 105                 110

Gln Arg Val Asp Asp Ala Thr Val Ala Ile Arg Ala Ser Ile Asn Asn
                     115                 120                 125

Leu Ala Asn Glu Leu Val Arg Gly Thr Gly Met Phe Asn Gln Ala Ser
                     130                 135                 140

Phe Glu Thr Ala Ser Gly Leu Val Trp Thr Thr Thr Pro Ala Thr
         145                 150                 155
```

<210> 58
<211> 4
<212> PRT
<213> Unknown Organism

<220>
<223> Description of Unknown Organism: Peptide sequence
      from Tobacco mosaic virus or Homo sapiens <400> 58
Gln Ala Asn Pro
  1

<210> 59
<211> 30
<212> DNA
<213> Artificial Sequence

<220>
<223> Description of Artificial Sequence: Synthetic
      oligonucleotide

<400> 59
ccttaattaa tggatctaca gaagttgcag                                    30

<210> 60
<211> 31
<212> DNA
<213> Artificial Sequence

<220>
<223> Description of Artificial Sequence: Synthetic
      oligonucleotide

<400> 60
cttgtcgacc tacttatcgt cgtcatcctt g                                  31

<210> 61
<211> 1195
<212> DNA
<213> Artificial Sequence

<220>
<223> Description of Artificial Sequence: Synthetic
        nucleotide construct <400> 61
ttaattaatg gatctacaga agttgcagtt gtgtgtctac atctatttgt tcatgttgat 60
cgtcgccgga cctgttgact tgaacgaaaa ttctgaacag aaggagaacg ttgagaagga 120
aggtttgtgc aacgcttgta catggcgtca aaatacaaag tcctctcgta ttgaagctat 180
caagattcaa attttgtcta agttgagatt ggaaactgcc ccaaatattt ctaaggacgt 240
cattcgtcaa ttgttgccaa aggccccacc tttgagagaa ttgatcgacc aatacgatgt 300
tcaaagagac gattcttctg acggttccct tgaaagacgat gactaccatg ccactactga 360
aactattatc actatgccaa ctgaatccga cttttgatg caggttgatg gtaagccaaa 420
gtgctgtttt ttcaagttct cttccaagat tcaatacaac aaggttgtta aagctcaatt 480
gtggatttac cttcgtccag ttgaaacacc aactactgtg tttgttcaga ttttgcgttt 540
gattaagcca atgaaggatg gaactagata cacaggtatt agatccttga agttggatat 600
gaatcctggt acaggaatct ggcaatctat cgacgttaaa actgttcttc aaaactggtt 660
gaagcaacca gagtctaatt tgggtatcga gattaaggcc ttggacgaaa acggacatga 720
cttggccgtt actttttcctg gtcctggtga agacggtttg aacccatttc tggaagttaa 780
ggttactgat actcctaagc gttccaggag agacttcgga ttggattgtg atgaacattc 840
tactgagtct agatgttgta gatatccatt gaccgttgat ttcgaggcct tcggttggga 900
ttggatcatt gccccaaaga gatacaaagc taactattgt tccggtgaat gtgagttcgt 960
tttcttgcag aagtacccac atacccattt ggttcatcag gctaatccaa gaggatctgc 1020
tggtccatgt tgtaccccaa ctaaaatgtc ccctatcaac atgttgtact tcaacggtaa 1080
ggagcagatt atttacggta agatccctgc tatggttgtt gatagatgtg ttgttctct 1140
cgaggattac aaggatgacg acgataagta ggtcgagggg tagtcaagat gcata 1195

<210> 62
<211> 387
<212> PRT
<213> Artificial Sequence

<220>
<223> Description of Artificial Sequence: Synthetic
        amino acid construct <400> 62
Met Asp Leu Gln Lys Leu Gln Leu Cys Val Tyr Ile Tyr Leu Phe Met
1               5                   10                  15

Leu Ile Val Ala Gly Pro Val Asp Leu Asn Glu Asn Ser Glu Gln Lys
            20                  25                  30

Glu Asn Val Glu Lys Glu Gly Leu Cys Asn Ala Cys Thr Trp Arg Gln
        35                  40                  45

Asn Thr Lys Ser Ser Arg Ile Glu Ala Ile Lys Ile Gln Ile Leu Ser
    50                  55                  60

Lys Leu Arg Leu Glu Thr Ala Pro Asn Ile Ser Lys Asp Val Ile Arg
65                  70                  75                  80

Gln Leu Leu Pro Lys Ala Pro Pro Leu Arg Glu Leu Ile Asp Gln Tyr
                85                  90                  95

Asp Val Gln Arg Asp Asp Ser Ser Asp Gly Ser Leu Glu Asp Asp Asp
            100                 105                 110

Tyr His Ala Thr Thr Glu Thr Ile Ile Thr Met Pro Thr Glu Ser Asp
        115                 120                 125

Phe Leu Met Gln Val Asp Gly Lys Pro Lys Cys Cys Phe Phe Lys Phe
    130                 135                 140

```
Ser Ser Lys Ile Gln Tyr Asn Lys Val Val Lys Ala Gln Leu Trp Ile
145                 150                 155                 160
Tyr Leu Arg Pro Val Glu Thr Pro Thr Thr Val Phe Val Gln Ile Leu
            165             170                 175
Arg Leu Ile Lys Pro Met Lys Asp Gly Thr Arg Tyr Thr Gly Ile Arg
            180             185                 190
Ser Leu Lys Leu Asp Met Asn Pro Gly Thr Gly Ile Trp Gln Ser Ile
            195             200                 205
Asp Val Lys Thr Val Leu Gln Asn Trp Leu Lys Gln Pro Glu Ser Asn
            210             215                 220
Leu Gly Ile Glu Ile Lys Ala Leu Asp Glu Asn Gly His Asp Leu Ala
225                 230                 235                 240
Val Thr Phe Pro Gly Pro Gly Glu Asp Gly Leu Asn Pro Phe Leu Glu
            245             250                 255
Val Lys Val Thr Asp Thr Pro Lys Arg Ser Arg Arg Asp Phe Gly Leu
            260             265                 270
Asp Cys Asp Glu His Ser Thr Glu Ser Arg Cys Cys Arg Tyr Pro Leu
        275             280                 285
Thr Val Asp Phe Glu Ala Phe Gly Trp Asp Trp Ile Ile Ala Pro Lys
290                 295                 300
Arg Tyr Lys Ala Asn Tyr Cys Ser Gly Glu Cys Glu Phe Val Phe Leu
305                 310                 315                 320
Gln Lys Tyr Pro His Thr His Leu Val His Gln Ala Asn Pro Arg Gly
                325             330                 335
Ser Ala Gly Pro Cys Cys Thr Pro Thr Lys Met Ser Pro Ile Asn Met
            340             345                 350
Leu Tyr Phe Asn Gly Lys Glu Gln Ile Ile Tyr Gly Lys Ile Pro Ala
            355             360                 365
Met Val Val Asp Arg Cys Gly Cys Ser Leu Glu Asp Tyr Lys Asp Asp
    370             375                 380
Asp Asp Lys
385 --
```

Signed and Sealed this

Nineteenth Day of January, 2010

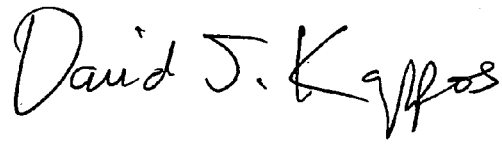

David J. Kappos
*Director of the United States Patent and Trademark Office*